US012558225B2

(12) United States Patent (10) Patent No.: US 12,558,225 B2
Peretz et al. (45) Date of Patent: Feb. 24, 2026

(54) SACROILIAC JOINT FIXATION

(71) Applicant: GLOBUS MEDICAL, INC., Audubon, PA (US)

(72) Inventors: David Peretz, Wynnewood, PA (US); Hannah Fischer, West Chester, PA (US); Jakeb Baldridge, Philadelphia, PA (US); Andrew Fluck, Gilbertsville, PA (US); Caelan Allen, Ambler, PA (US)

(73) Assignee: Globus Medical, Inc., Audubon, PA (US)

( * ) Notice: Subject to any disclaimer, the term of this patent is extended or adjusted under 35 U.S.C. 154(b) by 344 days.

(21) Appl. No.: 18/149,960

(22) Filed: Jan. 4, 2023

(65) Prior Publication Data

US 2024/0180710 A1 Jun. 6, 2024

Related U.S. Application Data

(63) Continuation of application No. 18/060,607, filed on Dec. 1, 2022.

(51) Int. Cl.
| | |
|---|---|
| *A61F 2/30* | (2006.01) |
| *A61B 17/56* | (2006.01) |
| *A61B 17/70* | (2006.01) |
| *A61F 2/28* | (2006.01) |
| *A61F 2/46* | (2006.01) |

(52) U.S. Cl.
CPC ...... *A61F 2/30988* (2013.01); *A61B 17/7002* (2013.01); *A61F 2/30749* (2013.01); *A61B 2017/564* (2013.01); *A61F 2002/2835*
(2013.01); *A61F 2002/30131* (2013.01); *A61F 2002/30138* (2013.01); *A61F 2002/30143* (2013.01); *A61F 2002/30205* (2013.01); *A61F 2002/30235* (2013.01); *A61F 2002/30327* (2013.01); *A61F 2002/30354* (2013.01); *A61F 2002/30383* (2013.01); *A61F 2002/3055* (2013.01); *A61F 2002/30579* (2013.01); *A61F 2002/30593* (2013.01); *A61F 2002/30622* (2013.01); *A61F 2002/30769* (2013.01); *A61F 2002/30795* (2013.01); *A61F 2002/3085* (2013.01); *A61F 2002/30919* (2013.01); *A61F 2002/30995* (2013.01); *A61F 2002/4627* (2013.01); *A61F 2002/4632* (2013.01)

(58) Field of Classification Search
CPC ........ A61F 2/30749; A61F 2002/30579; A61F 2/30; A61F 2002/4627; A61F 2/44; A61B 17/1757; A61B 17/7055; A61B 17/7002; A61B 2017/564
See application file for complete search history.

(56) References Cited

U.S. PATENT DOCUMENTS

| | | | | |
|---|---|---|---|---|
| 9,554,909 B2 * | 1/2017 | Donner | .............. | A61B 17/7055 |
| 9,788,862 B2 * | 10/2017 | Mootien | ........... | A61B 17/7091 |

(Continued)

*Primary Examiner* — Eduardo C Robert
*Assistant Examiner* — Holly Joanna Lane

(57) ABSTRACT

Bone anchor implants, assemblies, systems, instruments, and methods thereof. The bone anchors may be threaded or non-threaded, adjustable or expandable, stackable, or otherwise configured to promote fixation of the sacroiliac joint. The bone anchors may be used independently or may be configured to integrate with long rod constructs, for example, with a tulip or other suitable attachment interface, to fuse the sacroiliac joint.

8 Claims, 50 Drawing Sheets

(56)　　　　　References Cited

U.S. PATENT DOCUMENTS

| 9,936,983 B2 * | 4/2018 | Mesiwala | A61B 17/846 |
|---|---|---|---|
| 10,675,064 B2 * | 6/2020 | Fening | A61B 17/7216 |
| 11,291,485 B2 * | 4/2022 | Mauldin | A61B 17/84 |
| 11,357,549 B2 * | 6/2022 | Kiester | A61B 17/7023 |
| 2006/0047282 A1 * | 3/2006 | Gordon | A61B 17/7016 |
| | | | 606/907 |
| 2012/0191191 A1 * | 7/2012 | Trieu | A61B 17/864 |
| | | | 623/17.11 |
| 2013/0158609 A1 * | 6/2013 | Mikhail | A61B 17/846 |
| | | | 606/305 |
| 2017/0100174 A1 * | 4/2017 | Mishra | A61B 17/746 |

* cited by examiner

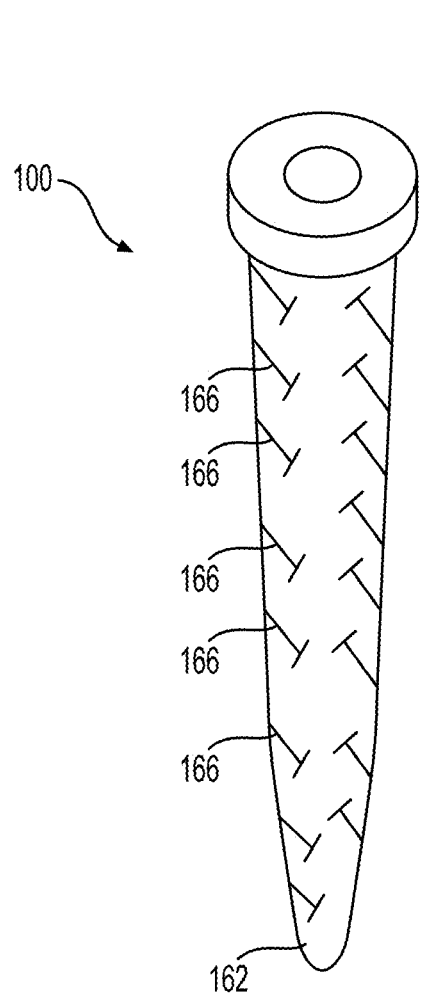
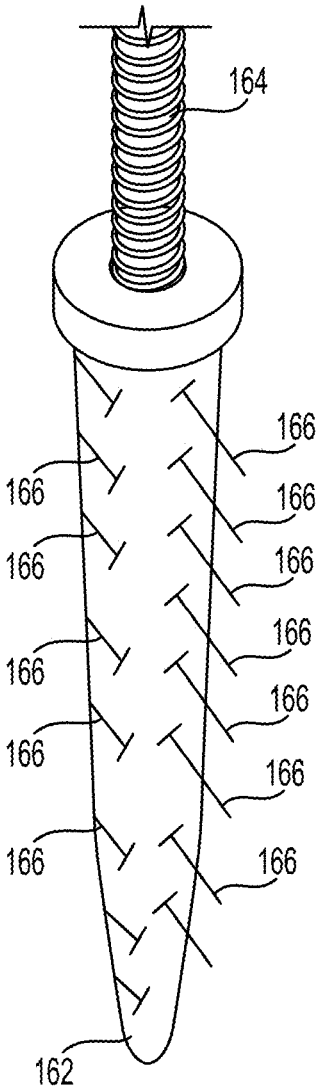
FIG. 6A          FIG. 6B

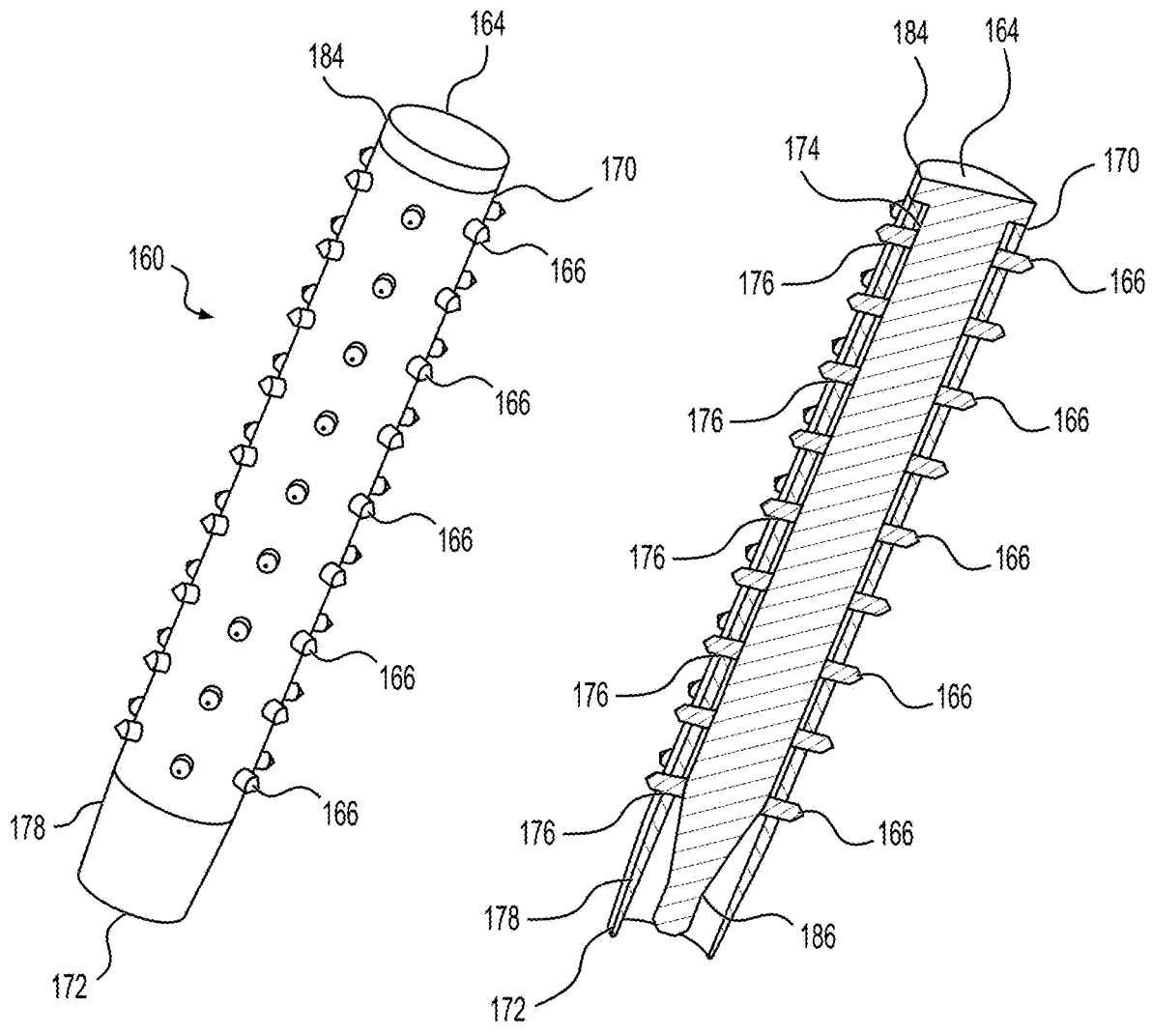
FIG. 6G        FIG. 6H

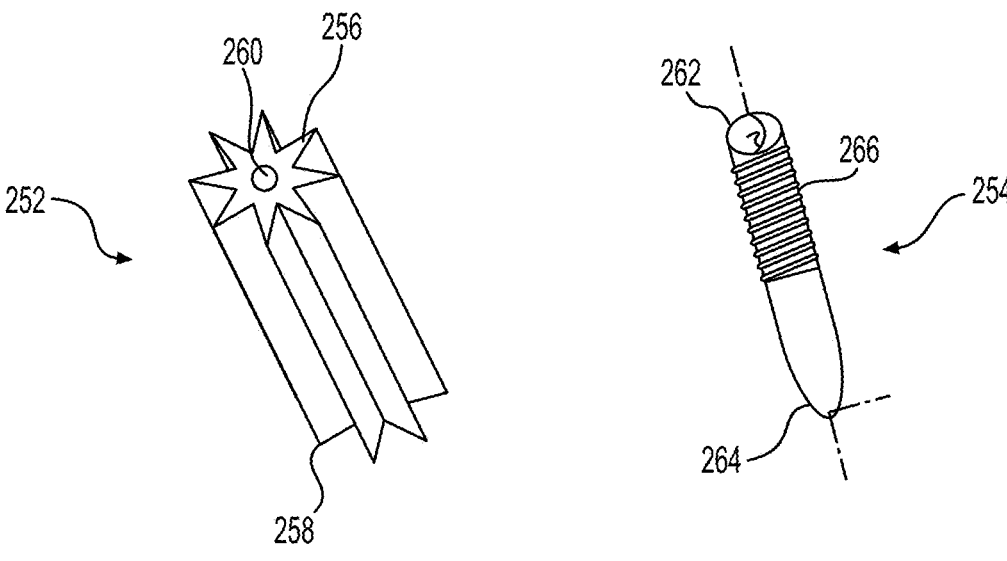
FIG. 10A
FIG. 10B
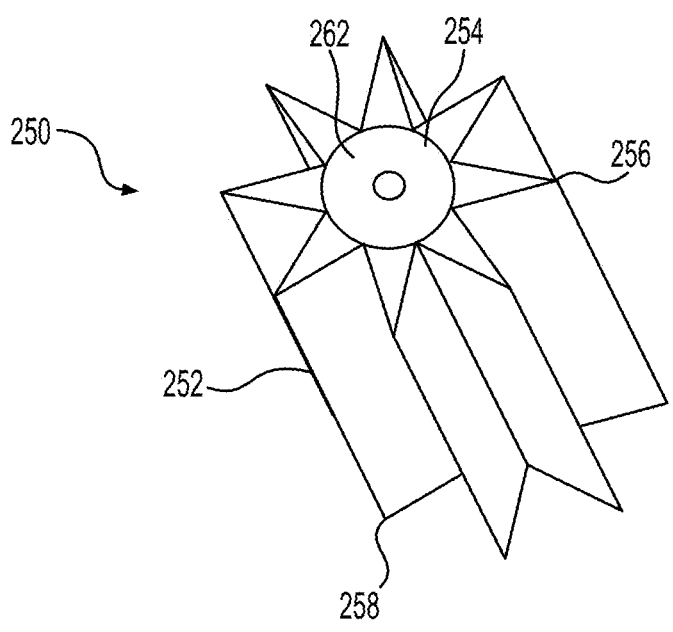
FIG. 10C

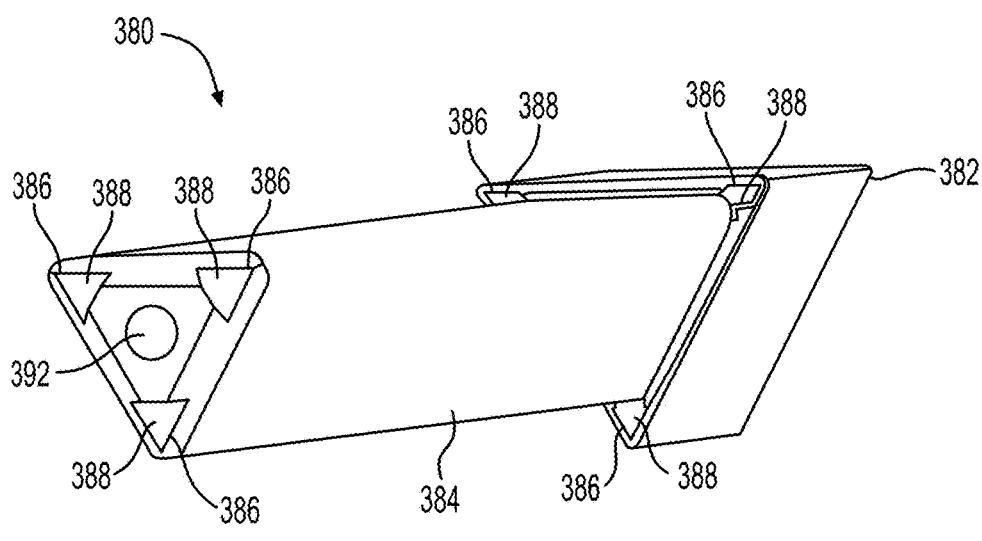
FIG. 17A
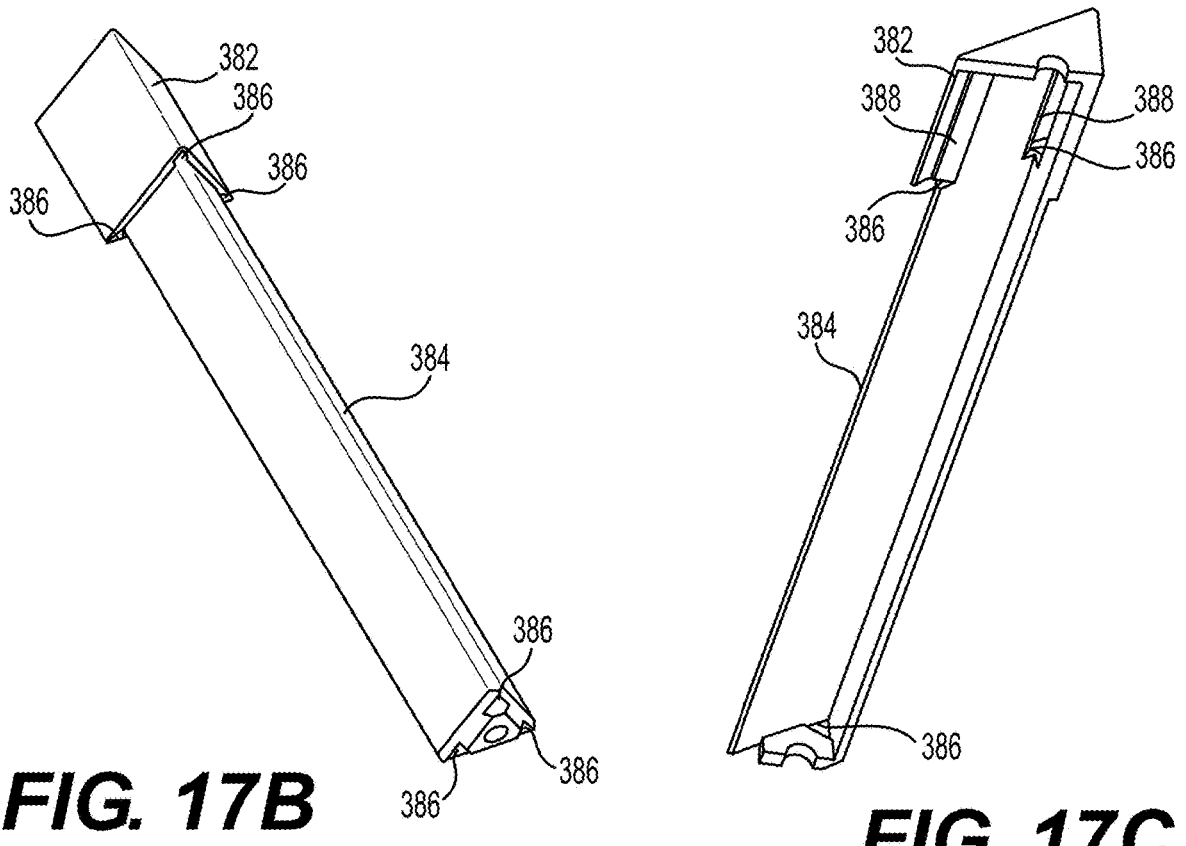
FIG. 17B
FIG. 17C

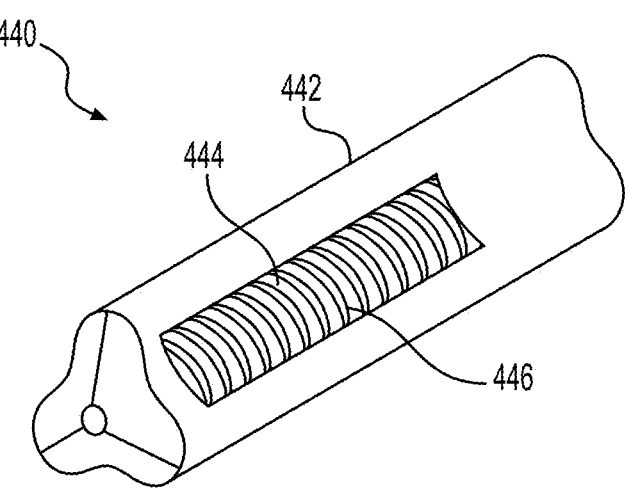
FIG. 20A
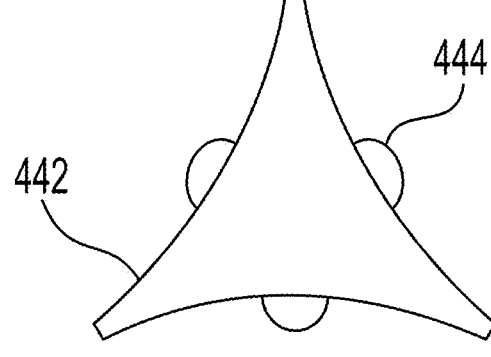
FIG. 20B
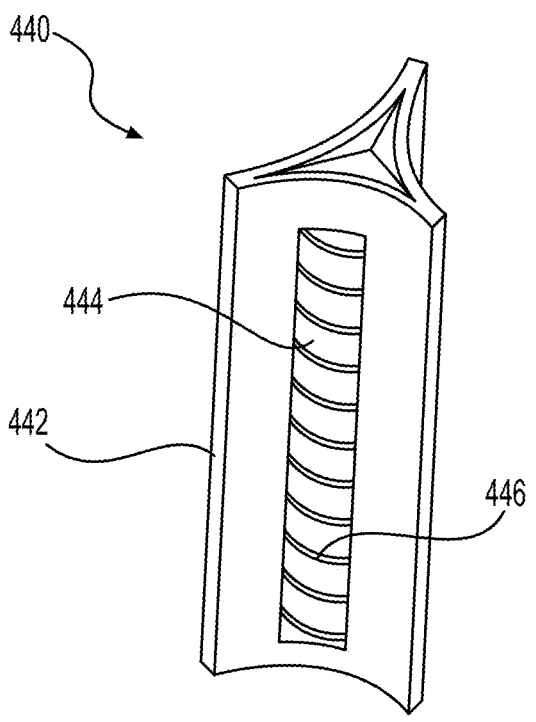
FIG. 20C
FIG. 20D

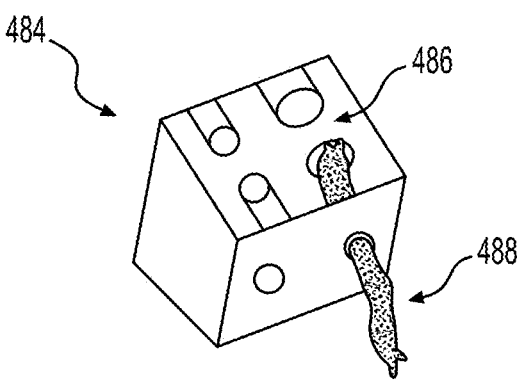
FIG. 22B
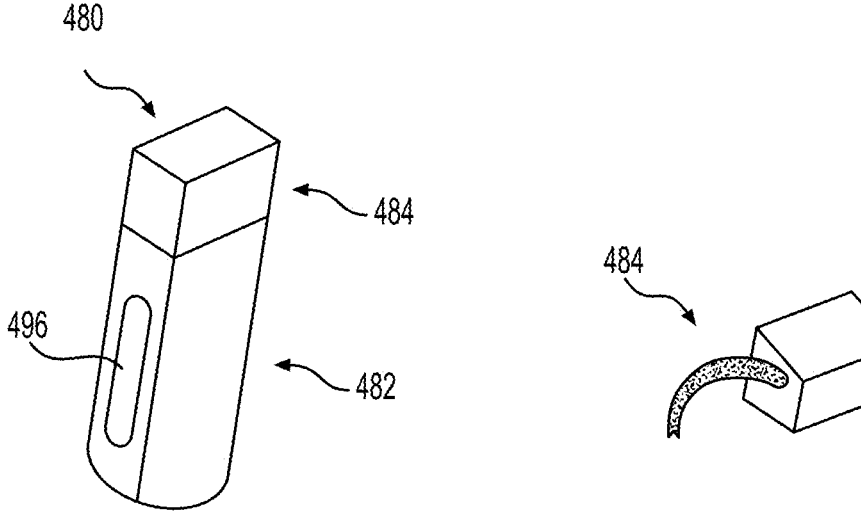
FIG. 22A
FIG. 22C
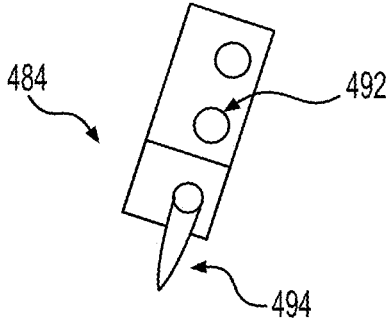
FIG. 22D

SACROILIAC JOINT FIXATION

CROSS REFERENCE TO RELATED APPLICATIONS

This application is a continuation application of U.S. patent application Ser. No. 18/060,607 filed on Dec. 1, 2022, which is incorporated in its entirety herein.

FIELD OF THE INVENTION

The present disclosure relates to surgical devices, and more particularly, to anchors, systems, and methods for fixating constructs to the pelvis.

BACKGROUND OF THE INVENTION

There are two common techniques for fixating long constructs to the pelvis: traditional sacral-alar-iliac (SAI) devices and iliac devices. Both types of fixation are placed as the anchor of a pedicle screw construct and may be used in longer deformity cases to provide additional stability. Current uses include long constructs, as well as high-grade spondylolisthesis, unstable sacral fractures, and others. Each of these require the additional support that SAI and iliac screws provide to ensure a secure lumbosacral foundation that can withstand the forces acting on constructs at the L5/S1 junction.

While SAI and iliac screws are used to support these thoraco-lumbar or longer constructs, SAI screws have been shown to also aid in reducing sacroiliac joint (SIJ) pain by limiting range of motion (ROM). Patients exhibiting SIJ pain and requiring sacro-pelvic fixation may benefit from a screw that can achieve SIJ fusion because patients that receive SIJ fixation receive revision surgery 30.8% of the time compared to only 5.7% of patients that receive SIJ fusion. The revisions may be due to loosening of the screws, which lead to the reoccurrence of SIJ pain. There currently exists a need to improve fixation and/or fusion of the SIJ, while having the capabilities to integrate with long constructs.

SUMMARY OF THE INVENTION

To meet this and other needs, anchors, implants, assemblies, systems, instruments, and methods are provided. In particular, the sacroiliac joint may be fixated or fused via a threaded or non-threaded anchor that may be used independently or may mount rigidly to a fixating rod or rigid connector. These implants may be used in open and percutaneous approaches to the posterior spine and may be compatible with robotic and/or navigation systems.

According to one embodiment, a sacroiliac implant system includes a bone fastener, such as a screw, with a tulip head. The tulip head is configured to receive a spinal rod. The spinal rod may be an anti-slip rod, for example, with a necked down section configured to prevent slip. In another embodiment, the spinal rod includes an articulating rod having a plurality rod sections that connect at one or more articulating joints. In yet another embodiment, the spinal rod is a locking telescoping rod configured to help in providing an optimal anatomical fit.

According to one embodiment, a sacroiliac joint fixation implant includes an outer sleeve and an inner sleeve extending along a central longitudinal axis, a clamp, and a tightening bolt. The outer sleeve defines a central channel for receiving the inner sleeve. The inner sleeve defines an opening configured for receiving a spinal rod. The inner sleeve includes an inner tapered section around the opening. The clamp is receivable through the inner sleeve. The clamp has a clasp configured for receiving the spinal rod. The tightening bolt is coupled to the clamp. As the tightening bolt is rotated, the clamp is drawn back proximally into the tightening bolt, and the clasp is retracted into the tapered section, thereby locking the spinal rod to the implant.

According to one embodiment, a method for stabilizing a sacroiliac joint includes one or more of the following steps in any suitable order: (1) positioning a telescoping implant across a sacroiliac joint from lateral to medial; (2) adjusting the length of the telescoping implant; (3) inserting a spinal rod into an opening in the telescoping implant; and (4) tightening a bolt in the telescoping implant to secure the spinal rod and apply a compressive force across the sacroiliac joint. The telescoping implant may be installed with a robotic and navigation system.

According to one embodiment, a sacroiliac implant includes a plate and S2-alar-iliac (S2AI) style tulip integrated with fixation. For example, the plate may retain a tulip configured to receive a spinal rod. The plate may define one or more trajectory aligning hole(s) for receiving one or more bone fasteners to secure the sacral-alar-iliac or sacro-iliac joint.

According to one embodiment, a sacroiliac implant is an expandable bone anchor. The expandable anchor may include a screw body, an expandable collar, a threaded cap, and a slip ring. The anchor may be inserted laterally and then the collar is configured to expand around the middle by rotation of the threaded cap.

According to one embodiment, an expandable sacroiliac implant includes a hollow dowel extending along a central longitudinal axis, a plurality of moveable pins, and a central expansion key. The dowel defines a center channel in fluid communication with a plurality of openings. Each pin has an inner end receivable in the central channel and an outer end configured to eject from the openings in the dowel. The central expansion key is sized and dimensioned to fit within the center channel. Movement of the central expansion key, for example, rotationally or axially, causes the pins to extend radially outward from the dowel.

According to one embodiment, a method for stabilizing a sacroiliac joint includes one or more of the following step in any suitable order: (1) posteriorly accessing a spine of a patient; (2) inserting an expandable anchor into the sacroiliac joint, the anchor having a body with a plurality of expandable pins; and (3) inserting an expansion key through the body of the anchor to deploy the pins, thereby creating a strong press-fit in the sacroiliac joint. The expansion key may be rotated or axially translated to deploy the pins. The sacroiliac joint may be accessed with a robotic and navigational system.

According to one embodiment, a sacroiliac implant includes a non-threaded, non-cylindrical pin configured to secure the sacroiliac joint. The pin may be a triangular pin with sharp edges, serrated edges, or soft corners. The faces of the pin may be planar or curved, for example, concavely to define cutting wings or fins along the edges of the implant.

According to one embodiment, a sacroiliac implant includes an expandable implant with a star-shaped body configured to expand with the introduction and impaction of a central dowel. The star-shaped body may have linkages hingedly connected together, which expand in diameter and move radially outward.

According to one embodiment, a sacroiliac implant includes an expandable distal tip. The implant may include a polygonal pin inserted across the sacroiliac joint for fixation and an internal mechanism is rotatable to allow a cam, or other mechanism, to expand several distal fixation arms.

According to one embodiment, an expandable sacroiliac implant includes an outer sleeve extending along a central longitudinal axis, a plurality of moveable teeth, and an inner shaft. The outer sleeve defines a center channel in fluid communication with a plurality of openings. Each tooth has an inner end receivable in the central channel and an outer end configured to eject from the openings in the outer sleeve. The inner shaft is sized and dimensioned to fit within the center channel. Movement of the inner shaft causes the teeth to extend radially outward from the outer sleeve. The teeth may be attached to the inner shaft. Alternatively, the teeth may be replaced with independent fins.

According to one embodiment, a buildable implant includes a first stackable section having a female mating portion and a male mating portion, and a second stackable section having a female mating portion and a male mating portion. The male mating portion of the first or second stackable section is receivable in the female mating portion of the other first or second stackable section to interlock the first and second stackable sections together. The first and second stackable sections are assembled in situ to form a rigid construct configured to secure a sacroiliac joint.

According to one embodiment, the sacroiliac implant is a pin configured to be auto-packed with autograft. The pin may include one or more internal cutting notches configured to shave bone during insertion and internally pack the implant to promote fusion. For example, the pin may be a triangular pin with cutting notches disposed at each bottom corner of a distal tip and each bottom corner of a proximal sealed cap.

According to one embodiment, the sacroiliac implant includes a tulip head and a threaded screw with overlapping graft windows. The distal end of the screw may define a bone packing tooth and a large cannulation to gather bone. The screw may be implanted with a robotic and/or navigation system such that a full cannulation through the entire implant is not necessary.

According to one embodiment, the sacroiliac implant includes a tulip head and a threaded screw composed of a 3D printed mixed density material. For example, the screw may have a solid core with an outer threaded surface having a textured and/or porous composition for boney ingrowth.

According to one embodiment, the sacroiliac implant includes a triangular pin with an integrated internal screw therein. The internal screw may be rotated to drive the triangular pin through the bone and into a final location to secure the sacroiliac joint. Alternatively, the screw may project from a distal end of the triangular pin.

According to one embodiment, the sacroiliac implant includes a transfixing spacer configured to cross the sacroiliac joint and a plate or mounting block for securing the implant. The plate or mounted block may be secured with bone screws, nitinol wire anchors, or other deployable anchors.

According to one embodiment, the sacroiliac implant is a spiral nail screw with one or more spiral cutting flutes and a pointed distal tip. The spiral cutting flutes may be impacted and rotated through the sacroiliac joint for fixation.

According to one embodiment, the sacroiliac implant is a threaded screw with one or more cheese grater-like serrations. These serrations may be positioned between a standard thread pitch to allow automatic gathering of bone material and internal collection in the screw body.

According to one embodiment, the sacroiliac implant is a threaded screw with expandable threads. The individual thread sections may be expanded with an internal plunger or a rotating cam, for example.

According to one embodiment, the sacroiliac implant is a threaded screw with screw threads that positively engage the bone upon insertion to improve resistance to lateral forces. The screw threads may help to provide migration resistance of the screw.

According to one embodiment, an instrument may be used to create a pilot hole for the sacroiliac implant. For example, an oscillating broach may include an outer sleeve, such as a triangular sleeve, that houses one or more oscillating broach blades with teeth at the end configured to cut bone. The pilot hole may lessen the impaction forces needed to install the pin implant.

Also provided are kits including anchors or implants of varying types and sizes, bone fasteners, spinal rods, k-wires, insertion tools, instruments, and other components for performing the procedure(s).

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIGS. 6A-6H show examples of an expanding pin implantable dowel;

FIGS. 10A-10H show examples of expanding geometry pins having collapsed and expanded star shapes;

FIGS. 17A-17C show a self-packing triangular pin with internal cutting notches configured to shave bone during insertion according to one embodiment;

FIGS. 20A-20F show examples of implants with a triangular pin and integrated internal screw;

FIGS. 22A-22D show examples of a fixation block with a stabilization mount;

DETAILED DESCRIPTION OF THE INVENTION

Figure 1A:
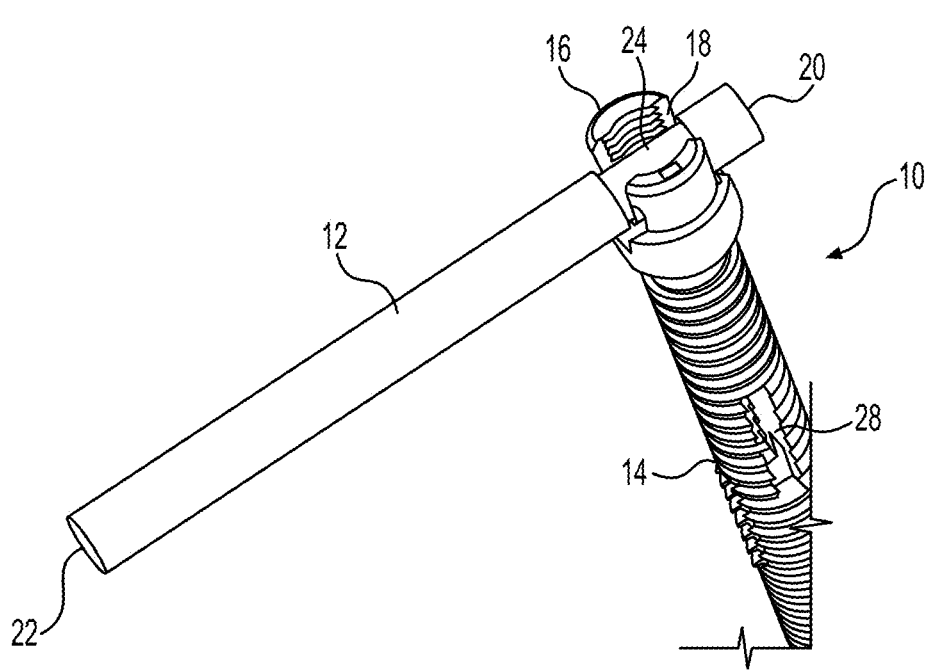
FIGS. 1A-1D show an anti-slip rod receivable in a tulip assembly for rigid fixation to a sacroiliac joint according to one embodiment.

Bone anchors, assemblies, and systems are configured to fixate and/or fuse the sacroiliac joint. The anchors may be threaded or non-threaded, adjustable or expandable, stackable, or otherwise configured to promote bone fixation. The anchors may be pre-assembled or assembled in situ. The bone anchors may be used independently or may include the capability to integrate with long rod constructs, for example, with a tulip or other suitable attachment interface, to prophylactically fuse the sacroiliac joint. In some embodiments, the rod constructs may include articulating or telescoping rods and/or anti-slip rods.

These implants may be used in open and percutaneous approaches to the posterior spine and may be compatible with robotic, imaging, and/or navigation systems. Further details of robotic and/or navigational systems can be found, for example, in U.S. Pat. Nos. 10,675,094, 9,782,229, and U.S. Patent Publication No. 2017/0239007, which are incorporated herein by reference in their entireties for all purposes.

Special instruments, such as an ultrasonic oscillating broach, may be used to prepare the bone for placement of the bone anchor. The ultrasonic bone cutting bit may be helpful to create a shaped pilot hole, similar to that of the implant, thereby requiring less impaction of the bone implant.

The implants or components thereof may be comprised of titanium, stainless steel, cobalt chrome, cobalt-chrome-molybdenum, tungsten carbide, carbon composite, plastic or polymer—such as polyetheretherketone (PEEK), polyethylene, ultra-high molecular weight polyethylene (UHMWPE), resorbable polylactic acid (PLA), polyglycolic acid (PGA), allograft, autograft, or combinations of such materials or any other appropriate material that has sufficient strength to be secured to and hold bone, while also having sufficient biocompatibility to be implanted into a body. Although the above list of materials includes many typical materials out of which implants may be made, it should be understood that implants comprised of any appropriate material are contemplated.

Referring now to FIGS. 1A-1D, an orthopedic fixation assembly, bone fastener assembly, or implant 10 for securing an anti-slip rod 12 is shown according to one embodiment. The implant or bone fastener assembly 10 may include a modular tulip element or tulip head 16 attachable to a bone fastener 14. The tulip head 16 is configured to receive the spinal rod 12 and a locking cap may be used to secure the spinal rod 12 in the tulip head 16. For a polyaxial bone fastener 14, tightening the locking cap may compress the rod 12 into the tulip head 16, thereby restricting motion of the bone fastener 14 and forming a rigid construct.

The tulip head 16 may include a body with arms that separate a rod slot 18. The rod slot 18 may define a U-shaped channel or rounded slot sized and configured to accept the rod 12. The inner portion arms of the tulip head 16 may have a threaded interface for engaging a threaded locking cap. The bone fastener 14 may include a bone screw, anchor, clamp, or the like configured to engage bone, such as the sacral-alar-iliac or sacroiliac joint. In the embodiment shown, the bone fastener 14 is a bone screw having a screw head and a threaded shaft extending from the screw head. The threaded shaft may define one or more longitudinal windows 28 configured to receive bone or suitable bone graft material. FIG. 1A does not show the distal end of the threaded shaft, but it may be pointed, sharpened, blunt, or otherwise configured to engage bone. Suitable bone fasteners/assemblies will be recognized by those of ordinary skill in art. Examples of bone fasteners, other implants, and rod constructs are described in more detail, for example, in U.S. Pat. No. 10,368,917, which is incorporated by reference herein in its entirety for all purposes.

Figure 1B:
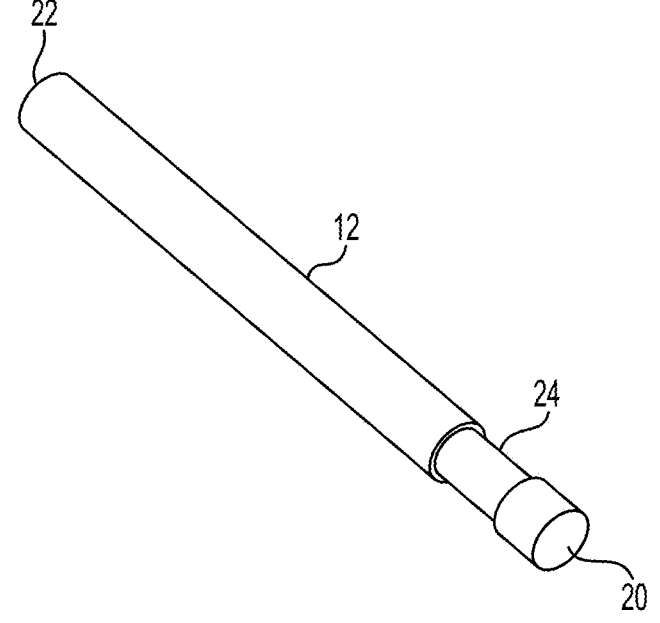
Figure 1C:
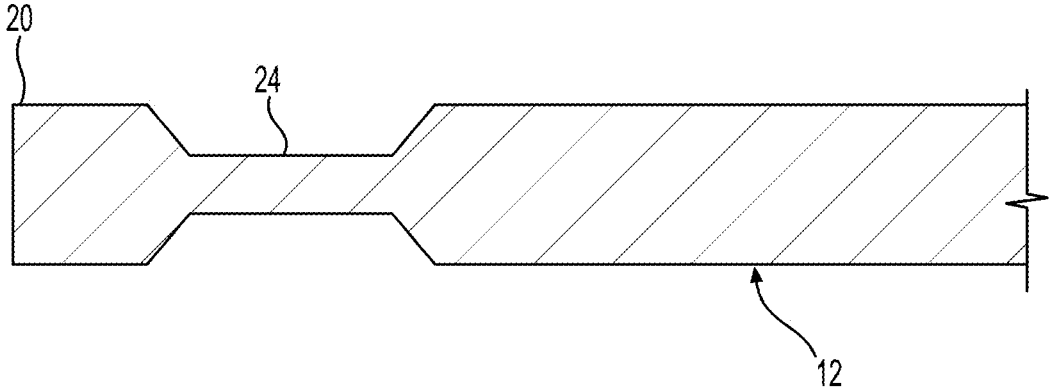

With further emphasis on FIGS. 1B-1C, the spinal rod 12 may be an anti-slip rod with a larger rod body for strength where a portion of the rod necks in to prevent slip. The rod 12 extends from a first end 20 a second end 22 along a central longitudinal axis for a given length. The rod 12 may be straight, bent, or contoured to follow the patient's anatomy. The rod 12 may have a generally cylindrical body or other suitable cross-section with a reduced diameter or necked down section 24. For example, the rod 12 may have a larger diameter section mounted to or integral with a traditional 5.5 or 6.0 type rod or necked down section 24. The necked down section 24 may generally have a length about the same as or slightly larger than the size of the rod slot 18 in the tulip 16. The edges of necked down section 24 may be squared, slanted, beveled, or the like to transition between the two diameters. The necked down section 24 may be placed into the tulip 16, but the remaining portion of the rod 12 may be larger than normal to withstand the high loads when combined with the SI joint fusing screw 10. In addition, the tolerances on the large section of the rod 12 may be increased when compared to the necked section 24 designated for tulip connection. This may produce manufacturing benefits in terms of efficiency.

Figure 1D:
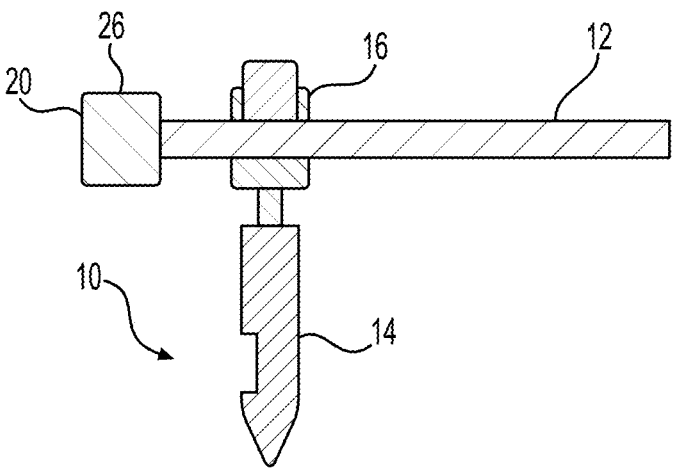

According to another embodiment shown in FIG. 1D, the anti-slip rod 12 may include an enlarged rod end 26 to prevent rod slip. In this embodiment, the rod 12 may have a standard rod diameter and at least one end 20 includes an enlarged diameter or increased cross-section. For example, free end 20 near implant 10 may be enlarged adjacent to the tulip head 16. The enlarged end 26 prevents the rod 12 from slipping out of the tulip 16.

Figure 2A:
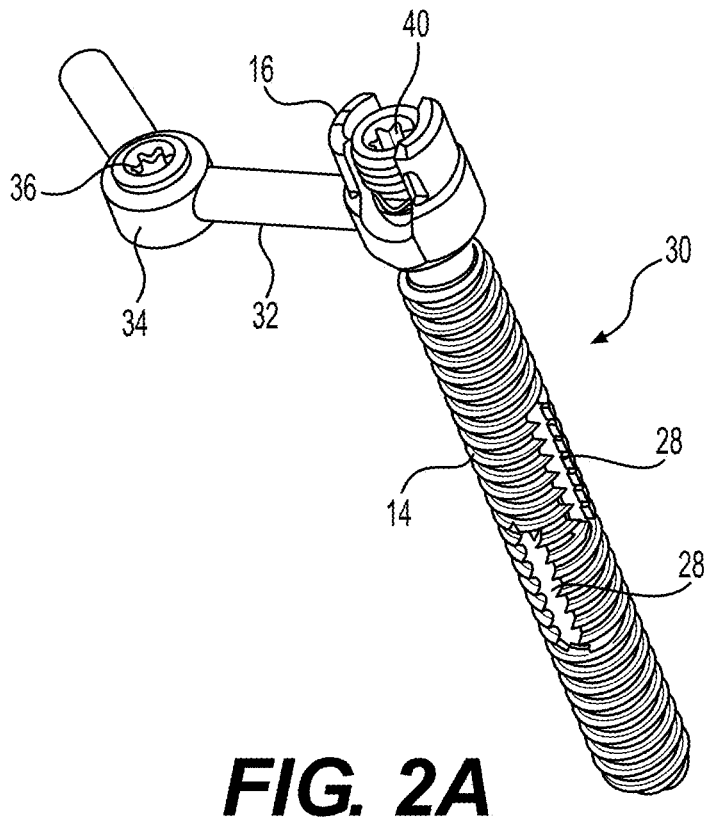
FIGS. 2A-2D show examples of articulating and/or telescoping rods for attachment to a sacroiliac joint fixating screw.
Figure 2B:
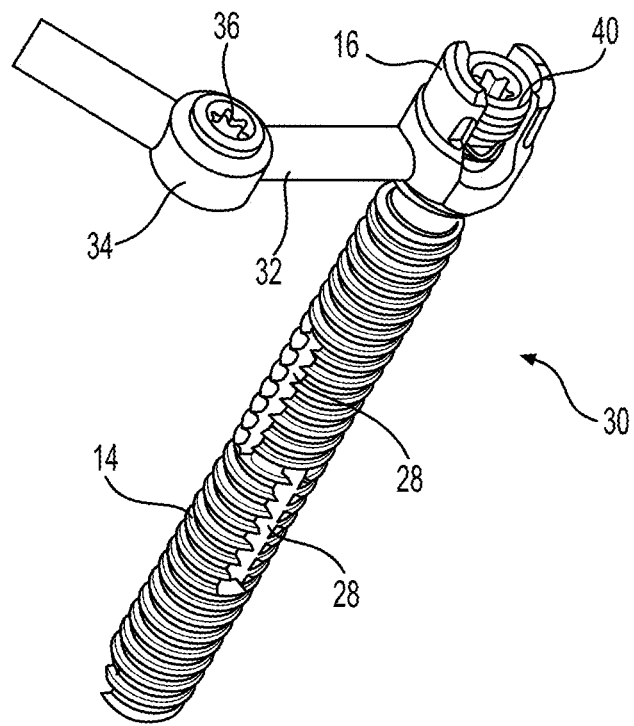
Figures 2C, 2D:
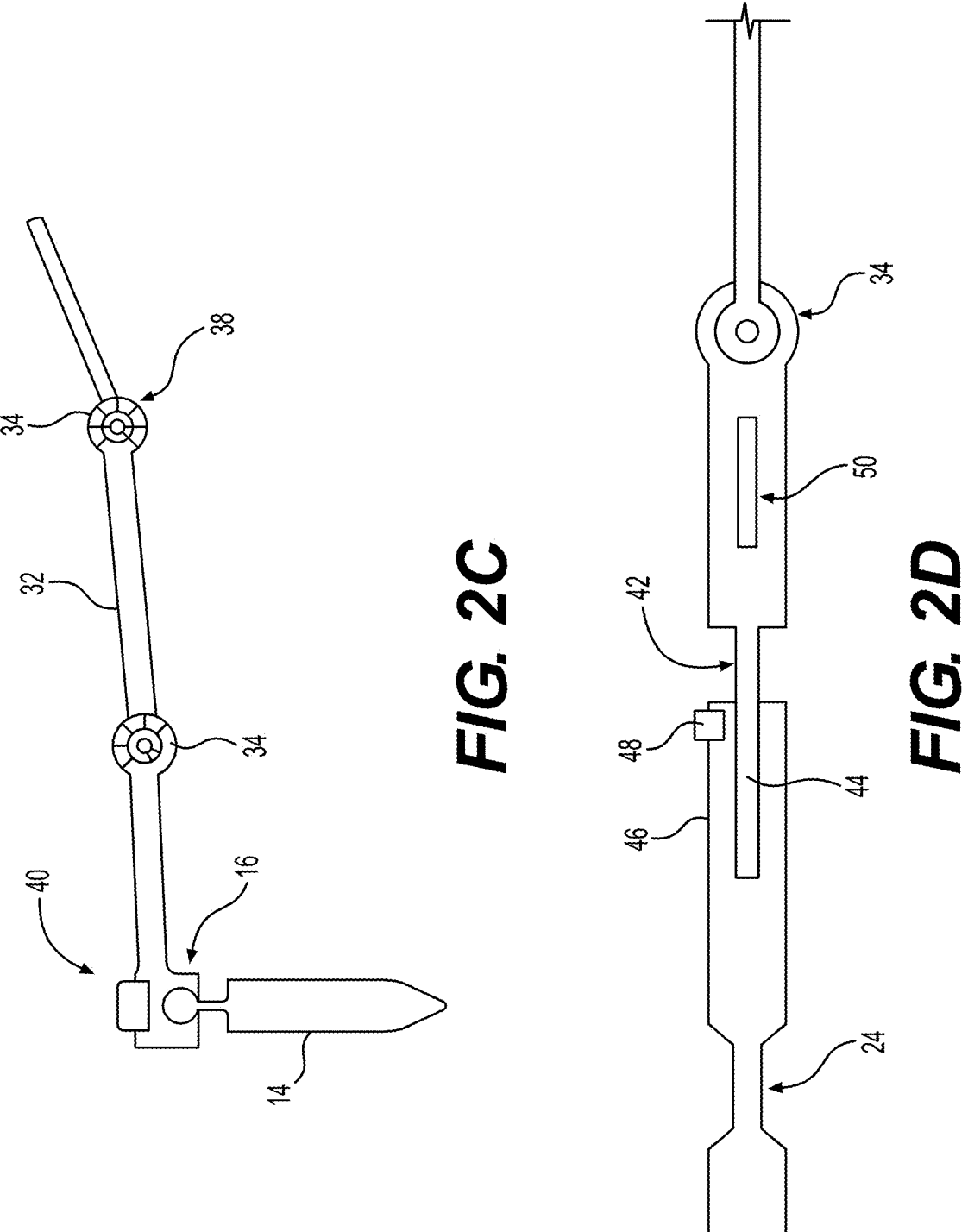

Turning now to FIGS. 2A-2D, examples of maneuverable orthopedic fixation assemblies, bone fastener assemblies, or implants 30 are shown. FIGS. 2A-2C depict an articulating rod 32 coupled to the bone fastener assembly 30. FIG. 2D shows a telescoping rod 42 with a necked section 24 attachable to a tulip head 16. The articulating rod 32 may or may not have an integrated tulip 16 for attachment to the SIJ fixating screw 14. In the embodiment shown, the articulating rod 32 has a fixed tulip connection. The articulating rod 32 may include a plurality of segments or rod sections that connect at one or more central articulation components, linkages, or articulating joints 34. Each articulating joint 34 may be lockable, for example, via a threaded interlocking toothed connection. A threaded set screw 36, lockable with a standard driver, may be configured to secure the position of the connected sections of the articulatable rod 32. The articulating joints 34 may be locked into specific angles, thereby providing the desired positioning of the rod 32.

FIG. 2C shows the articulating rod 32 with one or more integrated strain gauges 38 that can help monitor rod strain during deformity correction. The rod 32 may be integral with the tulip head 16 and an integrated locking cap 40 may be used to secure the tulip head 16 to the bone fastener 14. In this embodiment, three rod sections are connected by two articulatable joints 34, but any suitable number and configuration of rod section and joints may be selected. The strain gauge 38 may be connectable to a robotic and/or navigation system during the deformity correction manipulations. In one embodiment, the strain gauge 38 is not powered or wireless so the gauge does not operate post op. The benefits are a simplified and non-powered implant, but with the ability to monitor local rod strain during forceful correction maneuvers.

FIG. 2D shows an example of a locking telescoping rod 42 to help in providing an optimal anatomic fit. The telescoping rod 42 may have an inner rod 44 receivable in an outer rod 46, which slides in and out, making the overall rod adjustable in length. The two sections of rod 44, 46 may have slightly different diameters, allowing the narrower rod 42 to slide snugly inside the wider rod 44. The length and position of rods 44, 46 may be locked in place via a locking button 48 or other suitable mechanism. It will be appreciated that the configuration of the rods 44, 46 may be reversed or otherwise configured. A sensor pack 50 may be used to provide strain information to the robotic and/or navigation system. The telescoping rod 42 may also include one or more articulating joints 34. The telescoping rod 42 may attach to the SIJ fastener 14 via a tulip 16 attachable to the necked in area 24 as described for FIGS. 1A-1C.

Figure 3A:
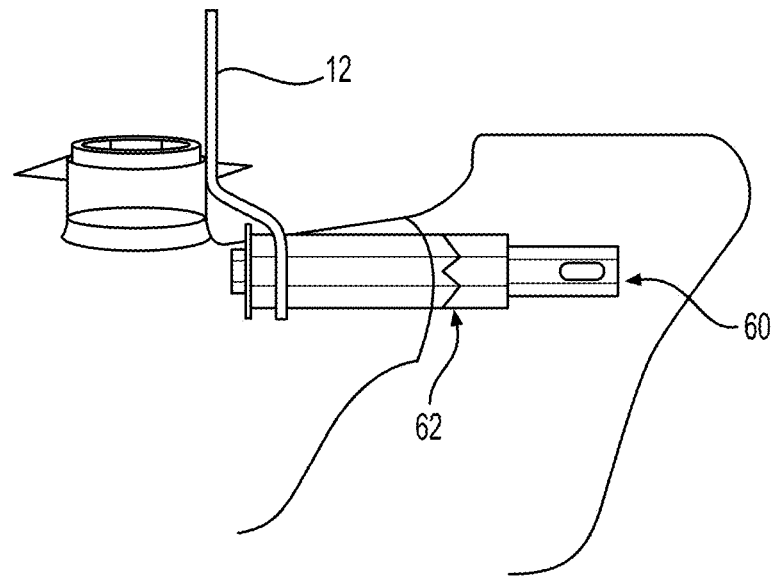
FIGS. 3A-3E show a lateral to medial telescoping pin with rod gripping capability according to one embodiment.

Turning now to FIGS. 3A-3E, a telescoping fixation dowel or pin 60 with rod gripping capability is shown according to one embodiment. The sacroiliac joint fixation implant 60 may be configured to cross the sacroiliac joint from a lateral to medial approach. The implant 60 may be placed with the assistance of a robotic and/or navigation system in such a way as to line up with spinal rod 12. For example, the implant 60 may be aligned with a bare rod section from a superior screw and rod construct. In this way, the implant 60 may fixate to spinal rod 12 without the use of a traditional tulip. As best seen in FIG. 3A, the lateral to medial telescoping pin 60 may include a split joint 62 to obtain compression and threads that lock from the side to reduce load.

Figure 3B:
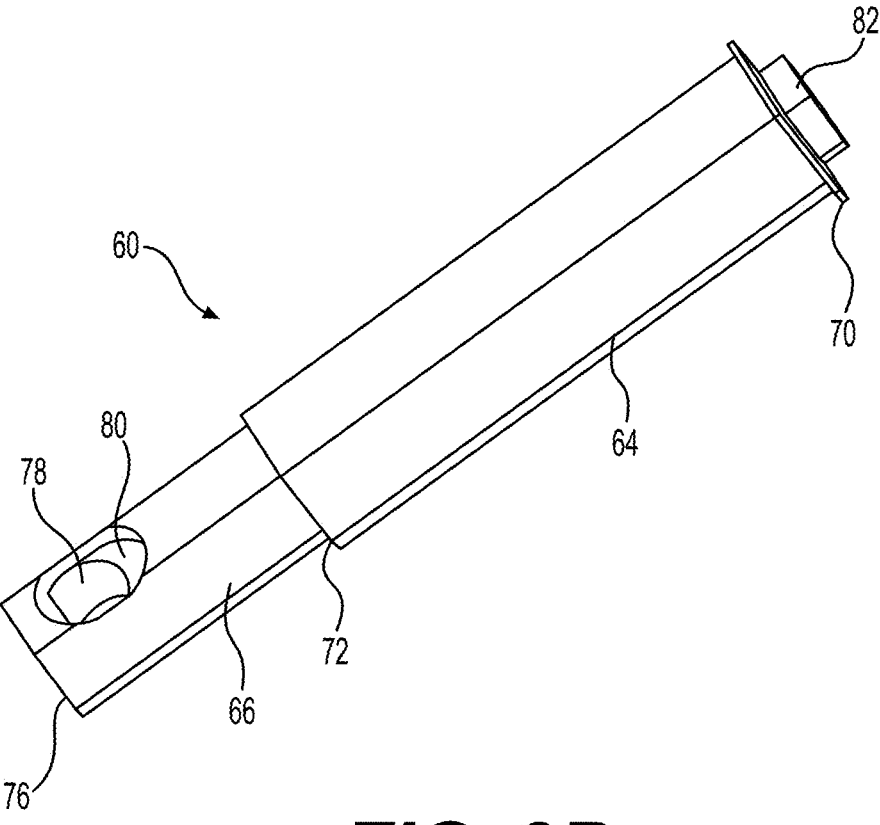

With further emphasis on the perspective view in FIG. 3B, the telescoping pin 60 includes an outer sleeve 64 and an inner sleeve 66 aligned along a central longitudinal axis. The outer sleeve 64 extends from a proximal end 70 to a distal end 72 and defines a central channel therethrough. The proximal end 70 may include an enlarged lip configured to abut the bone of the ilium of the patient. A proximal end 74 of the inner sleeve 66 is receivable inside the outer sleeve 64 and a distal end 76 of the inner sleeve 66 defines an opening 78 configured to receive the spinal rod 12 therethrough. The outer and inner sleeves 64, 66 may have hexagonal sections that telescope with respect to one another. Although hexagonal bodies are shown, it will be appreciated that the outer and inner sleeves 64, 66 may have other suitable mating cross-sections. By telescoping with one another, the overall length of the implant 60 may be adjusted to fit the anatomy of the patient.

Figures 3C, 3D:
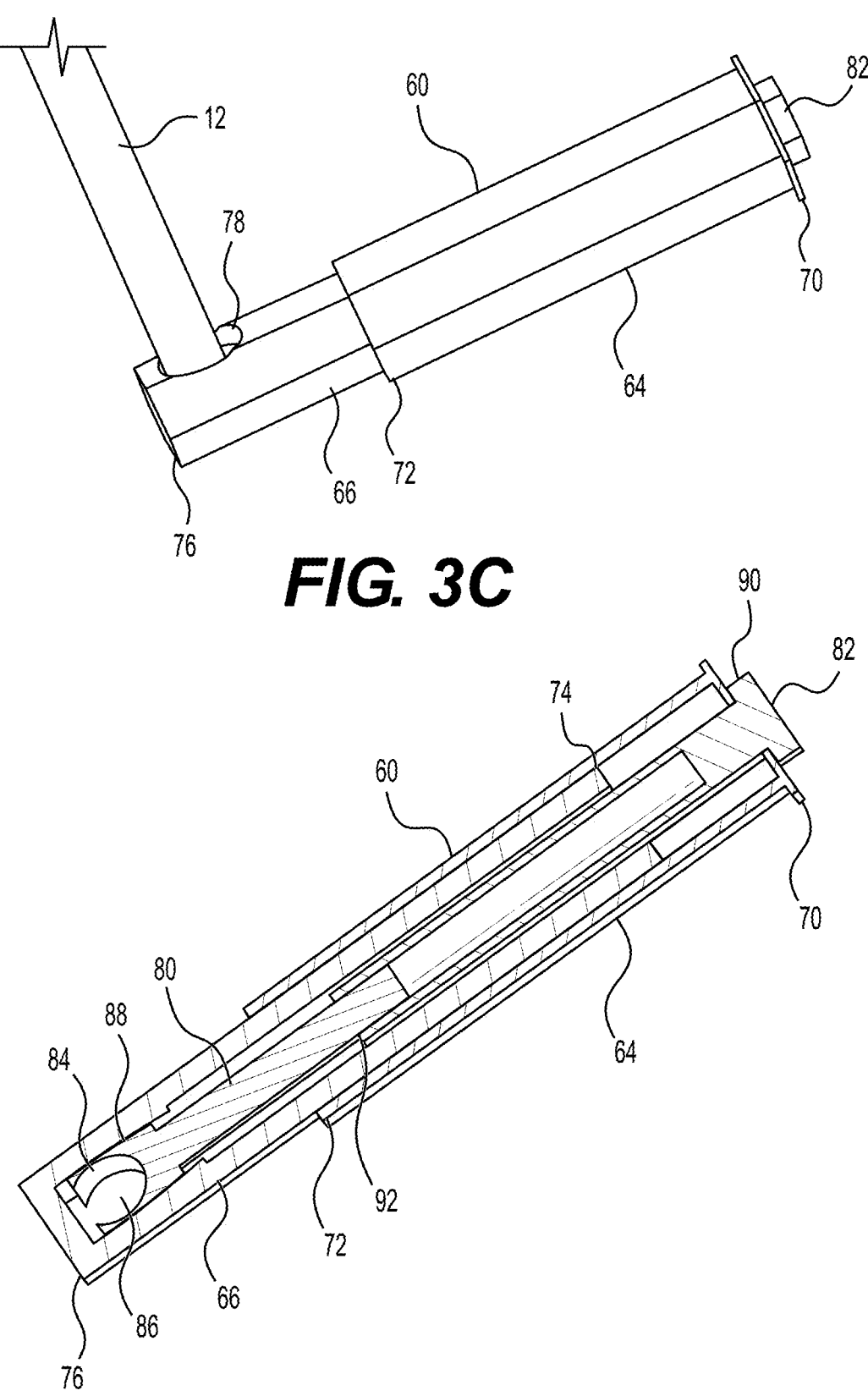
Figure 3E:
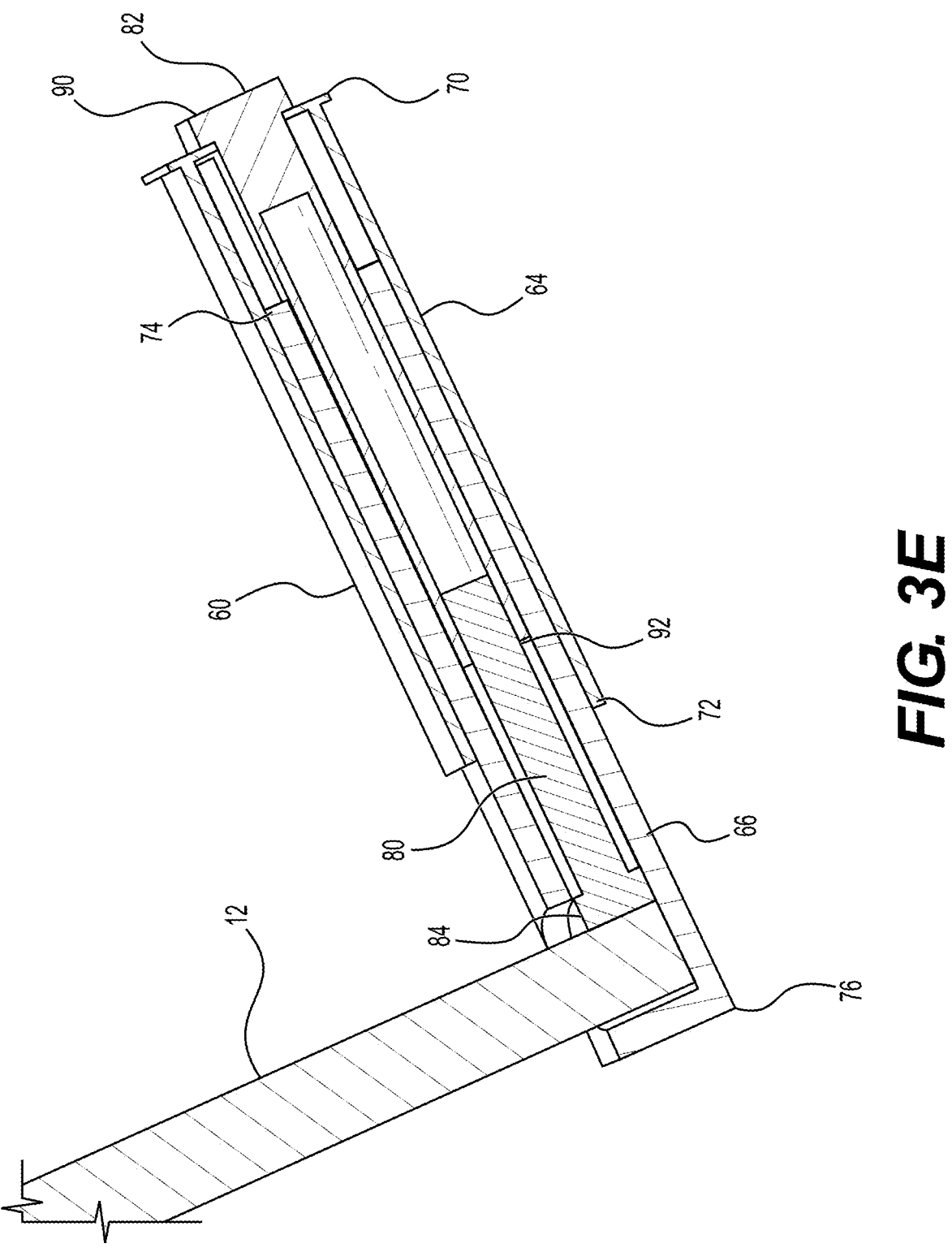

FIG. 3C shows the spinal rod 12 attached to the telescoping pin 60. The rod 12, such as a 5.5 spinal rod, is positionable through opening 78 in the inner sleeve 66. The implant 60 may lock to the spinal rod 12 with an internal thread and locking component within the implant body 60. For example, as best seen in the cross-sectional view of implant 60 in FIG. 3D, the spinal rod 12 may be locked to the inner sleeve 66 via a locking assembly including a clamp 80 and a tightening bolt 82.

The clamp 80 may include an elongate body receivable through the inner sleeve 66. A proximal end of the clamp 80 includes a locking end or clasp 84, which may define an opening 86 for receiving the spinal rod 12. The locking end or clasp 84 may have a C-shaped or U-shaped body which defines a rounded or circular opening 86 configured to surround the body of the rod 12. In one embodiment, the clamp 80 cannot rotate and is retracted into a narrowed or tapered section 88 of the implant 60 causing the locking end 84 to grab and secure the rod 12 therein. The inner tapered section 88 may be widest at a distal end 76 of the inner sleeve 55 and internally narrows proximally.

The tightening bolt 82 is at least partially cannulated, for example, with a blind hole. The tightening bolt 82 includes a head portion 90, which abuts the proximal end 70 of the outer sleeve 64, and a distal end 92 configured to receive the proximal end of the elongate portion of the clamp 80. There may be a threaded engagement between the tightening bolt 82 and the clamp 80 and/or the tightening bolt 82 and the inner sleeve 66. As best seen in the cross-sectional view of FIG. 3E, the spinal rod 12 is positionable through opening 78 in the inner sleeve 80 and into the opening 86 of clasp 84. As the bolt 82 is rotated and tightened, the clamp 80 is drawn back proximally into the tightening bolt 82. As the clamp 80 is drawn into the tapered section 88, the clasp 84 tightens around the rod 12, thereby locking the rod 12 into position. Continued tightening of the bolt 82 begins to compress the implant 60 causing the proximal lip 70 to provide compressive force across the sacroiliac joint. Alternatively, compression of the sacroiliac joint may be achieved after final tightening via a secondary compression thread. Implant 60 removes the need for having a tulip and helps to address the difficulty that comes with final tightening of a tulip/implant from such an angle in the posterior position. One or more implants 60 may also be used without a rod using a more traditional sacroiliac fusion technique, thereby providing the system increased versatility based on surgeon preference.

Some embodiments allow for fixation of the joint or attachment to the rod without a traditional threaded implant or tulip. Benefits may include decreased time due to simple implant impaction for implantation. Attachment of the implant to the rod without a tulip provides a low profile modified Galveston-type of approach. Benefits may include easier final tightening and the possibility for straighter rods which may reduce rod strain.

The implant may be configured to cross the sacroiliac joint from a lateral to medial approach and lock to a rod without a tulip, which has benefits in providing fixation to a longer rod and screw construct without a tulip or traditional locking cap. This may ease the process of construct construction and provides a lower profile result compared to a traditional tulip. The telescoping body of the implant also has the ability to compress the sacroiliac joint which is advantageous when attempting to promote fusion.

Turning now to FIGS. 4A-4E, examples of plate and S2-alar-iliac (S2AI) style tulip integrated with fixation are shown. Some embodiments feature thicker screw shanks and/or larger drive features than standard pedicle screws. This improved strength is positive and desirable especially when using such a screw in many instances of lumbosacral fusion.

The implant 100 may include a plate 102 with a tulip head 106 attachable to a first bone fastener 104. The plate 102 and tulip 106 may be integral and made as a one-piece section of metal for increased strength. The tulip head 106 is configured to receive a spinal rod in a rod slot 108 and a locking cap may be used to secure the spinal rod in the tulip head 106. A second bone fastener 110 is positionable through one or more openings 112 in the plate 102. The bone fasteners 104, 110 may include bone screws, anchors, clamps, or the like configured to engage bone, such as the sacral-alar-iliac or sacroiliac joint. In the embodiment shown, the first and second bone fasteners 104, 110 are bone screws having a screw head and a threaded shaft extending from the screw head. The threaded shaft may define one or more longitudinal windows 114 configured to receive bone or other bone graft material.

Figure 4A:
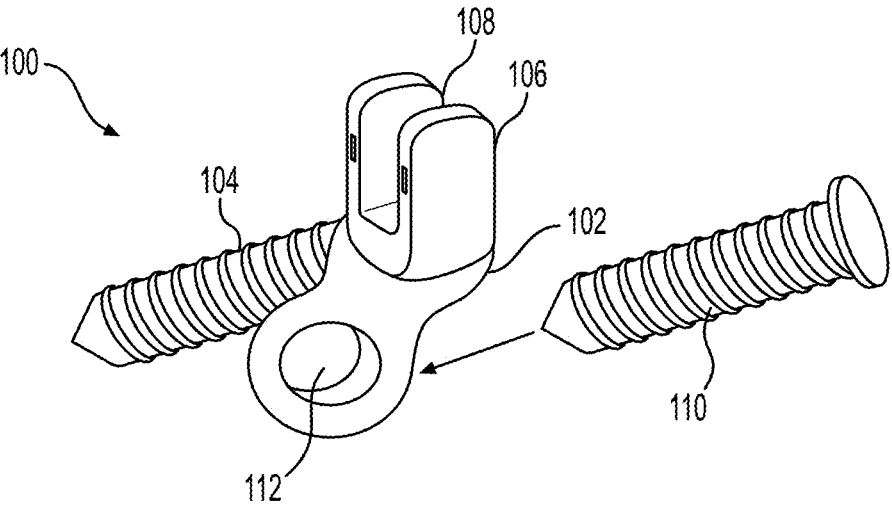
FIGS. 4A-4E show examples of plates with integrated S2-alar-ilial style tulips for increased fixation of the sacroiliac joint.
Figure 4B:
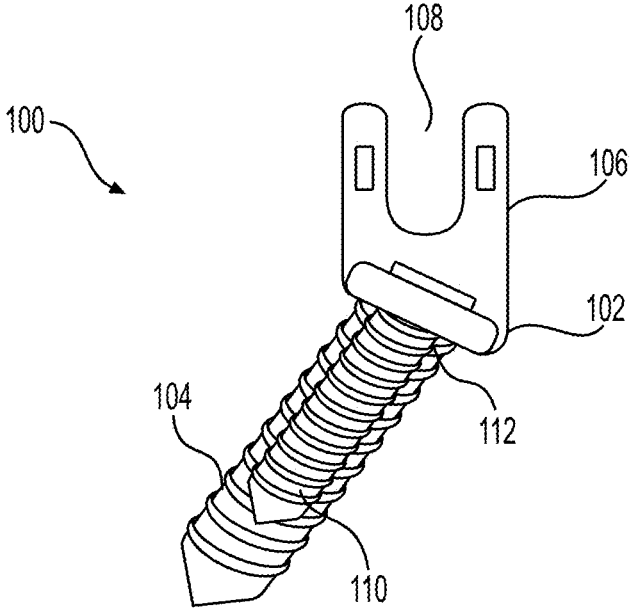

FIG. 4A shows the preferred angle screw 104 with the addition of bottom plate 102 defining trajectory aligning hole(s) 112. The second screw 110 is aligned with hole 112 for a desired trajectory into bone to secure the sacral-alar-iliac or sacroiliac joint. In FIG. 4B, the second screw 110 is implanted into the plate 102 for increased fixation of the sacroiliac joint. This provides a simple way to fixate the sacroiliac joint and attach to the spinal rod. Such additional screws may be of increased diameter or length, and may have windows 114 to be packed with bone, for example.

Figure 4C:
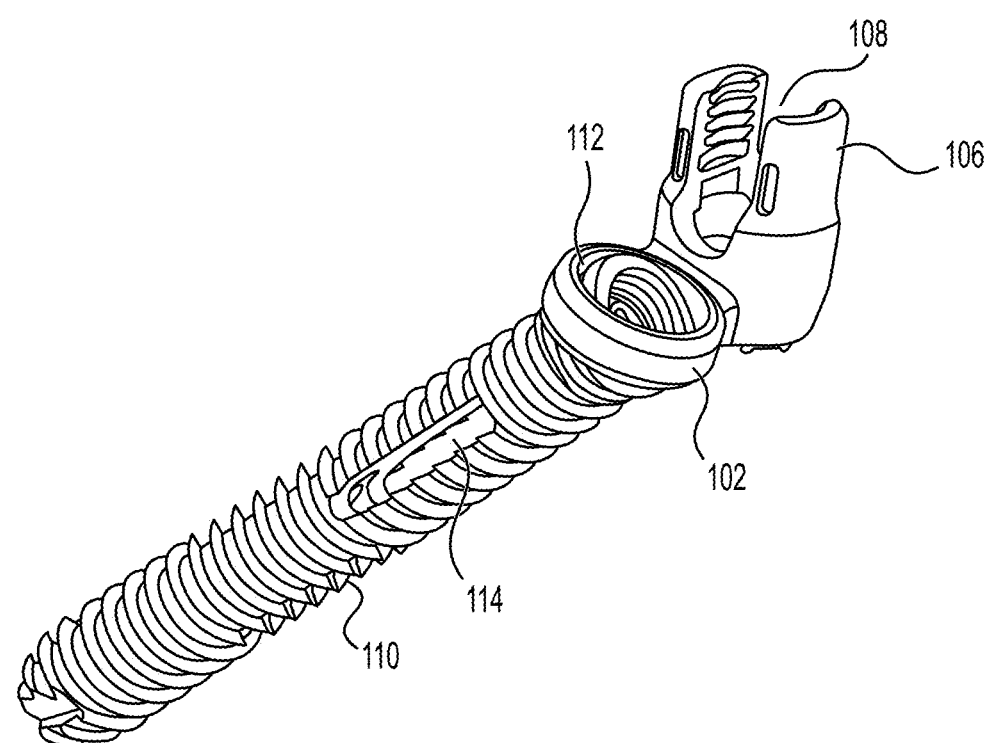
Figure 4D:
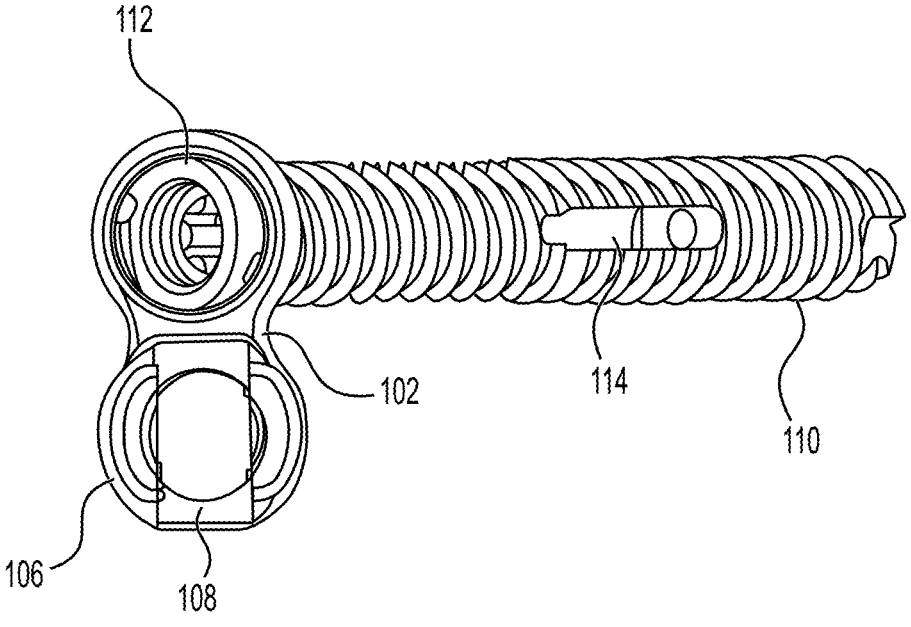

FIGS. 4C-4D depict an alternative version of implant 100 with a single screw plate 102 and integrated offset tulip 106 for retaining the spinal rod. The head of bone fastener 110 is retained in opening 112 through plate 102. A portion of the plate 102 may form a ring around the head of the fastener 110, thereby securing the fastener 110 therein. The tulip 106 is offset relative to the opening 112. The rod slot 108 in tulip 106 is configured for retaining the spinal rod. In the embodiment shown in FIGS. 4C-4D only a single bone fastener 110 is attached to the plate 102 to fixate the sacral-alar-iliac or sacroiliac joint.

Figure 4E:
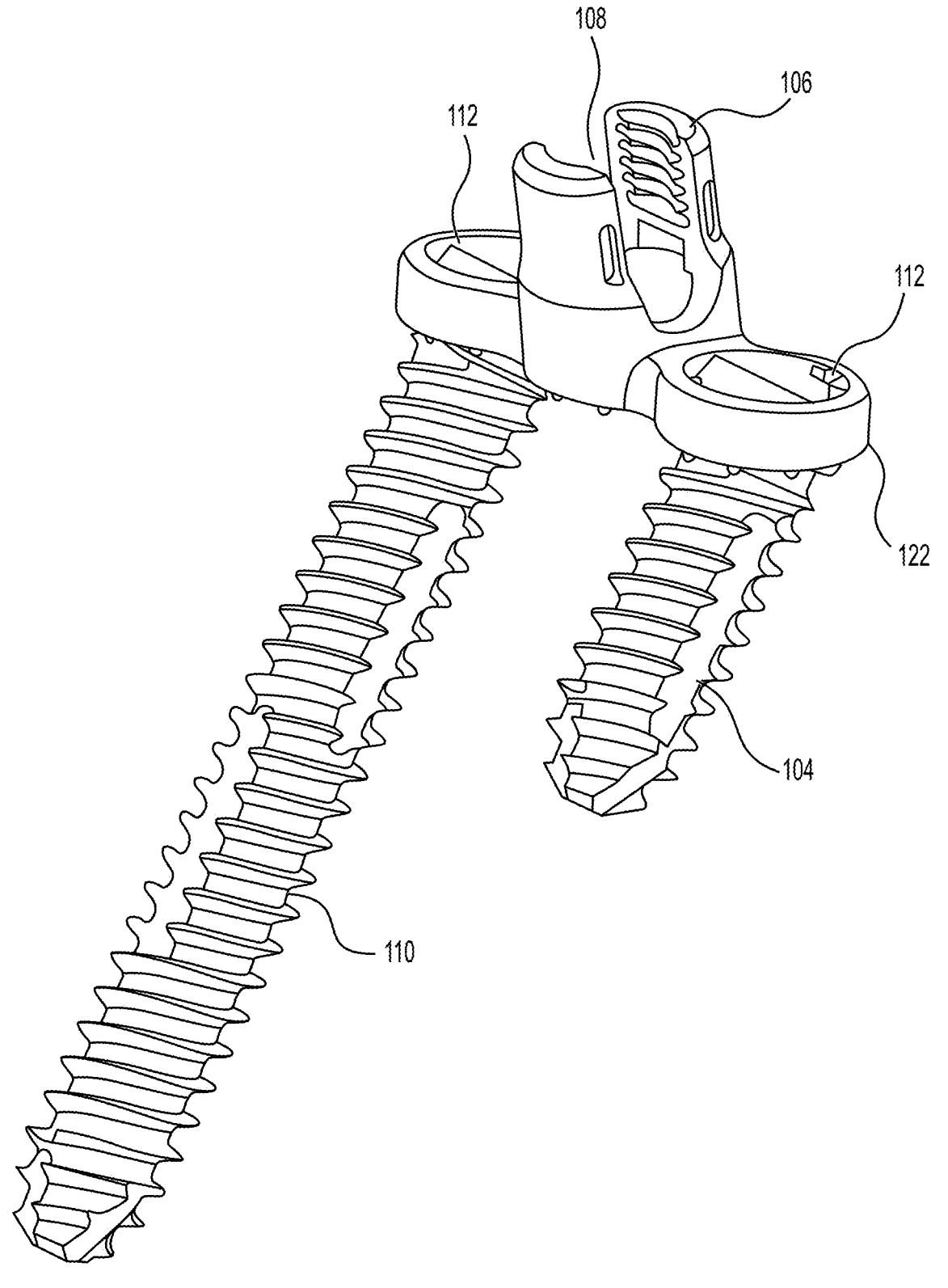

FIG. 4E shows an alternative version of implant 100 with a double screw plate 122 and integrated central tulip 106 for retaining the spinal rod. The head of first bone fastener 104 is retained in first opening 112 through plate 122 and the head of second bone fastener 110 is retained in the second opening 112 through plate 122. The plate 102 may include rings defining openings 112 on opposite sides of the tulip 106. The tulip 106 may be centrally positioned between the openings 112. In the embodiment shown in FIG. 4E, a pair of screws 104, 110 are attached to the plate 122 to fixate the sacral-alar-iliac or sacroiliac joint. As shown, the screws 104, 110 may be of varying lengths, but it will be appreciated that the any suitable screw type or length may be selected to achieve the desired fixation.

The screws may be offered in a multitude of diameters, styles and lengths, helping to insure optimal patient fit, while all having a singular screw to tulip connection mechanism for efficient manufacturing. Improvements to the screw shank manufacturing process and addition of marking channels for thread and/or flute timing may allow for intricate screw feature options to have consistency along screw diameters and lengths.

Screws and tulip may be sold preassembled, reducing the number of steps required to use when compared to unassembled screw and tulip sets, which simplifies the overall procedure and may reduce operating room time. Additionally, the ability to use instrumentation from other systems may reduce the number of sets required in the operating room, may streamline the procedure, and may also reduce operating room time due to a more streamlined technique.

One advantage in some of the embodiments described herein may include the ability to angulate the tulip to a larger magnitude than most existing pedicle screws, which increases the flexibility and simplicity of rod insertion and fixation in many instances of lumbosacral fusion or sacroiliac joint fixation. Another advantage may include a greater resistance to screw and tulip dissociation at extreme angles due to the internal design and method of connection. Screw and tulip dissociation is common in the sacral region and improvements to the strength of screws under a large angulation may be beneficial.

Figures 5A, 5B:
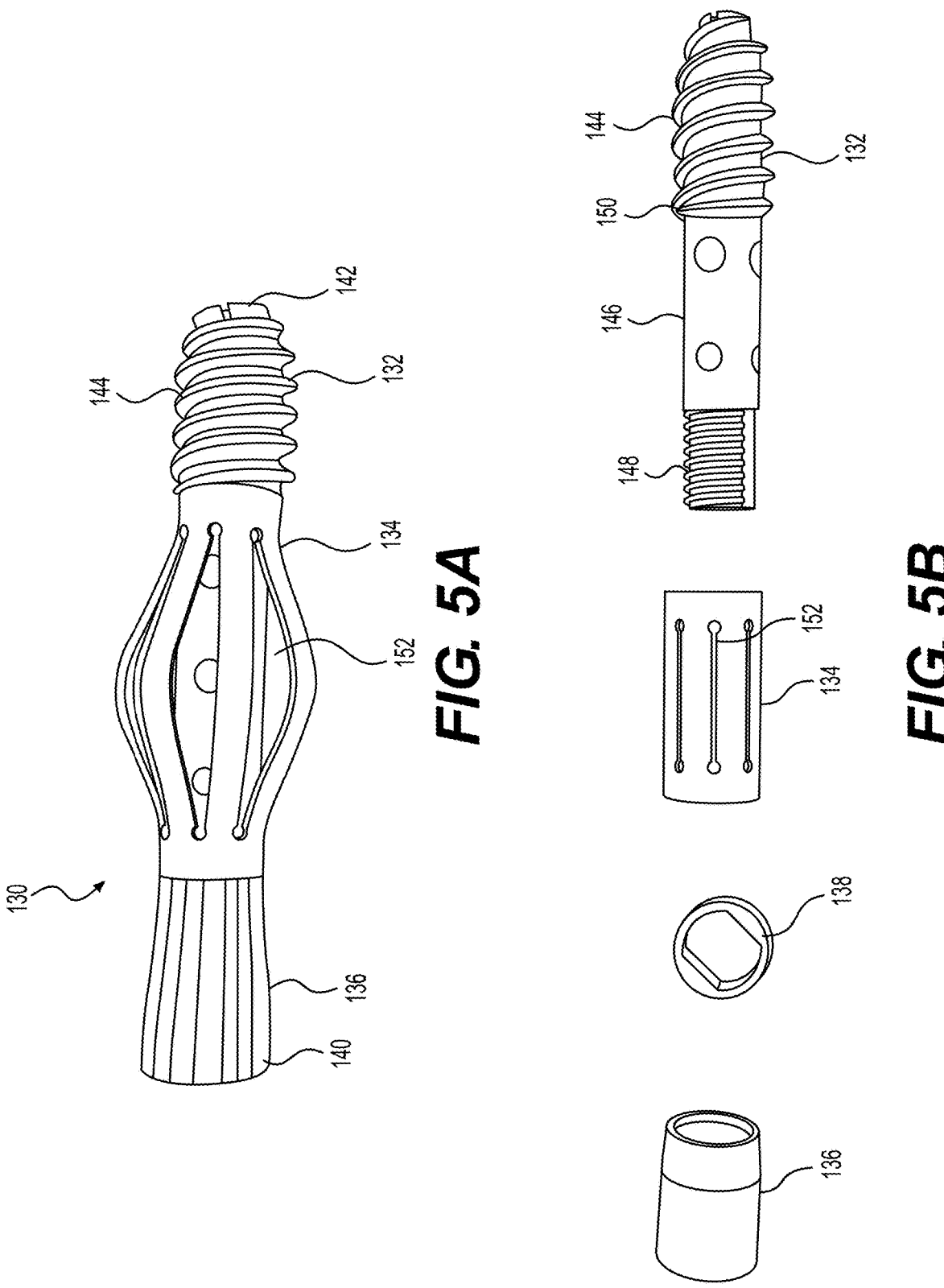
FIGS. 5A-5B show an expansion anchor screw according to one embodiment.

Turning now to FIGS. 5A-5B, an expansion anchor screw or expandable bone anchor implant 130 is shown according to one embodiment. The expandable bone anchor 130 has a collapsed configuration, thereby allowing the anchor 130 to be inserted into bone, for example, in a minimally invasive manner. Once inserted in the sacroiliac joint, the bone anchor 130 may be expanded into an expanded configuration, as best seen in FIG. 5A, thereby creating a strong press-fit in the bone.

The expandable anchor 130 extends from a first proximal end 140 to a second distal end 142 along a central longitudinal axis. As best seen in the exploded view of FIG. 5B, the expandable anchor 130 includes a screw body 132, an expandable collar 134, a threaded cap 136, and a slip ring 138. The screw body 132 includes a threaded distal section 144, a central section 146, and a threaded proximal section 148. The distal end 142 may have a distal tip that is blunt, pointed, or otherwise configured to engage bone. The threaded distal section 144 may include one or more threads with a suitable angle, lead, pitch, etc. to enhance insertion and/or engagement with the bone. The central section 146 may have a cylindrical body configured to receive the expandable collar 134. One or more openings may be provided into the central section 146. A lip 150 may separate the central section 146 from the distal section 144. The threaded proximal section 148 includes one or more threads configured to mate with internal threads in the threaded cap 136. The threaded proximal section may define a recess configured to receive an instrument for inserting the implant 130.

The collar 134 may be a hollow tube with a generally cylindrical outer shape in its collapsed configuration. The collar 134 is receivable over the central section 146 of the screw 132. The collar 134 defines a plurality of longitudinal slits 152, for example, equally spaced around the center of the collar 134. When in its initial collapsed configuration, the slits 152 may be arranged in parallel axially about the body of the collar 134. When the collar 134 is compressed, the beams between the slits 152 buckle or bend outwardly, thereby forming the expanded position, via flexion-based expansion. It will be appreciated that various profile geometries and slit configurations could be utilized in order to expand the collar 134.

The anchor 130 may be inserted laterally and then expanded around the middle by rotation of the threaded cap 136. The threaded cap 136 is cannulated with a threaded interior configured to engage with the threaded proximal section 148 of the screw 132. As the threaded cap 136 is rotated, an axial force is applied to the collar 134. The collar 134 is squeezed between the threaded cap 136 and the lip 150 on the screw 132, thereby causing a deformation of the collar 134. The slip ring 148 may be a circular ring positionable between the threaded cap 136 and the collar 134. The circular slip ring 138 may help to reduce friction in the mechanism during expansion.

One or more screws 132 may be inserted using a lateral approach to the sacroiliac joint, for example. A traditional driver or other suitable instrument may install the anchor 130 and then the central collar 134 may be expanded outwardly as shown in FIG. 5A. The expansion mechanism works without hinges or other moving parts, as may be visible in a threaded ramp based mechanism. Some benefits of a flexion-based expansion mechanism are simple parts and fewer part count.

Figure 6C:
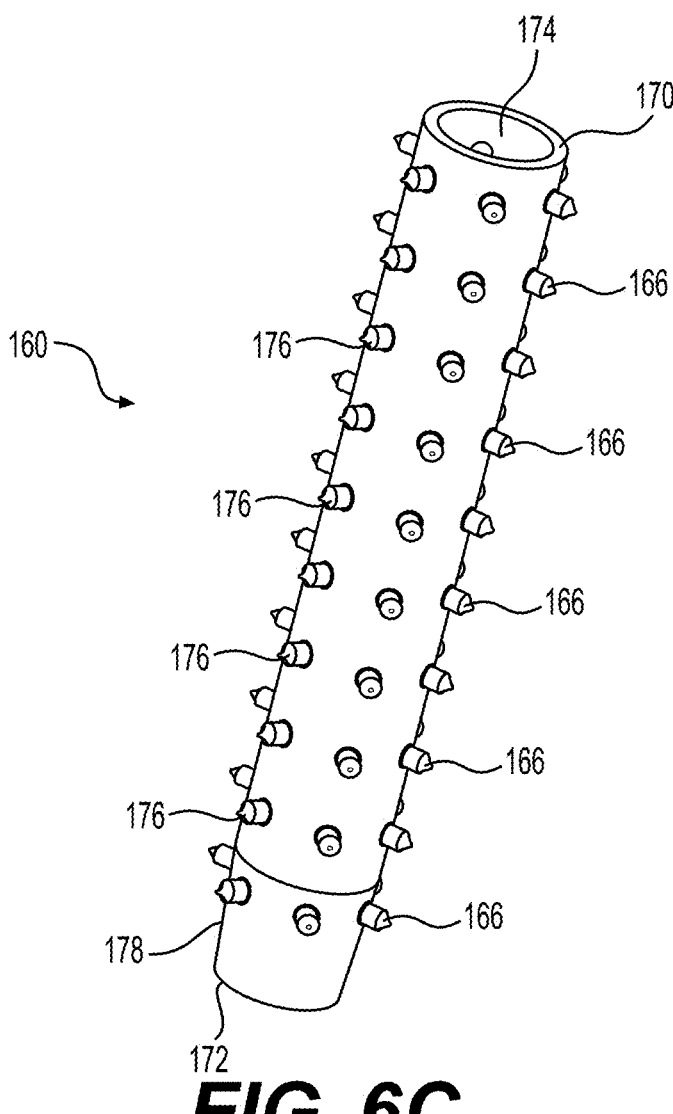

Turning now to FIGS. 6A-6H, examples of expanding pin implantable dowels or anchors 160 are shown. As shown in FIG. 6A, a hollow dowel 160 includes a conical distal tip 162 that can be inserted across the sacroiliac joint for fixation. As shown in FIG. 6B, upon insertion of an instrument or deployment key 164 through the center of the dowel 160, internal fixation pins 166 are released to move outward and fixate the implant into bone. For example, the deployment key 164 may be rotated 90° or another suitable degree of rotation to deploy the internal pins 166. Implant 160 has benefits in terms of ease of insertion without threads, and then increased migration resistance above a purely textured surface due to the protrusions. A tool to retract these pins 166 may also be inserted to ease ability for revisions.

FIG. 6C shows an embodiment of the implant 160 with the fixation pins 166 deployed and extended outward. The implant 160 may have an elongate dowel body extending from a first end 170 to a second end 172 along a central longitudinal axis. The first end 170 of the implant 160 may be a proximal end and the second end 172 may be a distal end configured to be inserted into bone. The distal end 172 may include a distal tip 178 that is narrowed, tapered, or conically shaped such that the tip is narrower than the body of the dowel 160. The narrowed tip 178 may help to facilitated insertion into bone. The dowel 160 may have a generally cylindrical shape, however, various profile geometries could be utilized in order to increase the fit of the implant in the bone. The dowel is cannulated with a center channel 174 extending along its length. The center channel 174 is in fluid communication with a plurality of perforations or openings 176 configured to guide the deployable pins 166. An opening 176 is provided for each respective pin 166.

Figure 6D:
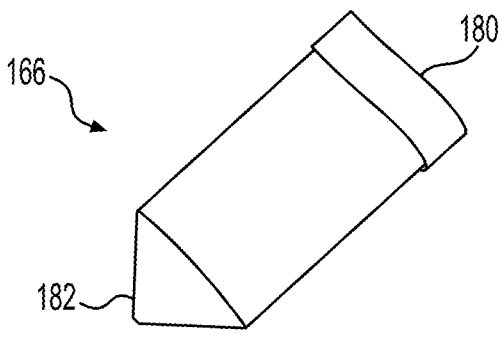

The pins 166 are deployable from the anchor body in order to secure the implant in the bone. The deployable pins 166 may include prongs, teeth, spikes, or other anchors configured to secure the implant in bone. As best seen in FIG. 6D, each anchor or pin 166 may be elongated with an inner end 180 receivable in the central channel 174 and an outer end 182 configured to eject from the respective opening 176. The pins 166 may have a generally cylindrical body. The inner end 180 of each pin 166 may have an enlarged lip or rim portion having a diameter greater than the diameter of the remained of the pin 166. The enlarged rim at the inner end 180 may help to retain the pins 166 in the openings 176. The outer end 182 may be pointed, sharpened, blunt, or otherwise configured to engage bone when ejected or expanded. For example, the outer end 182 may terminate as a conically-shaped point.

The pins 166 may be positioned generally transverse to the central longitudinal axis of the dowel 160. In particular, the pins 166 may be aligned generally perpendicular to the central longitudinal axis of the dowel 160. The pins 166 may be arranged in a pattern or array around the periphery of the dowel 160 or alternatively in a random configuration. The pins 166 may be equally spaced about the outer surface of the dowel 160. For example, rows of pins 166 may be arranged around the periphery of the dowel 160. In one embodiment, six rows of pins 166 are arranged equidistantly about the outer surface of the dowel 160. The array of pins 166 may extend along the entire length of the dowel 160 or along a portion thereof.

Figures 6E, 6F:
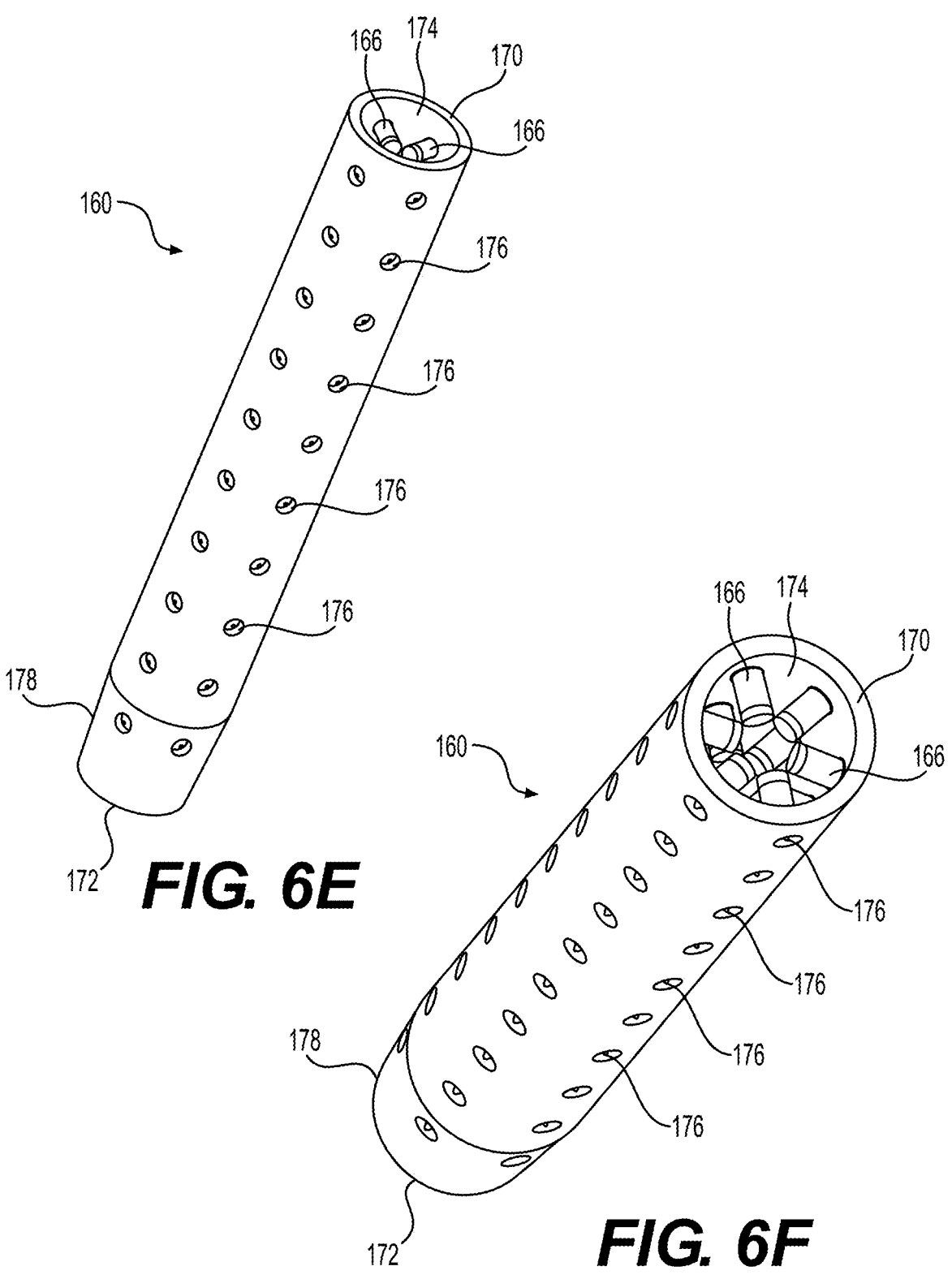

In the retracted position, the pins 166 are retracted inside the body of the dowel 160. FIGS. 6E-6F show the pins 166 fully contracted into the body of the dowel 160. In this configuration, the implant 160 may be inserted across the sacroiliac joint for fixation. In the deployed position, the pins 166 are extended radially outward and away from one another. In this embodiment, the anchor diameter is fixed while the pins 166 on the anchor surface are deployed from the dowel body 160 in order to secure the implant in the bone.

The pins 166 may be ejected mechanically with a piston, drive member, or internal shaft configured to interface with the pins 166. Alternatively, the pins 166 may be ejected pneumatically or with pressurized liquid, bone cement, or the like. As best seen in FIGS. 6G-6H, the pins 166 may be extended with expansion key 164. The expansion key 164 may include an elongated body having a generally cylindrical shape sized and dimensioned to fit within the channel 174 through the dowel body 160. The proximal end of the key 164 may have an enlarged flange 184 configured to abut the proximal end 170 of the dowel 160. The distal end of the key 164 may have a narrowed tip 186, for example, a conical tip configured to guide the key 164 through the channel 174. As the key 164 is advanced distally, the outer surface of the key 164 contacts the inner ends 180 of the pins 166 and the pins 166 are forced outwardly. As the key 164 is fully inserted through the dowel body 160, all of the pins 166 are fully deployed and extended, thereby fixing the implant in the bone.

Pin shaped implants, or other embodiments described herein without threads, may have an advantage of being implanted without large amounts of threading or tapping of a hole. This may save time in the operating room. Some embodiments may have features to allow self-packing of bone which would also save time during the operation. Other features may reduce the potential for migration by increasing implant size or other shape changes, or containing fixation deployment.

Turning now to FIGS. 7A-7D, examples of triangular pins 200 configured to cross the sacroiliac joint and promote fixation are shown. With emphasis on FIGS. 7A-7B, the triangular pin 200 extends from a first end 202 to a second end 204 along a central longitudinal axis. The pin 200 may have three planar sides generally forming a triangular cross-section. The triangular shape prevents rotation relative to the implant or movement of the joint. The triangular pyramid may have a slight angle or narrowing toward distal end 204, which may help with insertion and/or improve grip.

The planar faces of the pin 200 may be smooth or may have a surface texture 206. The surface texture 206, such as laser engraved surface texture, titanium plasma spray (TPS) coating, or 3D texturing may be added to promote bony on-growth. The implant 200 may include a cannulation or central through channel 208 for k-wire style trajectory planning and insertion. An internal threaded portion may be present, internal to the cannulation, for a rigid connection to an inserter or instrument compatible with a robotic and/or navigation system. This threaded portion may also be used with removal instrumentation if required.

Figure 7A:
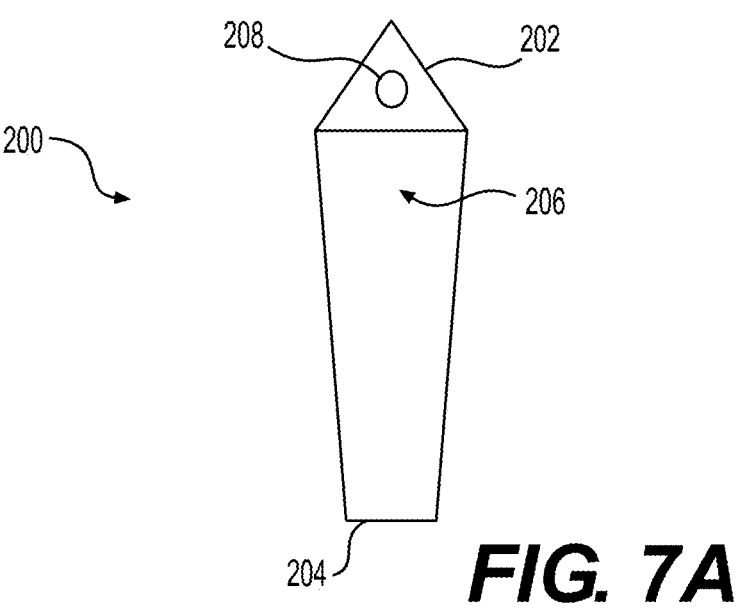
FIGS. 7A-7D show examples of triangular pins configured to fixate the sacroiliac joint.
Figure 7B:
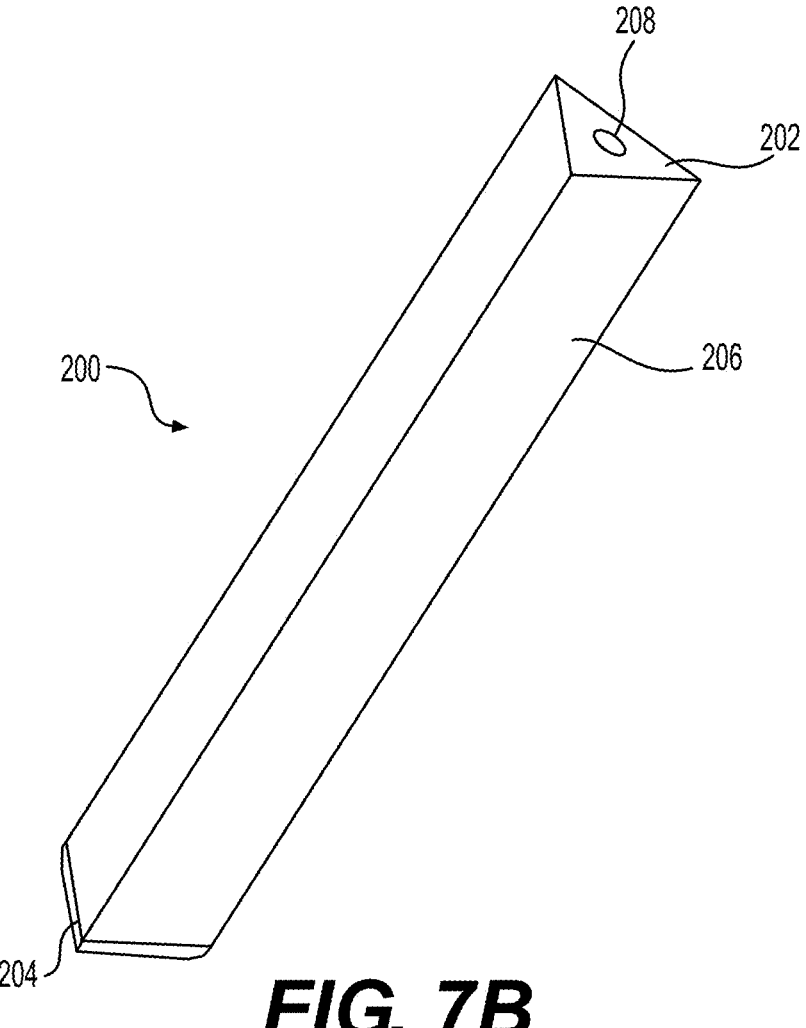
Figure 7C:
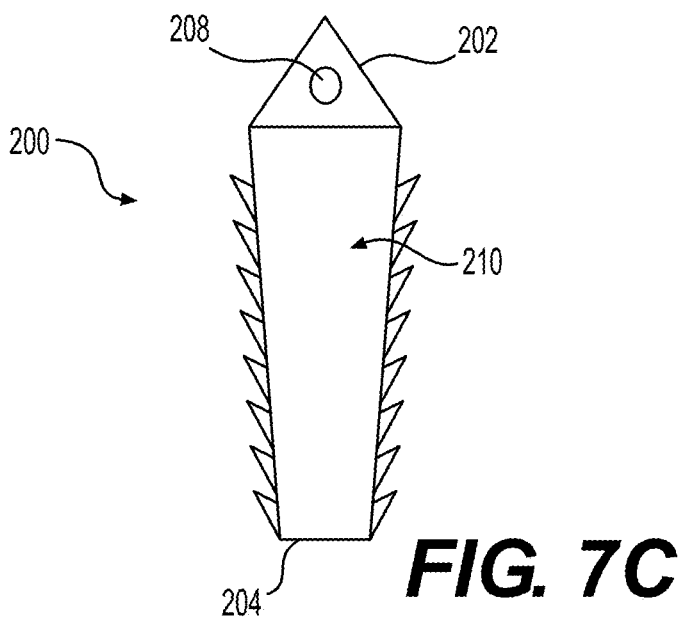
Figure 7D:
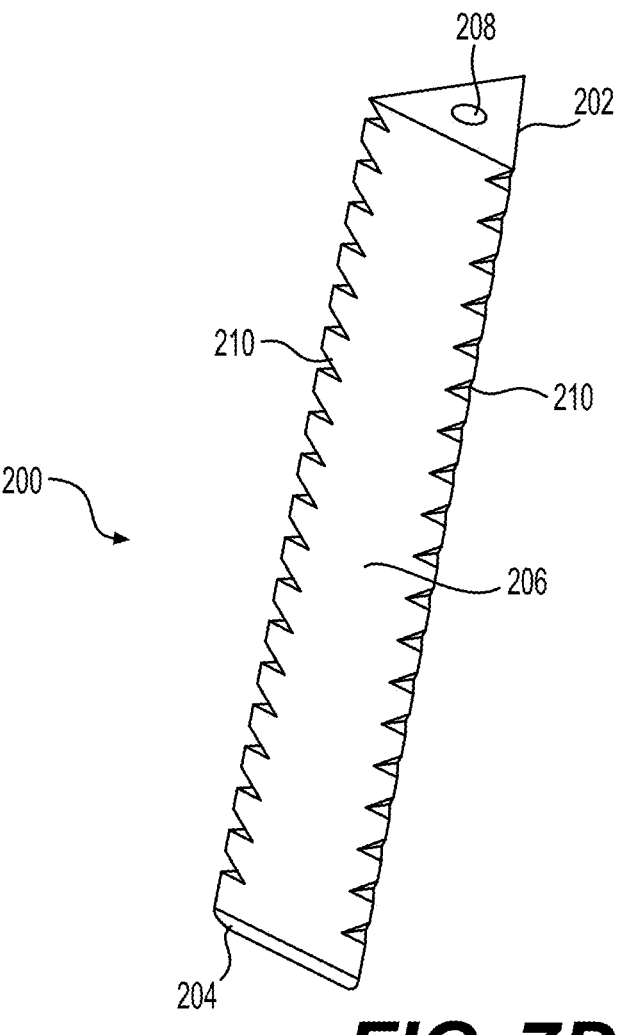

In another embodiment shown in FIGS. 7C-7D, one or more serrated edges 210 may be added to implant 200 to resist motion after implantation. For example, the serrated edge 210 may be notched, toothed, or jagged along its length or a portion of the edge. In one embodiment, each of the three outer edges 210 between the planar faces of the triangular pin 200 are serrated. The serrated edges 210 may be toothed in one direction such that the implant 200 is easily inserted but resists removal in the opposite direction.

Figures 8A, 8B:
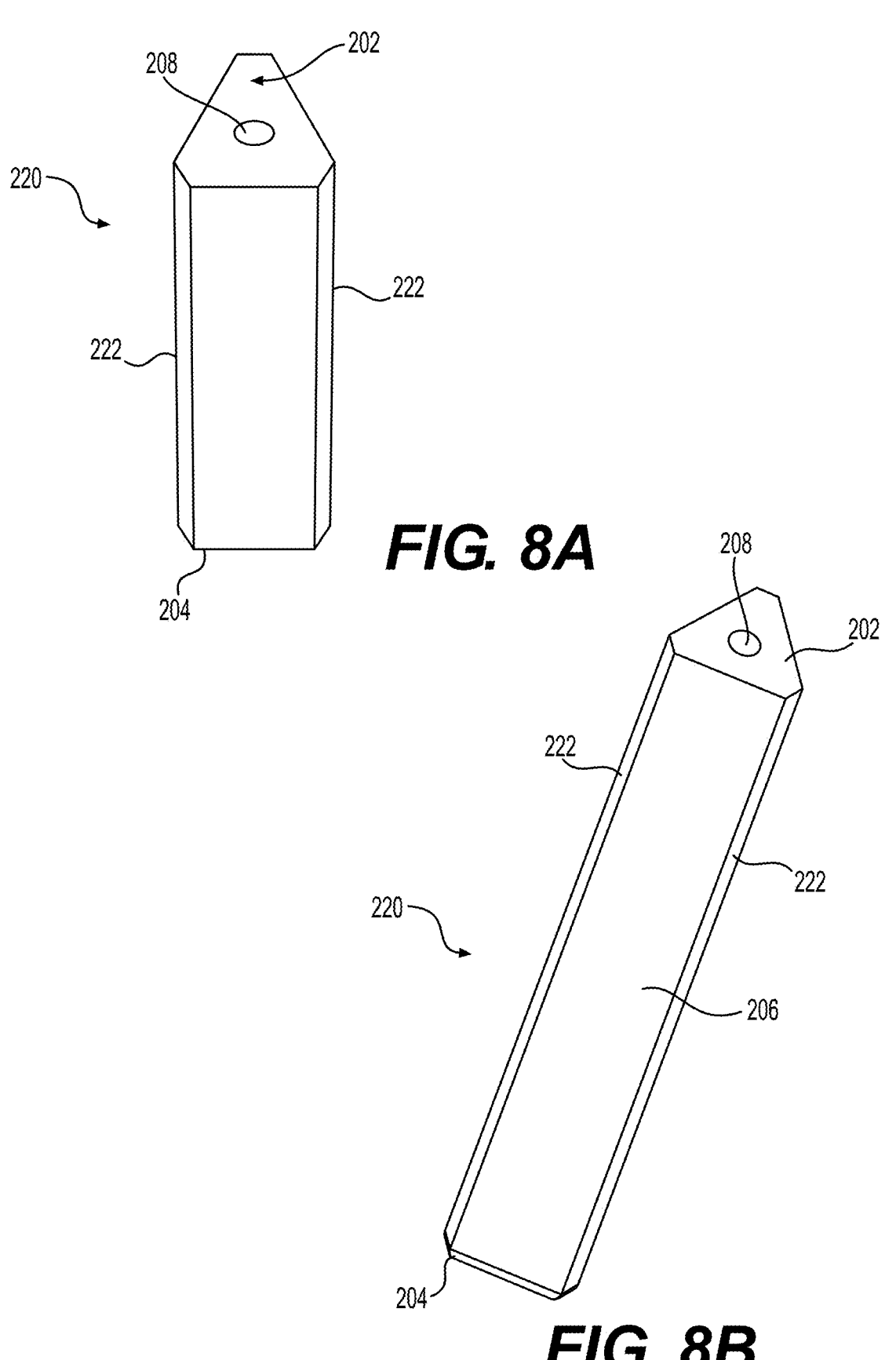
FIGS. 8A-8B show a triangular pin with soft corners for increased surface area and less sharp corners for safety according to one embodiment.

Turning now to FIGS. 8A-8B, a triangular pin 220 with soft corners 222 is shown according to another embodiment. Triangular pin 220 is similar to pin 200, but the corners 222 of the triangular pin 220 are smoothed or broken. The soft corners 222 may provide a less sharp implant to improve safety when holding and to increase surface area to promote bony ingrowth. The planar surfaces 206 may be optionally textured (e.g., laser etched, plasma sprayed, 3D textured) for bony ingrowth.

Turning now to FIGS. 9A-9D, examples of triangular pins 230, 240 with concave sides 232 are shown. With emphasis on FIGS. 9A-9B, the triangular pin 230, similar to pin 200, has a main body with three sides forming a generally triangular cross-sectional shape. In this embodiment, the sides 232 of the triangular pin 230 are curved and concave such that cutting wings or fins 234 are created that can enter a circular hole and cut their own path. For example, the inward shape of the implant 230 may enter a circular drilled holed rather than requiring broaching. This may decrease the number of steps required to implant and may remove the broaching step that might otherwise be used. This approach could be combined with robotic and/or navigation instrumentation to reduce surgical time due to decreased steps.

Figures 9A, 9B:
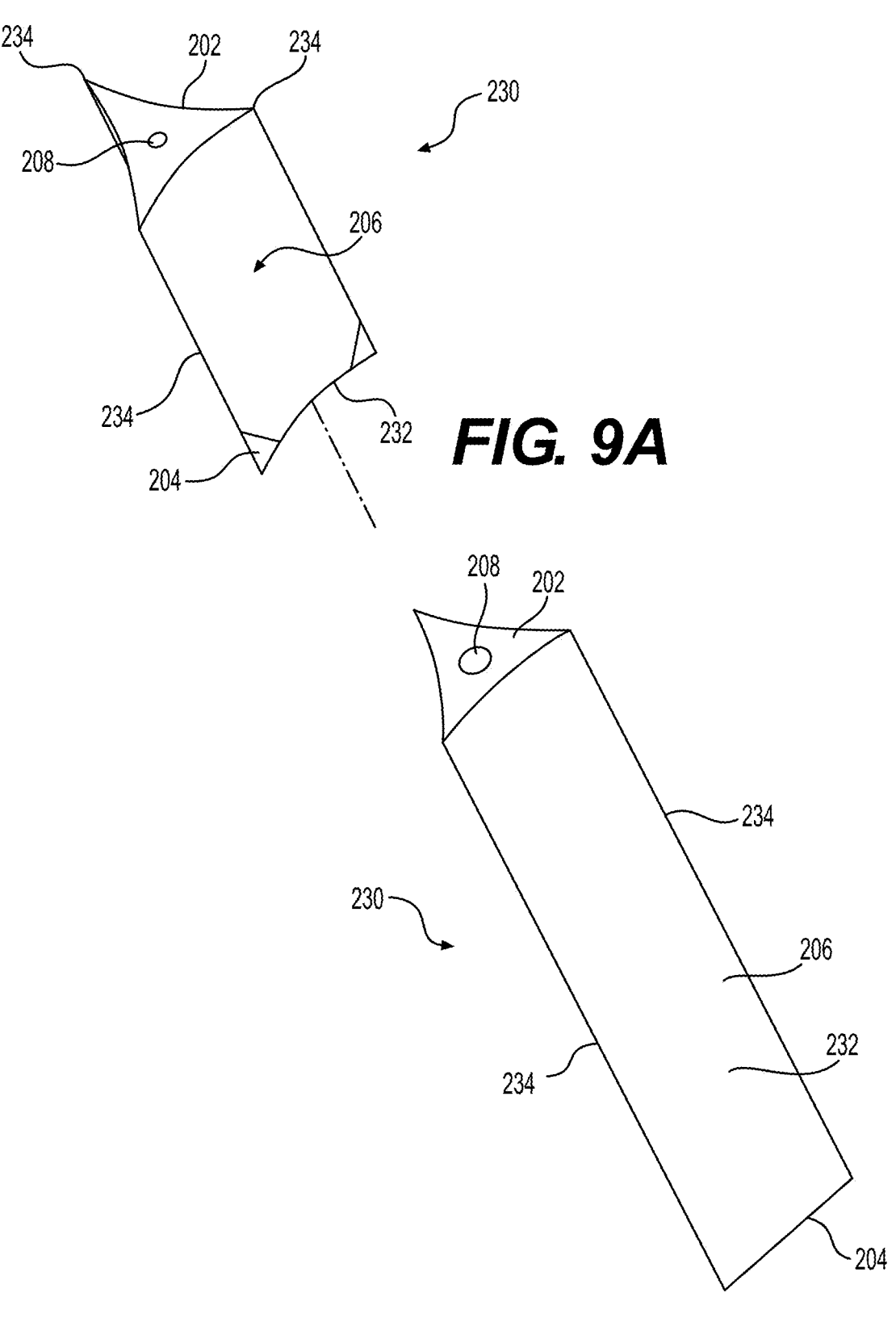
FIGS. 9A-9D show examples of triangular pins with concave sides.
Figures 9C, 9D:
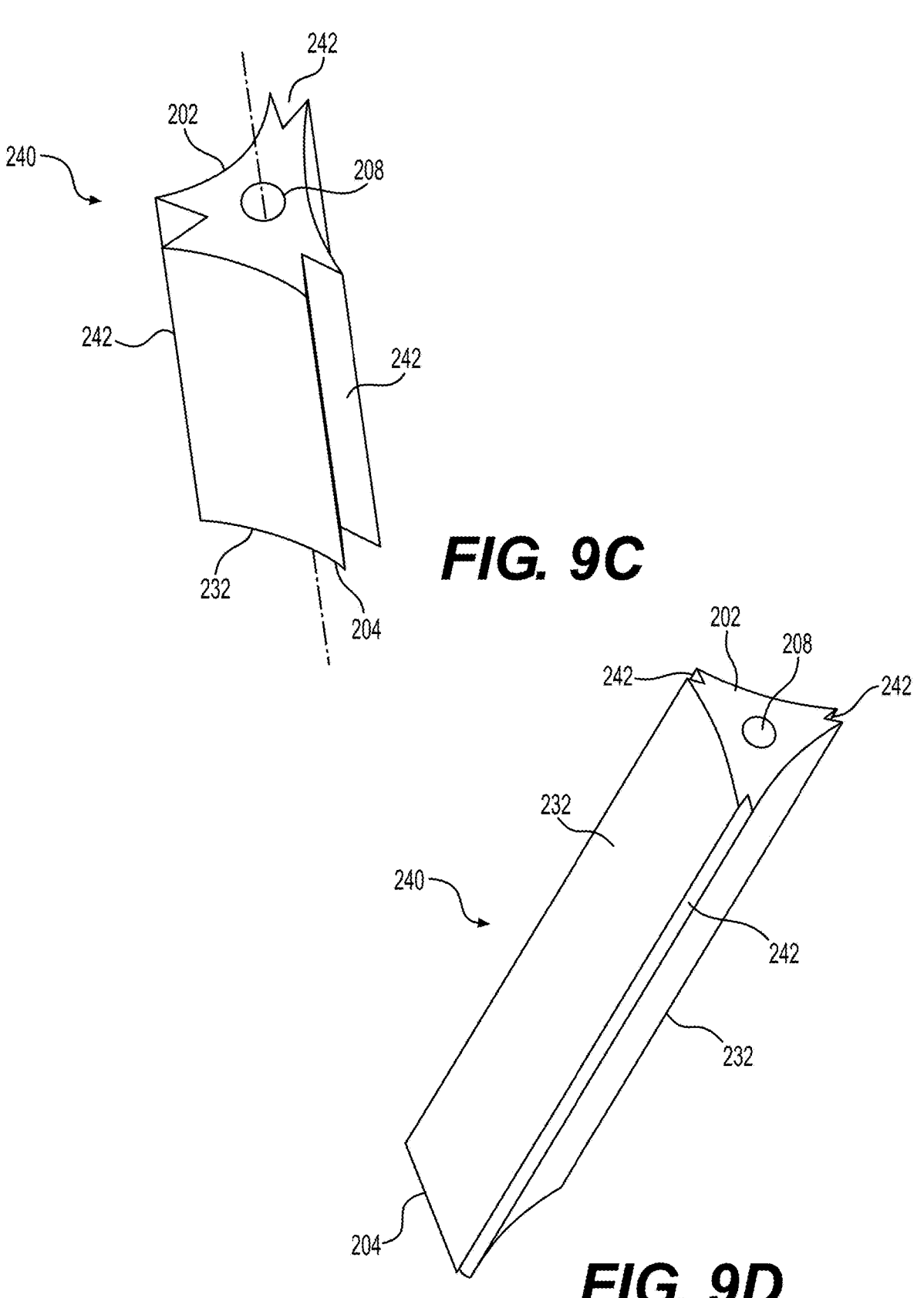

FIGS. 9C-9D show another variation where the triangular implant 240 includes double serrations 242 to increase bony contact surface area. Triangular pin 240, similar to pin 230, includes concave side faces 232. In this embodiment, the edges 242 are vertically serrated, thereby forming more aggressive cutting wings to trap bone. The extra surface area due to the vertical serrations 242 may provide for better fixation in bone. In addition, the cannulation 208 may be enlarged in diameter to provide counter-bored threads for implant removal.

Figures 10D, 10E, 10F:
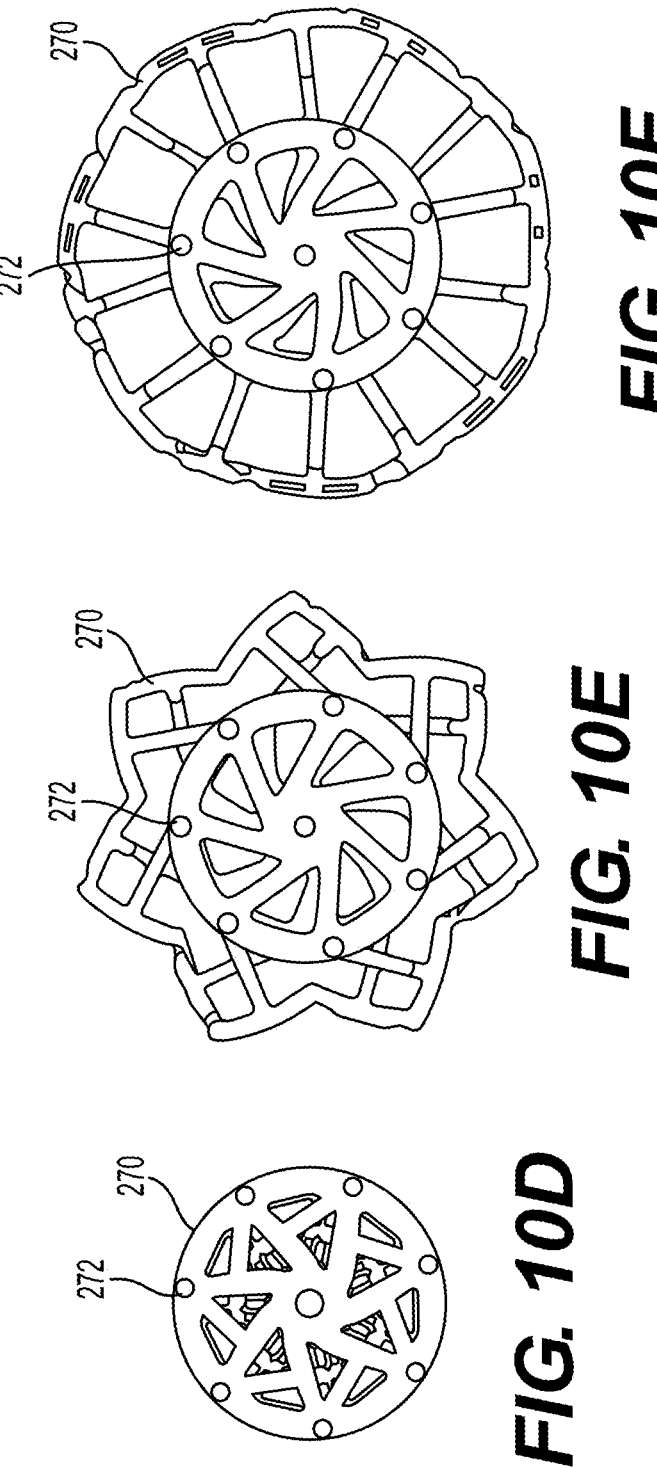

Turning now to FIGS. 10A-10H, examples of expanding geometry pins 250 are shown. With emphasis on FIGS. 10A-10C, the expandable implant 250 may include an outer expandable sleeve 252 and an inner plug or dowel 254 receivable in the sleeve 252 for expansion. As best seen in FIG. 10A, the expandable sleeve 252 may have a collapsed star shape extending from a first proximal end 256 to a second distal end 258 along a central longitudinal axis. In the embodiment shown, the sleeve 252 may form an octagram or an eight-angled star polygon with serrated points or edges. It will be appreciated that the star shape may have any suitable number of points and sections, such as a diamond star, pentagram, hexagram, decagram, etc. The sleeve 252 defines a central through opening 260 along the central longitudinal axis configured to receive the inner dowel 254. Each of the serrated points or edges of the star sleeve 252 may be interlocked with a hinge connection that can expand with the introduction and impaction of the dowel 254.

As best seen in FIG. 10B, the inner plug or dowel 254 includes an elongate body extending from proximal end 262 to distal end 264. The dowel 254 may have a cylindrical body tapering to a conical tip at the distal end 265 for easy insertion into the sleeve 252. A portion of the dowel 254 may be threaded 266, for example, near the proximal end 262, such that the conical dowel 254 may be locked into position. The dowel 264 may be cannulated to accept a k-wire, for example.

With emphasis on FIG. 10C, when the central dowel 254 is inserted into the central opening 260, the star sleeve 252 expands radially outward to fill the hole in the bone. For example, a pilot hole may first be drilled into the bone through the sacroiliac joint. Both the star implant 252 and dowel 254 may be impacted into position for easier use and to reduce threading. For example, the star sleeve 252 may be impacted first and the dowel 254 subsequently introduced to expand the body of the sleeve 252. Once expanded, the conical dowel 254 may be threaded 266 into place to lock the dowel 254 in position. Further, the implant 250 may be inserted into a blind hole drilled with robotic and/or navigational control. No tapping or other hole prep may be required, which may reduce surgical time.

FIGS. 10D-10F depict one embodiment of the mechanical linkage type expansion for the outer sleeve 252. FIG. 10D shows an example of sleeve 252 with a closed or collapsed position having a plurality of linkages 270 connected together via hinges 272. The hinges 272 may be joints, for example, due to bendable material, pins, or other suitable mechanical connections for expanding the linkages 270. In FIG. 10E, the sleeve 252 begins to expand in diameter as the linkages 270 bend and move outward. FIG. 10F shows an open or expanded position for sleeve 252 with linkages 270 fully extended outward.

Figure 10G:
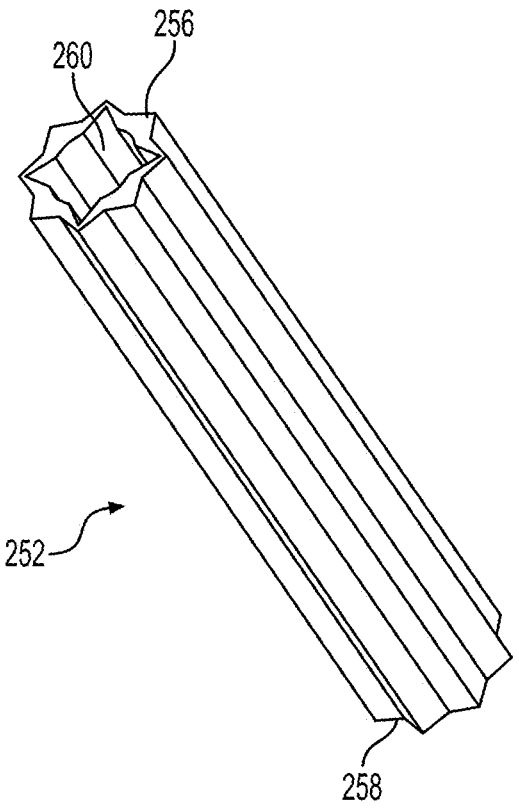
Figure 10H:
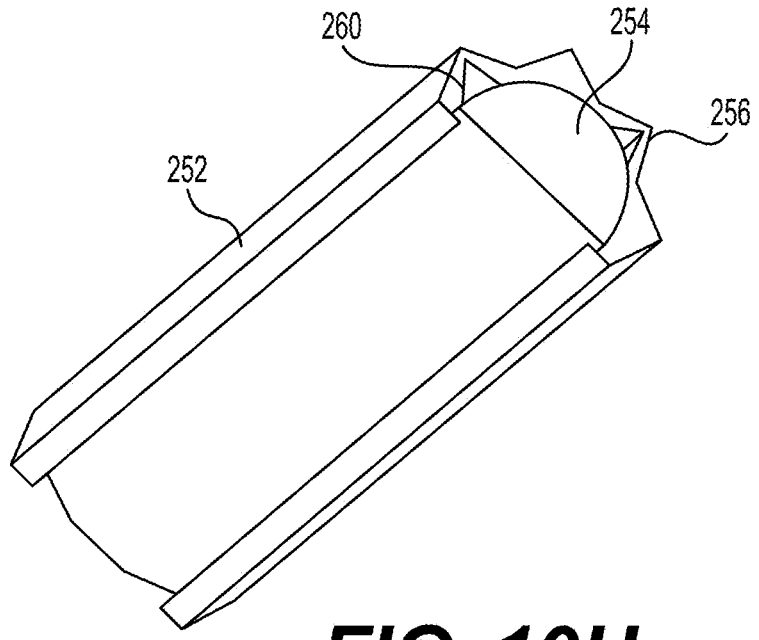

FIGS. 10G-10H show another version of expandable implant 250 including outer sleeve 252 and inner dowel 254. FIG. 10G shows a perspective view of the outer sleeve 252 having a collapsed star shape with a flexible geometry. In this embodiment, the outer sleeve 252 forms an eight-pointed star polygon with a non-cylindrical central opening 260. The cross-section of opening 260 may approximate a diamond star with rounded recesses configured to receive the cylindrical body of the central dowel 254. FIG. 10H shows a cross-sectional view of the dowel 254 inserted into outer sleeve 252, thereby expanding the flexible body of the outer sleeve 252.

Figure 11C:
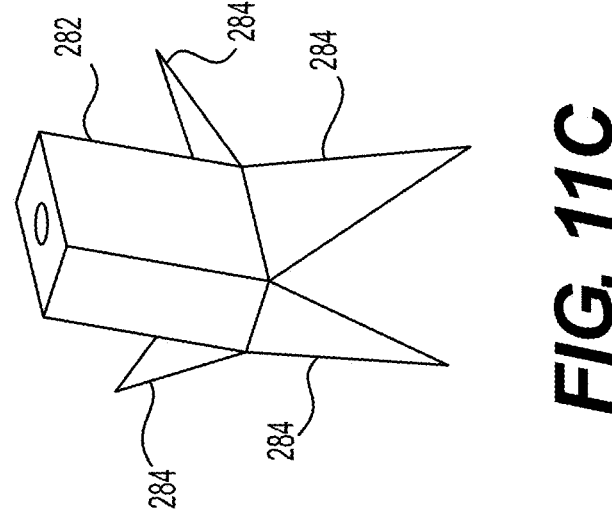
FIGS. 11A-11C show an expanding tip geometry pin with pyramidal arms according to one embodiment.
Figure 11B:
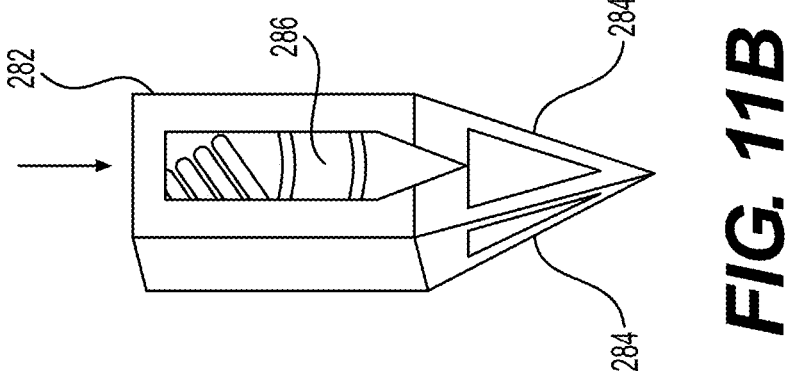
Figure 11A:
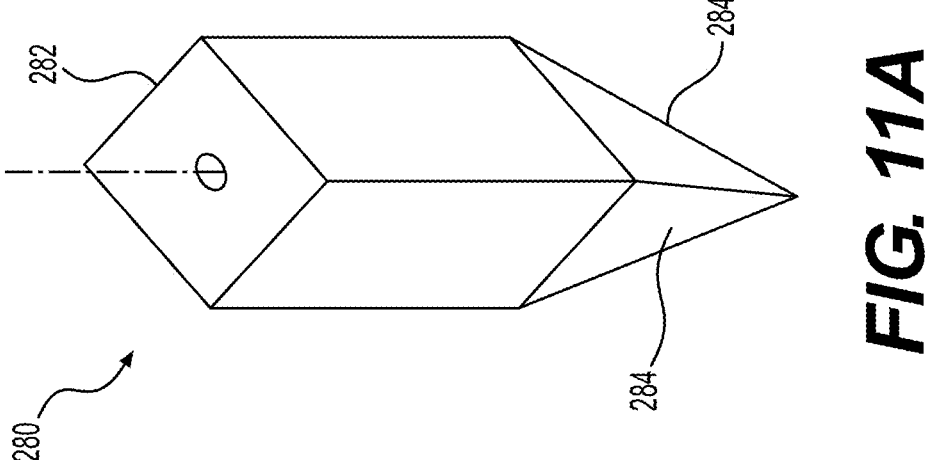

Turning now to FIGS. 11A-11C, an expanding tip geometry pin 280 is shown according to one embodiment. In this embodiment, polygonal pin 280 is inserted across the sacroiliac joint for fixation and an internal mechanism is rotatable to allow a cam, or other mechanism, to expand several fixation arms 284. As shown in FIG. 11A, the collapsed pin 280 has a body 282 and a plurality of distal arms 284. The body 282 may have polygonal shape, such as a cuboid, that terminates at a distal tip formed by the arms 284. The arms 284 may be in the form of fins or anchor type teeth. In the collapsed orientation, the arms 284 are out of the way to ease insertion. For example, four arms 284 may define an inverse pyramid in the collapsed position. As shown in FIG. 11B, an internal expansion mechanism 286, such as a cam, may be rotated to extend the arms 284. In FIG. 11C, the pyramidal arms 284 are expanded outward and away from one another to prevent migration of the implant 280. In the expanded orientation, the extended arms 284 promote fixation and secure the sacroiliac joint.

Figures 12A, 12B:
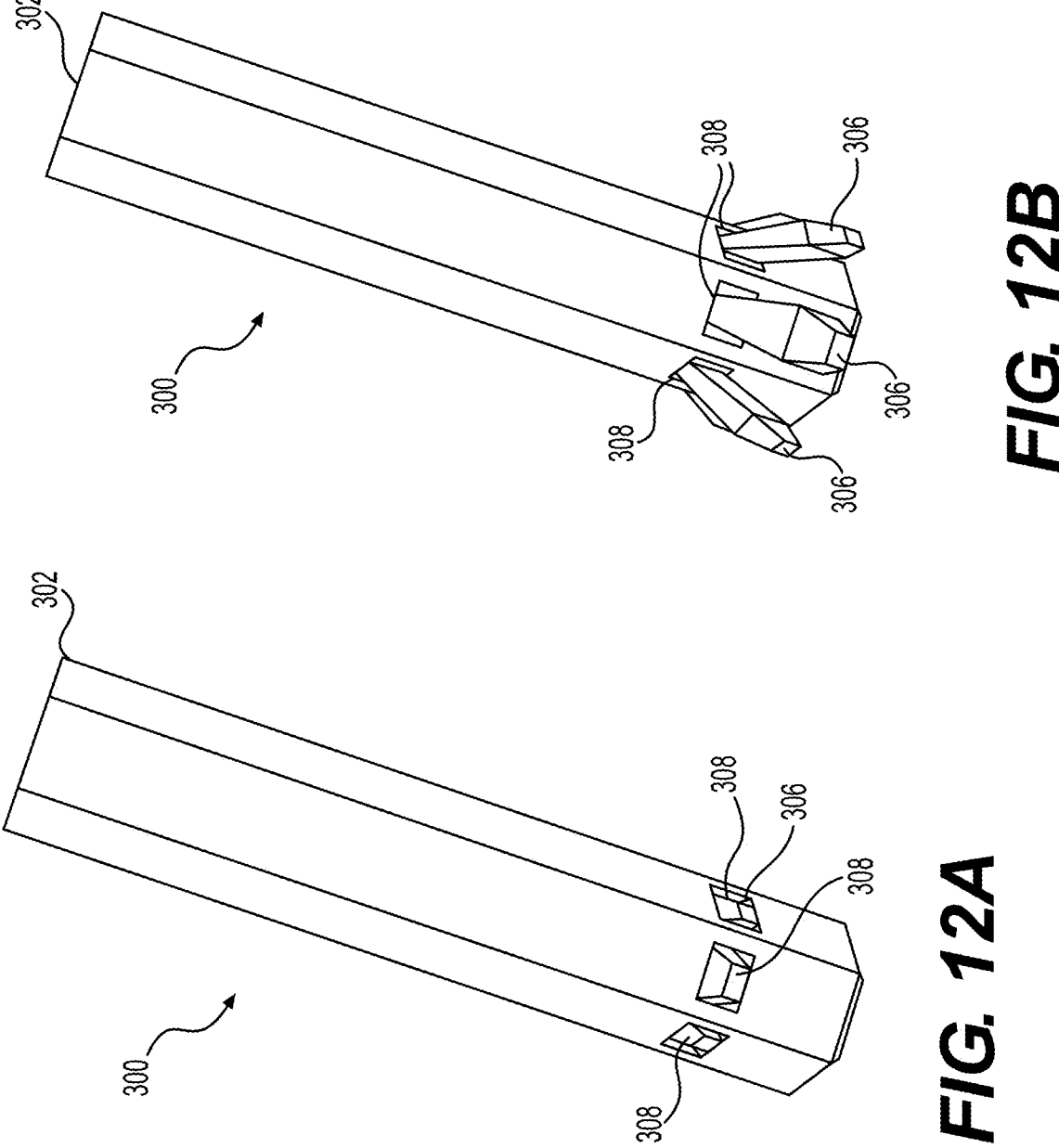
FIGS. 12A-12E show an expanding tip geometry pin with distal expansion teeth according to one embodiment.
Figure 12D:
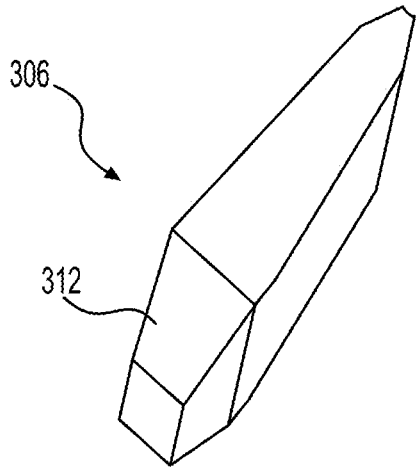
Figure 12C:
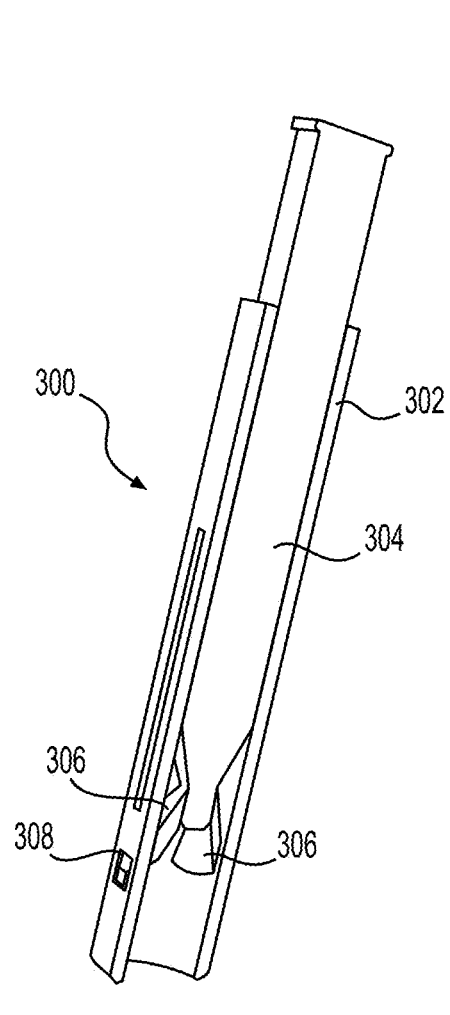

Turning now to FIGS. 12A-12E, an expanding tip geometry pin 300 having expandable distal teeth 306 is shown according to one embodiment. In this embodiment, polygonal pin 300 is inserted across the sacroiliac joint for fixation and an internal shaft 304 is moved axially to expand several fixation teeth 306. As shown in FIGS. 12A and 12C, the collapsed pin 300 has an outer sleeve 302 with a hollow body and a plurality of openings 308 near the distal end of the pin 300. The outer sleeve 302 may have polygonal shape, such as a hexahedron, with six planar faces arranged around the central opening. Each face of the hexahedron may define an opening 308 for receiving respective expansion teeth 306. It will be appreciated that the outer sleeve 302 may have any suitable cross-section and number of openings 308 for guiding respective teeth 306.

The inner shaft 304 is receivable through the outer sleeve 302 and translatable therethrough. The inner shaft 304 may be cylindrical or otherwise suitably sized and shaped to slide through the outer sleeve 302. A distal portion of the inner shaft 304 includes a plurality of teeth 306. The teeth 306 may be in the form of fins, arms, flaps, or the like. The teeth 306 may be configured to flex or bend relative to the body of the shaft 302. As best seen in FIG. 12D, each tooth 306 may include a body having a proximal portion attached near the free end 310 of the inner shaft 304 and a distal portion configured to engage bone. The teeth 306 may have tapered, beveled or chamfered sections 312, for example, along an upper face of the tooth 306 configured to engage bone. In the embodiment shown, six teeth 306 may be arranged to extend through the respective openings 308. It will be appreciated that any suitable number and type of teeth may be used to secure the implant 300.

Figure 12E:
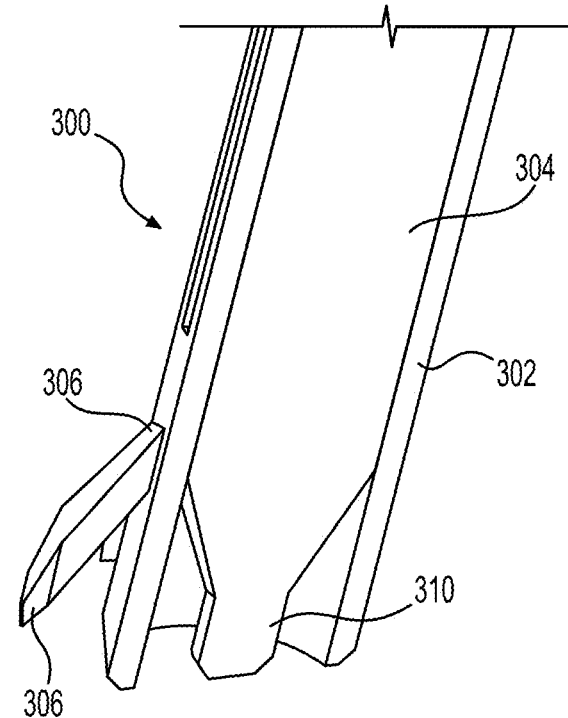

In the collapsed position shown in FIGS. 12A and 12C, the inner shaft 304 is proximally located in the sleeve 302 such that the teeth 306 do not extend through openings 308 in the outer sleeve 302. In this manner, the teeth 306 are fully housed within the body of the outer sleeve 302 and are out of the way to ease insertion of the implant 300 into bone. As shown in FIGS. 12B and 12E, as the inner shaft 304 is moved distally, the teeth 306 protrude through respective openings 308. The teeth 306 extend distally and radially outward to prevent migration of the implant 300. In the expanded orientation, the extended teeth 306 promote fixation and secure the sacroiliac joint.

Figures 13A, 13B:
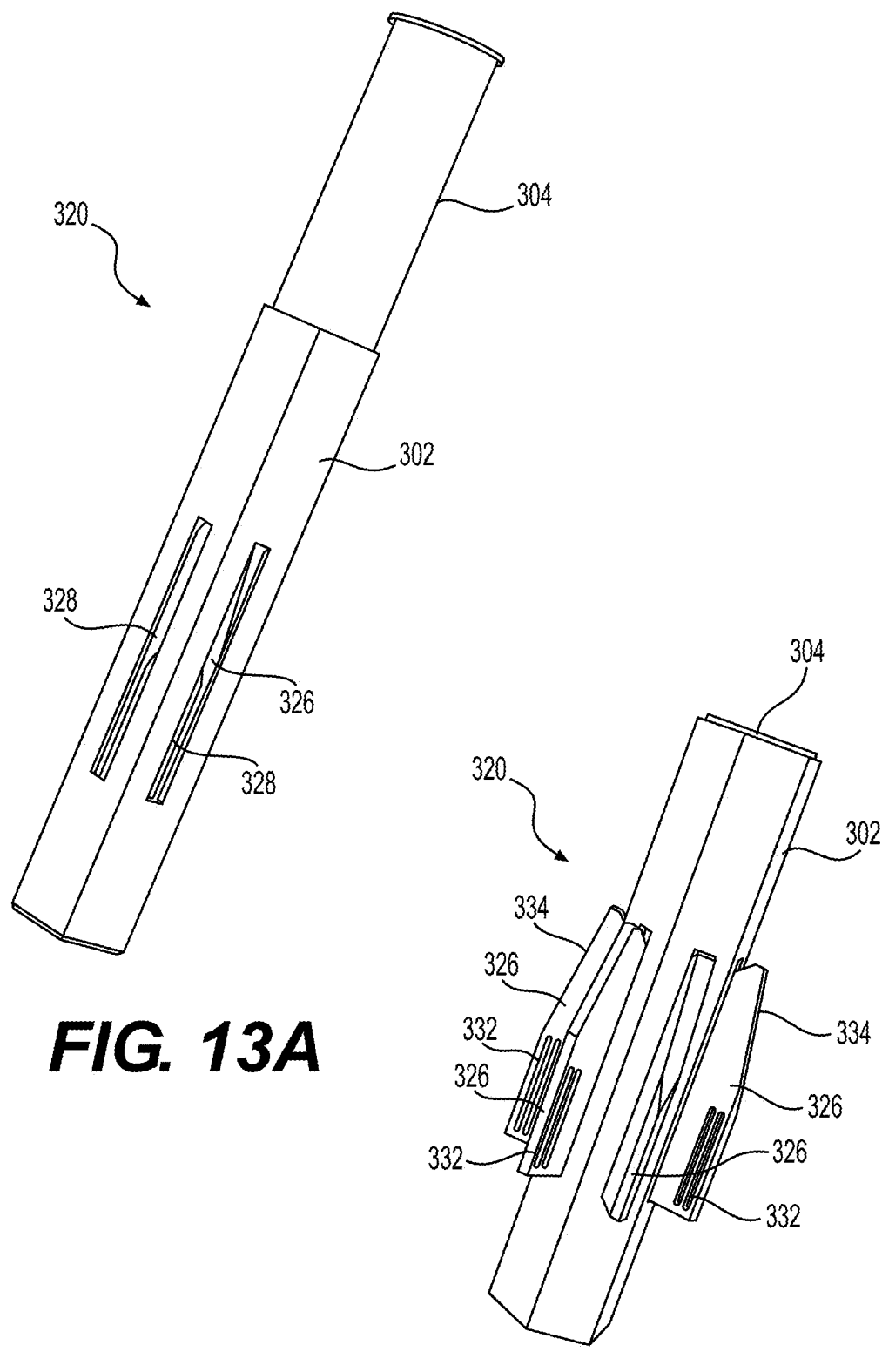
FIGS. 13A-13D show an expanding tip geometry with expansion fins according to one embodiment.
Figure 13C:
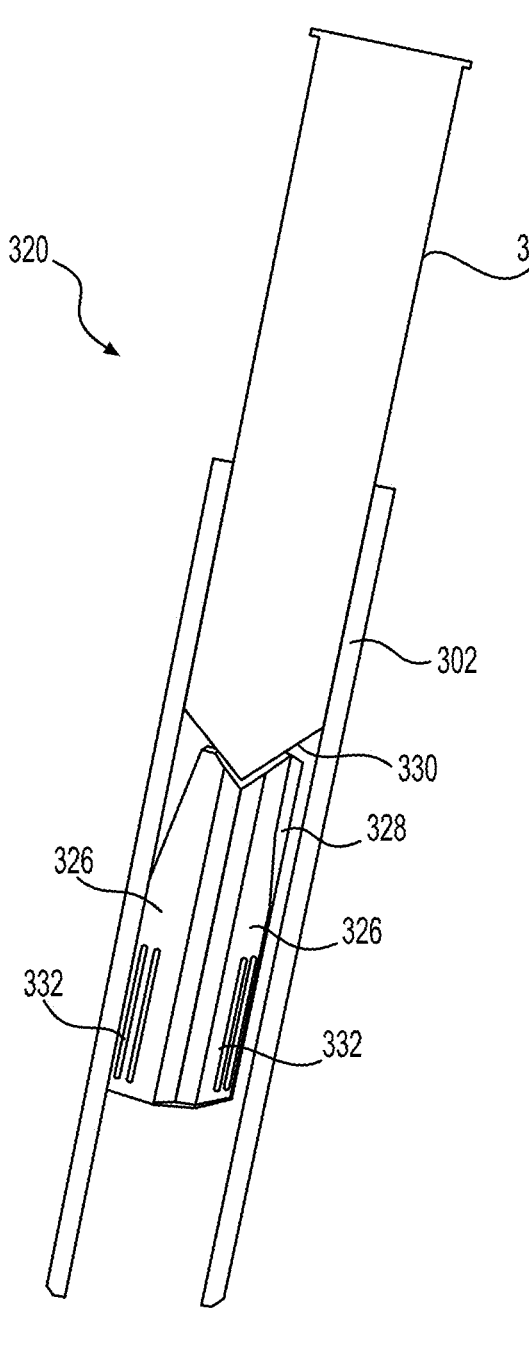

Turning now to FIGS. 13A-13D, an expanding tip geometry pin 320 is shown according to another embodiment. Implant 320 is similar to implant 300 except the teeth 306 are replaced with expansion fins 326. In this embodiment, polygonal pin 320 is inserted across the sacroiliac joint for fixation and an internal shaft 304 is moved axially to expand several expansion fins 326. As shown in FIGS. 13A and 13C, the collapsed pin 320 has an outer sleeve 302 with a hollow body and a plurality of openings 328 configured to receive the respective fins 326. The openings 328 may be elongated vertical slits sized and dimensioned to accept the length of the respective fins 326. In the collapsed position, the inner shaft 304 is proximally located in the sleeve 302 above fins 326 and the fins 326 are nested inside and fully housed within the body of the sleeve 302.

The expansion fins 326 may have elongated thin bodies with vertical serrations 332 to allow bone to grow within the implant for stronger fixation. The vertical serrations 332 may define vertical slits through the body of the fin 326. For example, each fin 326 may have a pair of vertical serrations 322 arranged in parallel to one another. The vertical serrations 332 may be positioned along a distal portion of the fins 326. It will be appreciated that any suitable number, type, and location of serrations 332 may be provided to improve bone growth. The fins 326 may have angled or tapered sections 334, for example, along a proximal portion of the fin 326. In this manner, the proximal end of the fin 326 may be narrowest and the fin 326 expands in width distally for a given section. In the embodiment shown, six fins 326 may be arranged to extend through the respective openings 328. It will be appreciated that any suitable number and type of fins may be used to secure the implant 320.

Figure 13D:
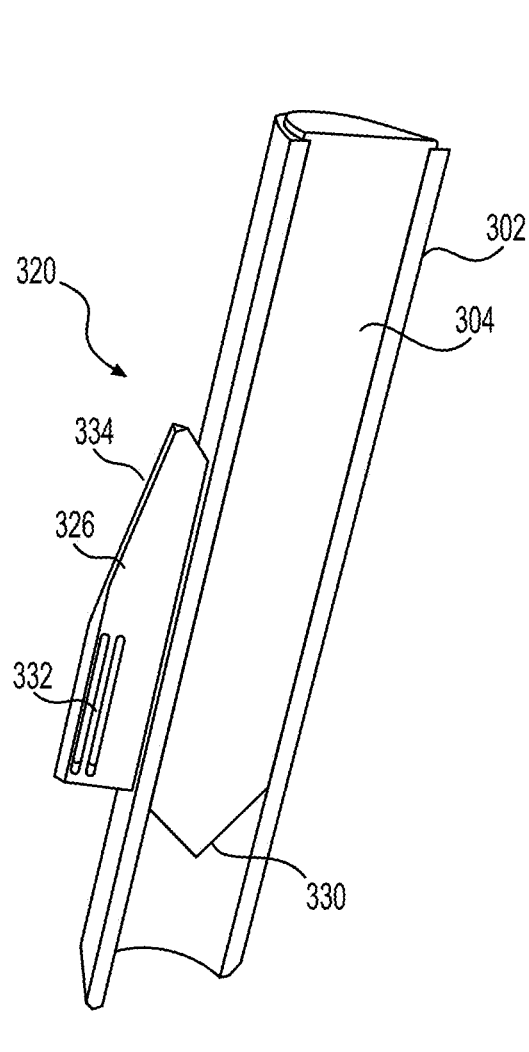

The fins 326 may be configured to slide out perpendicularly relative to the central longitudinal axis of the implant 320 via inner shaft 304. As shown in FIGS. 13B and 13D, as the inner shaft 304 is axially translated distally, the free end 310 of shaft 304 pushes against the top of the fins 326, thereby causing the fins 326 to extend outward and away from one another. The free end 310 of the shaft 304 may be angled or conical, for example, to engage with corresponding surfaces on the tops of the fins 326. After expansion, the fins 326 protrude through respective openings 328. The fins 326 extend radially outward to prevent migration of the implant 320. In the expanded orientation, the extended fins 326 promote fixation and secure the sacroiliac joint.

The implant 320 may optionally define a central cannulation for insertion over a k-wire and/or to house bone growth material. For example, the implant 320 may be backfilled with bone via a central threaded connection. This connection may also be used to attach the implant 320 to an implant holder. In one embodiment, the central shaft 304 may be cannulated for packing with autograft or suitable bone growth material.

Turning now to FIGS. 14A-14D and 15A-15D, examples of in situ buildable multi-link constructs 340 with independent sections 342 are shown. In these embodiments, the implants 340 include multiple units 342 that are joined together in situ to create the multi-link construct. The sections 342 may include one or more repeating sections 344 and/or end sections 346, 348. The sections 342 may have a variety of lengths to match patient anatomy. The sections 342 may be sequentially installed during the procedure. For example, each section 342 may be implanted using a robotic and/or navigation system for alignment and global anatomical positioning. The resulting implant 340 may create a multitude of joined shapes to match a variety of patients and pathologies.

Figure 14A:
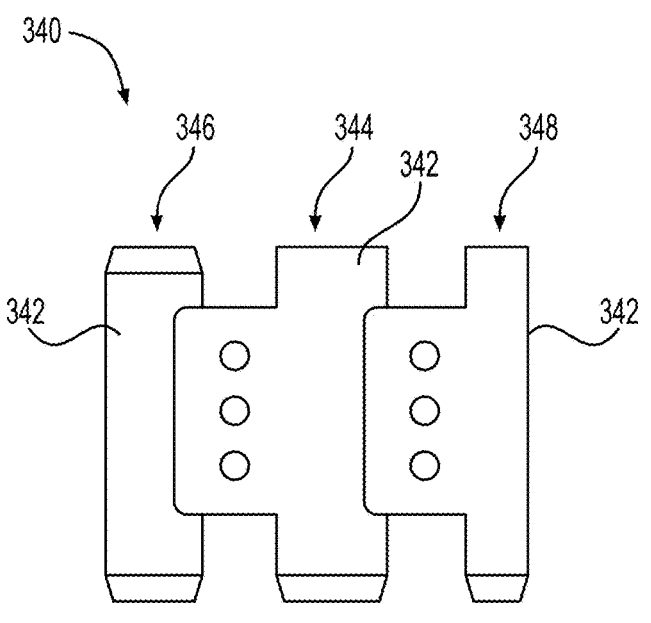
FIGS. 14A-14D depict examples of in situ buildable constructs with independent sections.

As shown in FIGS. 14A-14D, a plurality of buildable units or sections 342 may be connected to one another to form a wall-like structure with increased rigidity. FIG. 14A depicts resultant wall construct 340 created in situ. The sections 342 may be robotically placed to form the buildable wall. For example, end unit 346 may be positioned and internal section 344 may be coupled to end unit 346. Then, final section 348 may be coupled to internal section 342. It will be appreciated that the wall may be built in any suitable order with any suitable number of sections 342.

Figure 14B:
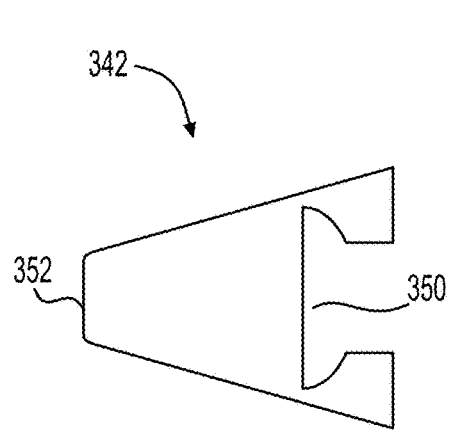
Figure 14C:
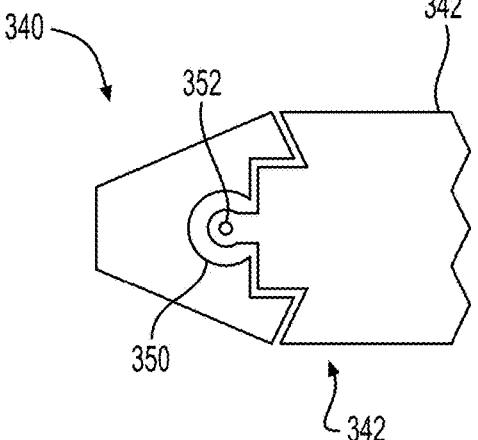
Figure 14D:
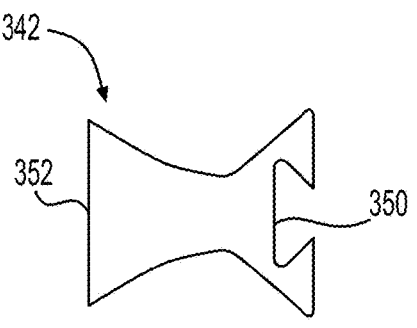

FIGS. 14B and 14D provide top views of stackable sections 342 according to some embodiments. Each stackable section 342 may have a female mating portion 350 and a male mating portion 352 at opposite ends of the section 342. In this manner, a male mating portion 352 of an adjacent section 342 is receivable in a female mating portion 352 of the given section 342, thereby permitting stacking or building of multiple components 342 together. The female mating portion 350 may include a channel, groove, socket, recess, chamber, etc. sized and dimensioned to hold the complimentary male mating portion 352. The male mating portion 352 may include a ridge, tongue, overhang, ball, projection, etc. sized and dimensioned to fit inside the complimentary female mating portion 350. FIGS. 14B and 14D depict examples of tongue and groove 350, 352 interlocking ends for buildable section 342. FIG. 14C depicts an example of a ball and socket 350, 352 interface between the two sections 342.

Figures 15A, 15B:
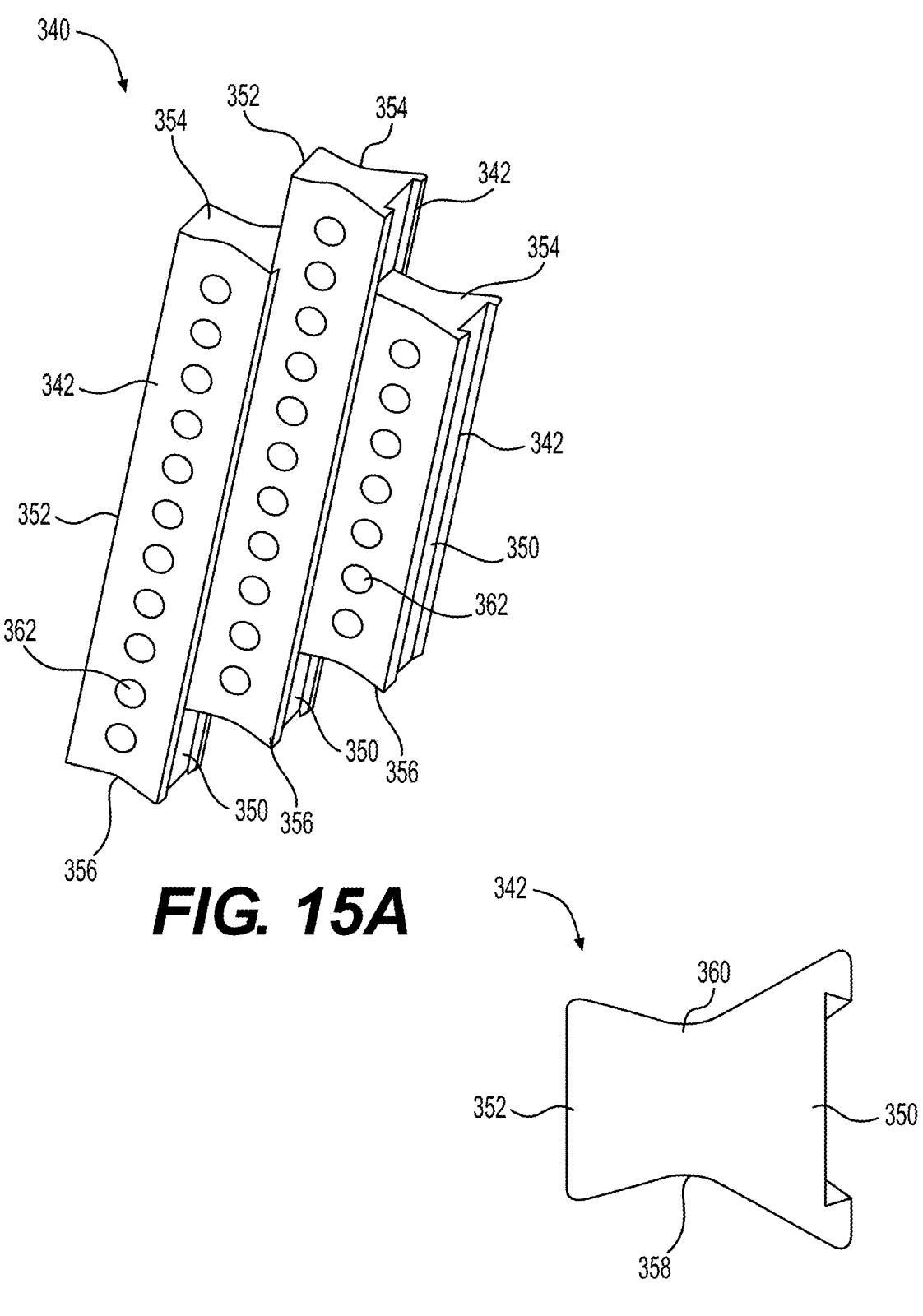
FIGS. 15A-15D show interlocking beams buildable in situ to create a multi-link construct according to one embodiment.

With further emphasis on FIGS. 15A-15D, the buildable implant 340 may be constructed in situ of interlocking beams 342 according to one embodiment. Each beam 342 may extend from a proximal end 354 to a distal end 356 along a central longitudinal axis. The beams 342 may be aligned in parallel to one another. The beams 342 may have a given length and the buildable construct 340 may include beams 342 of varying length. As shown in the embodiment of FIG. 15A, the resulting construct 340 may be built as a triple beam with two different lengths. The left-most and central beams 342 may have a long length and the right-most beam 342 has a short length. It will be appreciated that the number and lengths of beams may be selected during construction by the surgeon based on patient anatomy and the desired surgical outcome. The beams 342 may also be staggered such that the ends 354, 356 of beams 342 are not necessarily aligned with one another. In this manner, the beams 342 may take on a stepped or irregular positioning to match the patient anatomy.

FIG. 15B shows a top view of one beam 342. One side portion may define recess or groove 350 and the opposite side portion may define tongue 352 receivable in the next adjacent groove 350. The tongue 352 may have substantially the same width as the groove 350. To account for this sizing, the grooved side is larger than the tongued side. The front face 358 and rear face 360 may be concave or angled inward. For example, the front and rear faces 358, 360 may define an hourglass-like shape with a narrowed mid-section. A plurality of openings or holes 362 may extend through the beam 342, for example, to receive autograft, bone graft, or other suitable bone inducing material. For example, a series of holes 362 may extend between the front and rear faces 358, 360. The holes 362 in each beam 342 may be aligned along a single longitudinal axis.

Figure 15C:
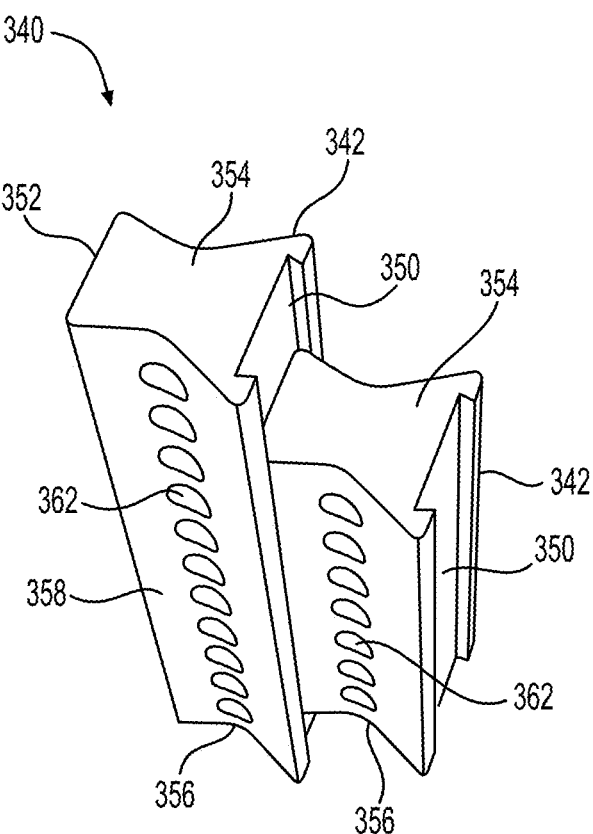
Figure 15D:
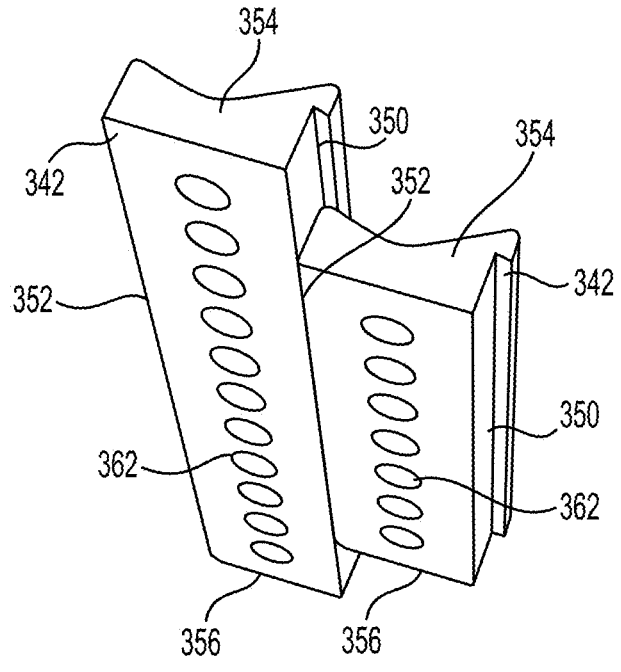

As best seen in FIGS. 15C and 15D, the tongued side 352 of one beam 342 is configured to fit within the negative grooved side 350 of the next adjacent beam 342. In this manner, multiple beams 342 are stackable together in series to form the multi-link construct. FIG. 15C shows an example of two internal stackable beams 342 and FIG. 15D shows a sectioned view of the interlocking beams 342. The tongue 352 may slidably engage the groove 350 on the next beam 342. For example, an axial force may be applied to the beam 342 being installed to attach the next beam 342 lengthwise. The ends of groove 350 may define an undercut, such as a dovetail interface, to guide and retain the adjacent tongue 352. The tongue and groove 350, 352 may be shaped in such a way to only allow translation during building, but to resist torsion or axial forces. The interlocking beams 342 may be built in situ, in any suitable order, to form the resulting rigid construct 340. In this manner, a larger construct may be planned and built through the use of robotic and/or navigation systems. This allows for the in situ assembly of a large and stable construct that is patient specific.

Turning now to FIGS. 16A-16C and 17A-17C, examples of auto-packing autograft triangular pins 380 are shown. With emphasis on FIGS. 16A-16B, the triangular pin 380 includes a proximal portion 382 and a distal portion 384. The proximal portion 382 may have a triangular body with three planar faces. The distal portion 384 may be shaped generally like a triangular prism with two triangular bases and three rectangular lateral faces. The proximal portion 382 may be enlarged relative to the distal portion 384. The proximal portion 382 may form a sealed cap at the top of the implant 380.

Figures 16A, 16B, 16C:
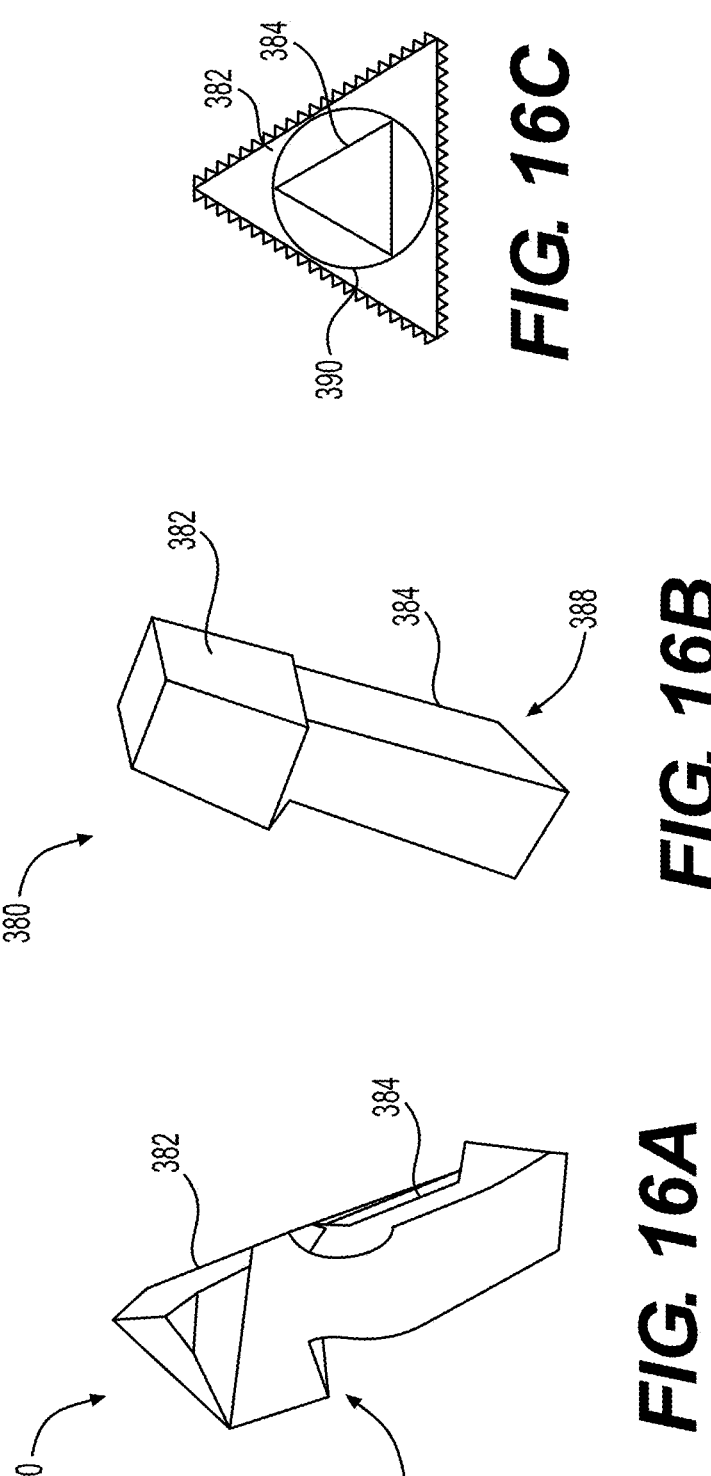
FIGS. 16A-16C show an auto-packing autograft triangular pin according to one embodiment.
Figures 18A, 18B, 18C:
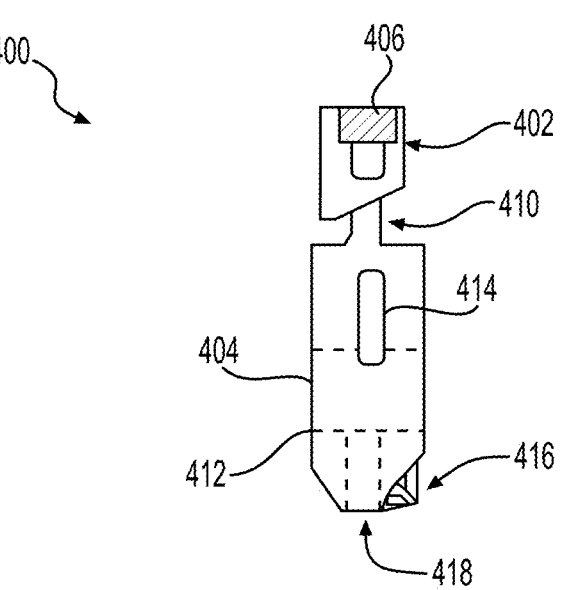
FIGS. 18A-18D show embodiments of a fusion screw with overlapping graft windows.
Figure 18D:
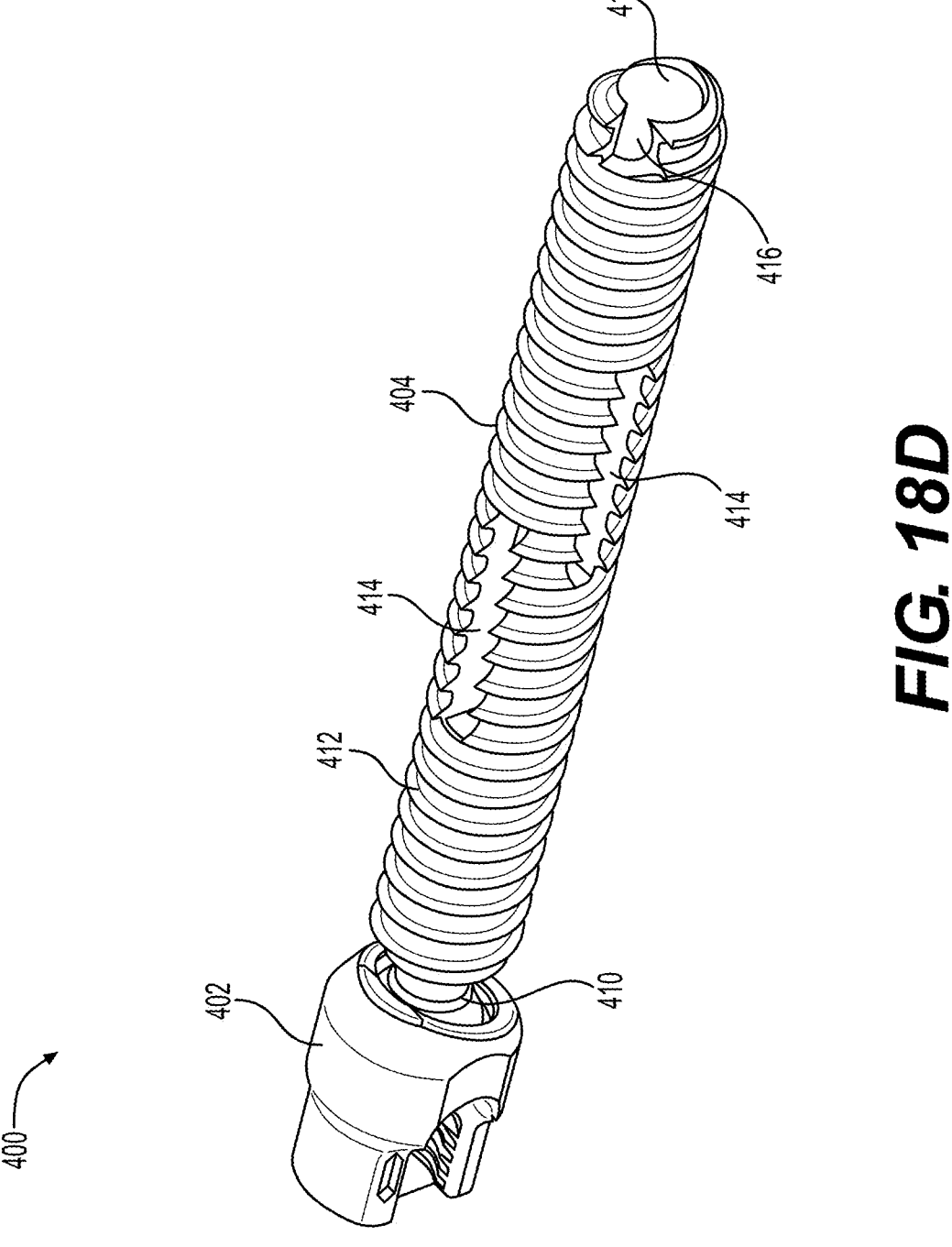

The implant 380 may define one more internal cutting notches 386 in fluid communication with one or more self-packing channels 388. The cutting notches 386 may be used to shave bone during insertion to be internally packed and later used to promote fusion. The implant shape is created by two differently sized shapes, enlarged proximal portion 382 and reduced distal portion 384, such that the proximal portion 382 is configured to remove bone from a cannulation 390 in the patient. As best seen in FIG. 16C, the circle denotes the cannulation 390, the larger triangle denotes the proximal end 382 of the implant 380, and the smaller triangle denotes the distal end 384 of the implant 380. The overlap shows the region to be shaved and packed automatically into the implant 380.

With further emphasis on FIGS. 17A-17C, the triangular pin 380 may include sealed proximal portion 382 with three or more internal cutting notches 386 and distal portion 384 with three or more internal cutting notches 386. For example, three notches 386 may be arranged in each bottom corner of the distal tip and three notches 386 may be located at each bottom corner of the proximal sealed cap 382. Although six cutting notches 386 are exemplified, it will be appreciated that any suitable number and position of the cutting notches may be provided. The cutting notches 386 are configured to shave bone during insertion of the implant 380. The implant 380 may be generally hollow with one or more self-packing channels 388 aligned with the cutting notches 386. For example, the self-packing channels 388 may be provided along each corner of the triangular portions 382, 384 above each respective notch 386. A bore hole 392 may be in communication with the hollow implant 380. As the cutting notches 386 shave bone during insertion of the implant 380, the bone is packed inside the implant 380, thereby automatically packing the implant 380 with autograft.

Turning now to FIGS. 18A-18D, examples of sacroiliac joint fusion implants 400 with overlapping graft windows 414 are shown. In an exemplary embodiment, the implant 400 is a slotted screw with overlapping graft windows 414, a preferred angle tulip 402, a wider shank 412 to withstand great anatomical loads, and a large cannulated tip 418 to help pack bone into the screw during insertion.

The implant or bone fastener assembly 400 may include tulip element or tulip head 402 attached to bone fastener 404. The tulip head 402 may include a body with arms that separate a rod slot. The rod slot in the tulip head 402 is configured to receive a spinal rod and a locking cap 406 may be used to secure the spinal rod in the tulip head 402. In the embodiment shown, the bone fastener assembly 400 is a favored angle screw configured for sacroiliac joint fusion. In an exemplary embodiment, the tulip 402 is not modular for improved strength and has a closed tulip for increased rigidity.

The bone fastener 404 may include a bone screw, anchor, clamp, or the like configured to engage bone, such as the sacral-alar-iliac or sacroiliac joint. In the embodiment shown, the bone fastener 404 is a bone screw having a screw head 408, wide neck 410, and a threaded shaft 412. The neck 410 may be widened for strength. The shaft 412 may also be widened to withstand great anatomical loads. The threaded shaft 412 may define one or more longitudinal windows 414 configured to receive bone or suitable bone graft material. The windows 414 may include overlapping graft windows.

The distal end of the threaded shaft 412 may be pointed, sharpened, blunt, or otherwise configured to engage bone. The distal end may further define a bone packing tooth 416 and large cannulation 418 to gather bone. The bone packing tooth 416 may be used to help generate bone chips that can pack the screw 404 at the distal tip. The screw 404 may be implanted with a robotic and/or navigation system such that a full cannulation through the entire implant is not necessary. This allows the self-packing front-only cannulation 418 to be used. Thus, the cannulation 418 may only extend from the distal tip to the window 414. The large, cannulated tip may help to pack bone into the screw 404 during insertion.

Figure 19B:
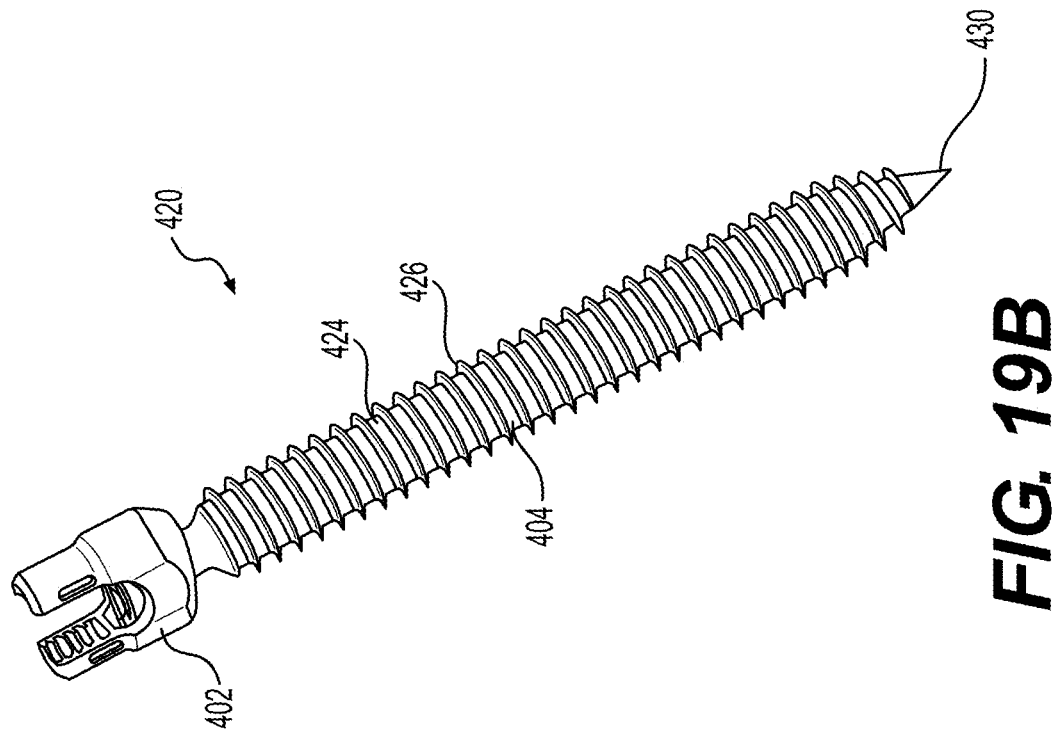
FIGS. 19A-19B show a 3D printed mixed density implant according to one embodiment.
Figure 19A:
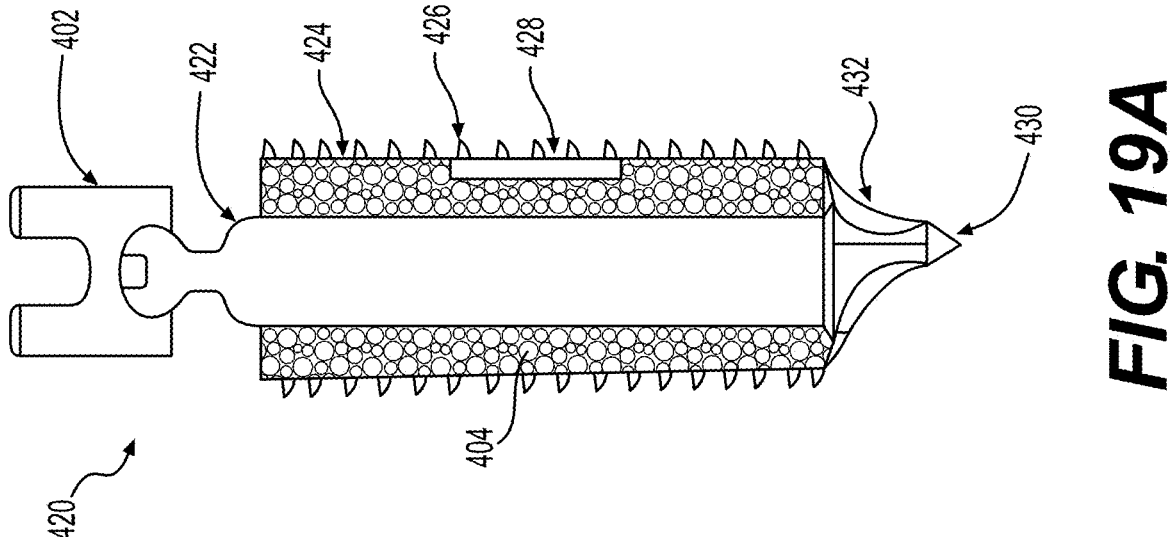

Turning now to FIGS. 19A-19B, a 3D printed mixed density implant 420 is shown according to one embodiment. Similar to implant 400, implant 420 may be a preferred angle tulip 402 with a screw 404 configured for sacroiliac joint fusion. In this embodiment, the screw 404 has a solid core 422 with an outer threaded surface 424. The solid core 422 may include a solid core neck and a solid core screw shank. The solid core screw shank may be covered by the outer threaded surface 424. The outer threaded surface 424 may have threads 426 and a textured and/or porous composition for boney ingrowth. The screw 420 may be 3D printed to achieve a mixed density composition. The benefit of having mixed density construction is to obtain strength properties from the solid core 422 and fixation benefits from the porous and/or textured outer surface 424. The threads 426 may also be shaped in such a way as to automatically pack the local porous structure 424 with bone during insertion. One or more window 428 in the outer surface 424 may be open to grab additional bone. A sharpened tip 430 on the screw 404 may help dock the screw 404 to the bone. The distal tip 432 may also be shaped for improved cutting. In this case, a cannulation may be unnecessary when implanting hardware using a robotic and/or navigation system.

Figures 20E, 20F:
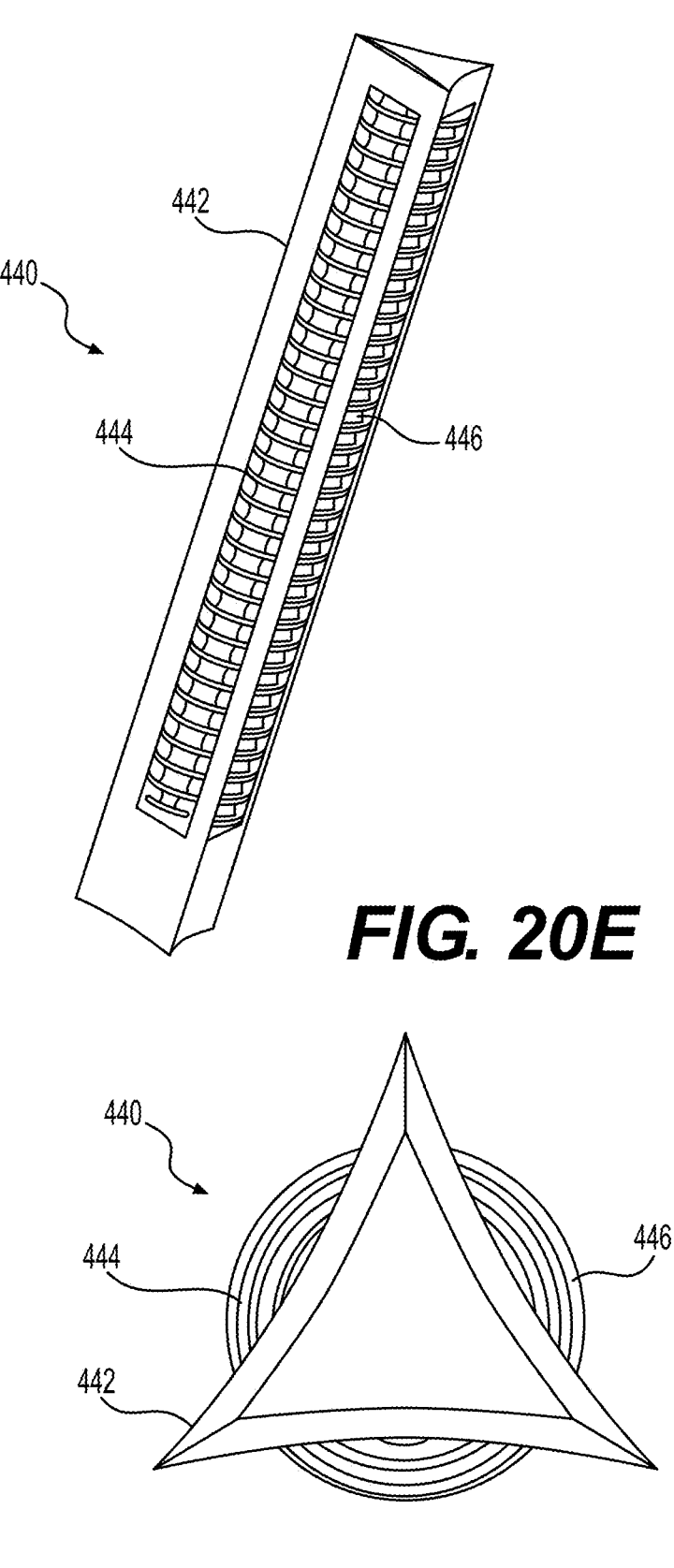

Turning now to FIGS. 20A-20F, examples of implants 440 with a triangular pin 442 and integrated screw 444 are shown. The implants 440 include a triangular pin 442 with three sides or faces generally forming a triangular cross-section. In FIGS. 20A-20B, the corners of the triangle are generally curved or contoured. In FIGS. 20C-20D, the sides are generally concave forming sharpened corners. In FIGS. 20E-20F, the three sides are generally planar or slightly concave. The triangular shape helps to prevent rotation of the implant or movement of the joint. The faces of the pin 442 may be smooth or textured. A surface texture, such as laser engraved surface texture, titanium plasma spray (TPS) coating, or 3D texturing may be added to promote bony on-growth.

The pin 442 is hollow and retains integrated screw 444 therein. One or more longitudinal windows 446 may be provided in the faces of the pin 442 allowing the internal screw 444 to project therefrom. The internal screw 444 includes a shank with threads 446. The internal screw 444 may be rotated to drive the triangular pin 442 through the bone and into a final location. The screw 444 is captured completely by the pin 442. In one embodiment, the screw 444 is printed into position with a 3D printer, thereby providing an ease of manufacturing. The integrated screw 444 prevents the internal components from being able to migrate post-operatively. In another embodiment, a section of the internal screw 444 is configured to rotate while on one side of the sacroiliac joint, causing compression.

Figures 21A, 21B:
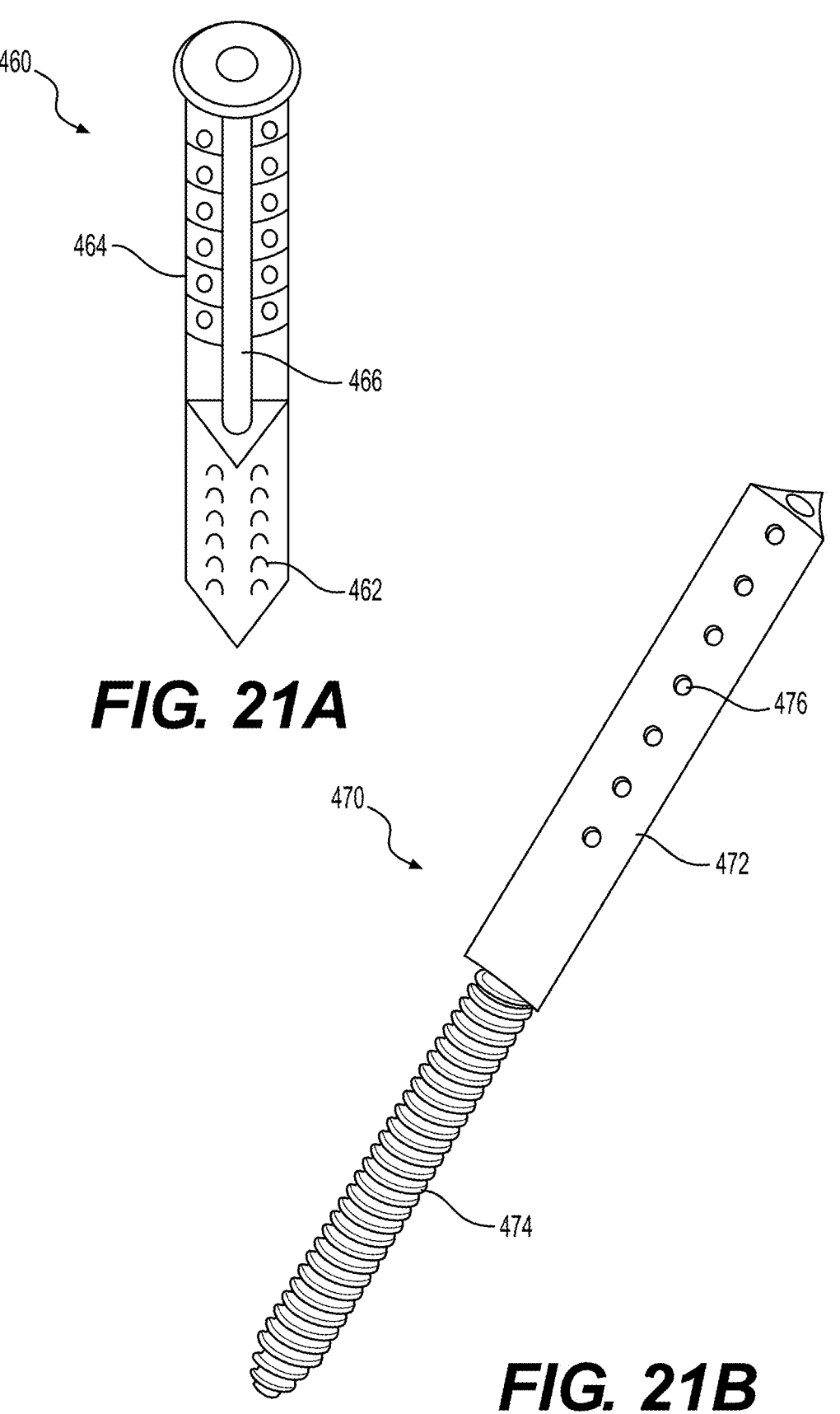
FIGS. 21A-21B show examples of implants with a triangular pin with joined screw.

Turning now to FIGS. 21A-21B, examples of implants 460, 470 having triangular pins 462, 474 with joined screws 464, 474 are shown. In FIG. 21A, the implant 460 includes a triangular shaped tip section 462 that is joined to a screw sleeve 464. The screw sleeve 464 may be threaded with optional graft slots or windows. In one embodiment, the screw sleeve 464 and triangular dowel 462 may be 3D printed. The screw sleeve 464 may rotate around a fixed inner shaft 466 such that the triangular pin portion 462 of the implant 460 is configured to advance across the sacroiliac joint. This provides benefits of torsional stability and the ability to precisely locate the implant via a driver. A textured surface may be provided on the triangular pin 462 to provide the ability to harvest bone that is then collected within the shape to promote fusion.

FIG. 21B shows an embodiment of implant 470 with triangular pin 472 and joined screw 474. In this embodiment, the triangular pin 472 is provided as a proximal portion of the implant 470 and the screw 474 is provided as a distal portion of the implant 470. The triangular pin 472 may have a central longitudinal bore for receiving the proximal end or head of the screw 474. The triangular pin 472 may also have a plurality of holes 476 transverse or perpendicular to the central longitudinal bore. The screw portion 474 is configured to rotate separately from the implant body 472. In this manner, the screw portion 474 of the implant 470 is configured to advance across the sacroiliac joint and the triangular pin 472 provides torsional stability.

Turning now to FIGS. 22A-22D and FIGS. 23A-23B, examples of fixations blocks with stabilization mounts are shown. In FIGS. 22A-22D, the implant 480 includes a transfixing spacer 482 configured to cross the sacroiliac joint and a plate or mounting block 484 for securing the implant 480. The block 484 acts to fixate the spacer 482 into position through a minimally invasive approach. In the embodiment shown in FIG. 22B, the mounted block 484 includes one or more angled screw holes 486 sized and dimensioned to accept one or more respective bone screws 488. In the embodiment shown in FIG. 22C, the mounted block 484 includes one or more nitinol wire anchors 490 or other deployable anchors. In the embodiment shown in FIG. 22D, the mounted block 484 includes angled anchor hole 492 for receiving anchor 494. The implant 480 includes a transfixing spacer 482, made from a polymer, metal, or bone. In one embodiment, the spacer 482 is made of allograft or autograft. The spacer 482 may be porous or have one or more graft windows 496 to allow for more optimal fusion. The spacer 482 may or may not be used with the mounting block 484. This provides versatility during surgery and increased options because of the buildable nature of the system.

Figure 23A:
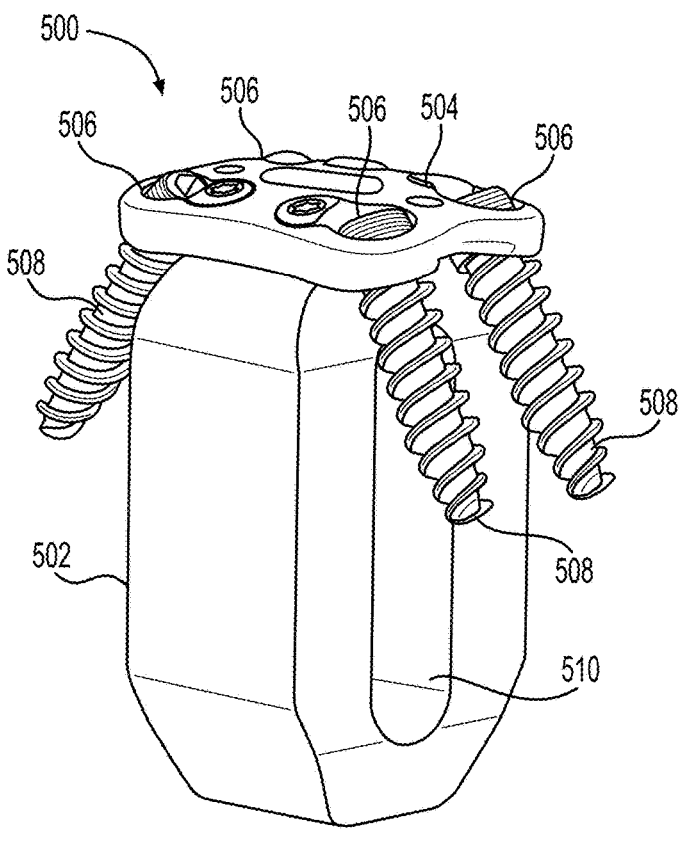
FIGS. 23A-23B show an implant with a spacer portion, plate portion, and fixation elements configured to secure the sacroiliac joint according to one embodiment.
Figure 23B:
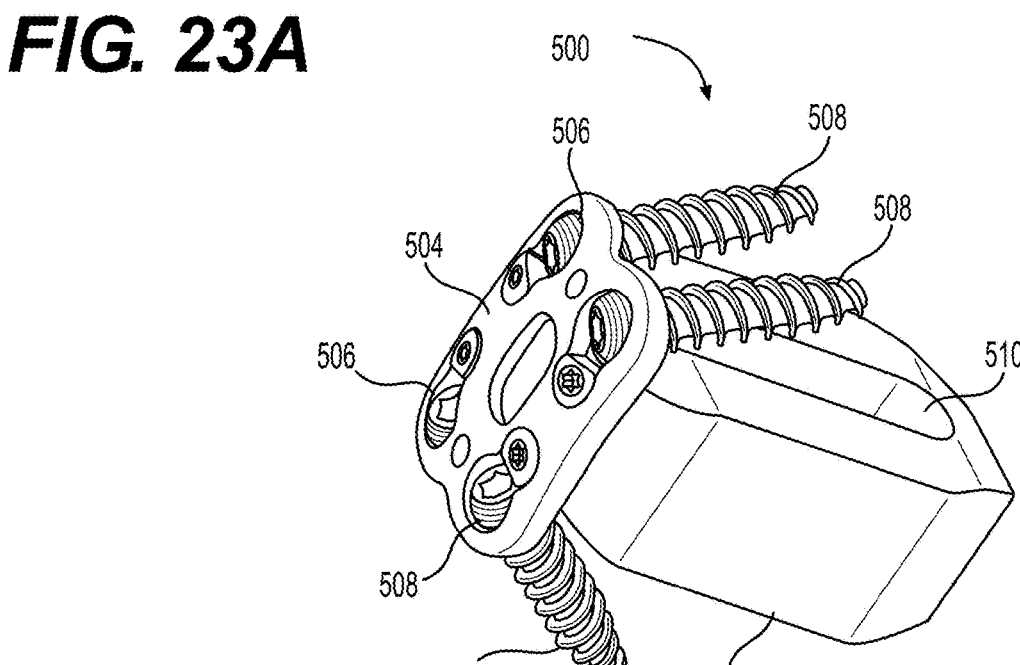

With further emphasis on FIGS. 23A-23B, the implant 500 includes a transfixing spacer 502 configured to cross the sacroiliac joint and a plate 504 for securing the implant 500. The plate 504 acts to fixate the spacer 502 into position through a minimally invasive approach. The plate 502 may define one or more angled screw holes 506 sized and dimensioned to accept one or more respective bone anchors 508, such as screws. In one embodiment, four screws 508 may be positioned through plate 502 with two screws 508 provided on opposite sides of the body of the spacer 502. The transfixing spacer 502 may be made from a polymer, metal, or bone, such as allograft or autograft. The spacer 502 may be porous and/or have one or more graft windows 510 configured to receive bone graft material to allow for more optimal fusion.

Figures 24A, 24B, 24C:
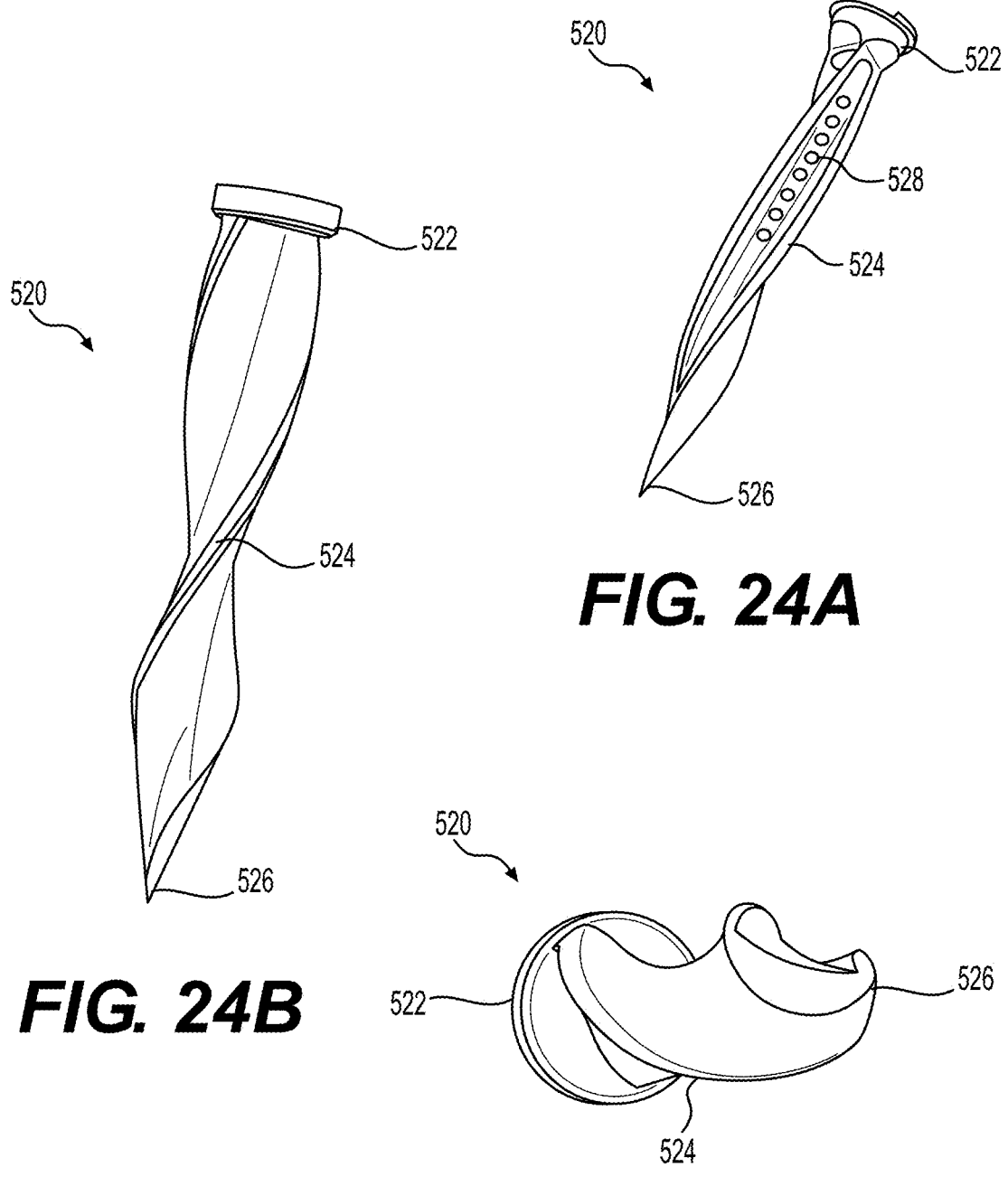
FIGS. 24A-24C show examples of triangular or spiral nail screws.
Figures 25A, 25B, 25C:
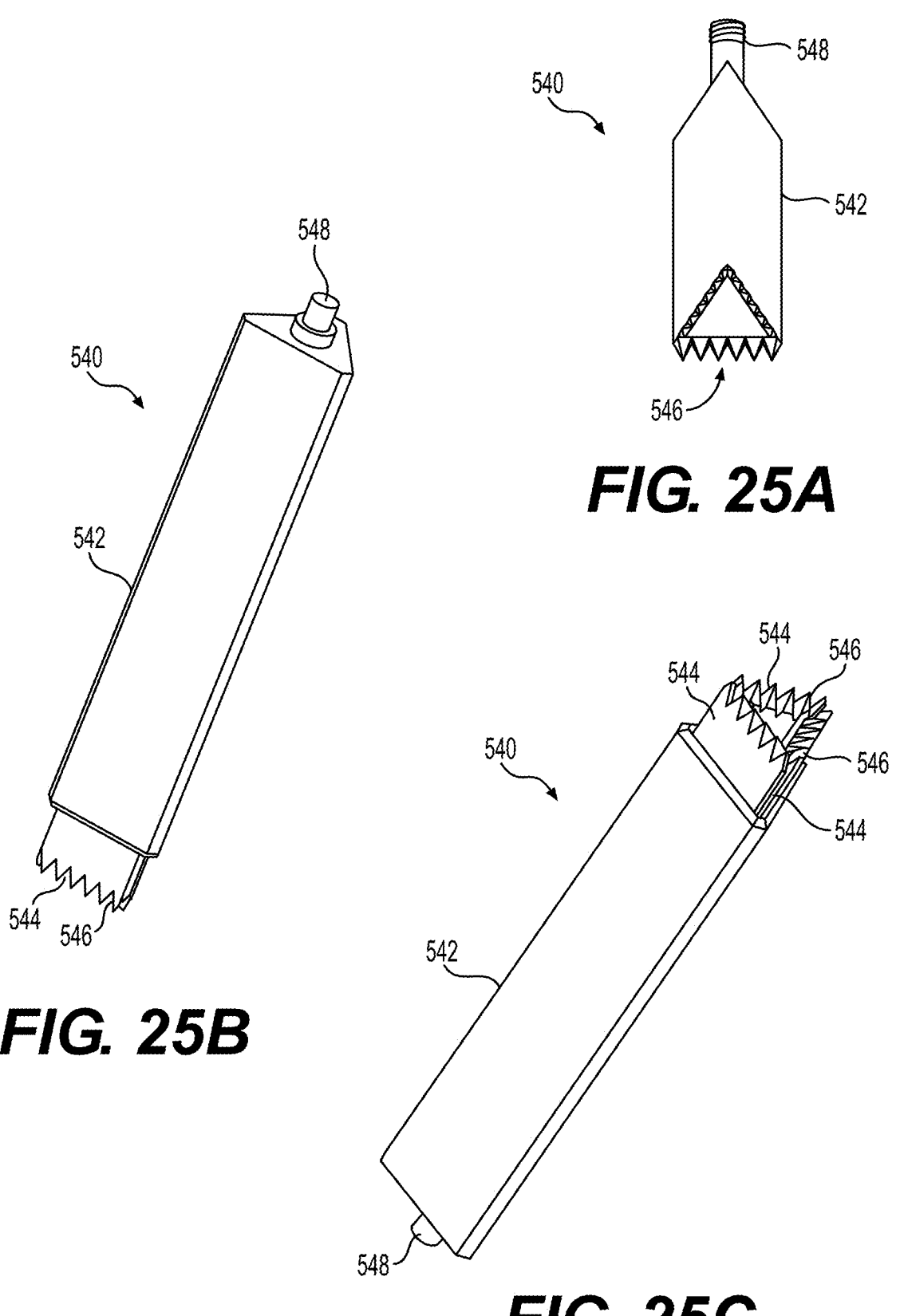
FIGS. 25A-25D show an oscillating broach instrument according to one embodiment.
Figure 25D:
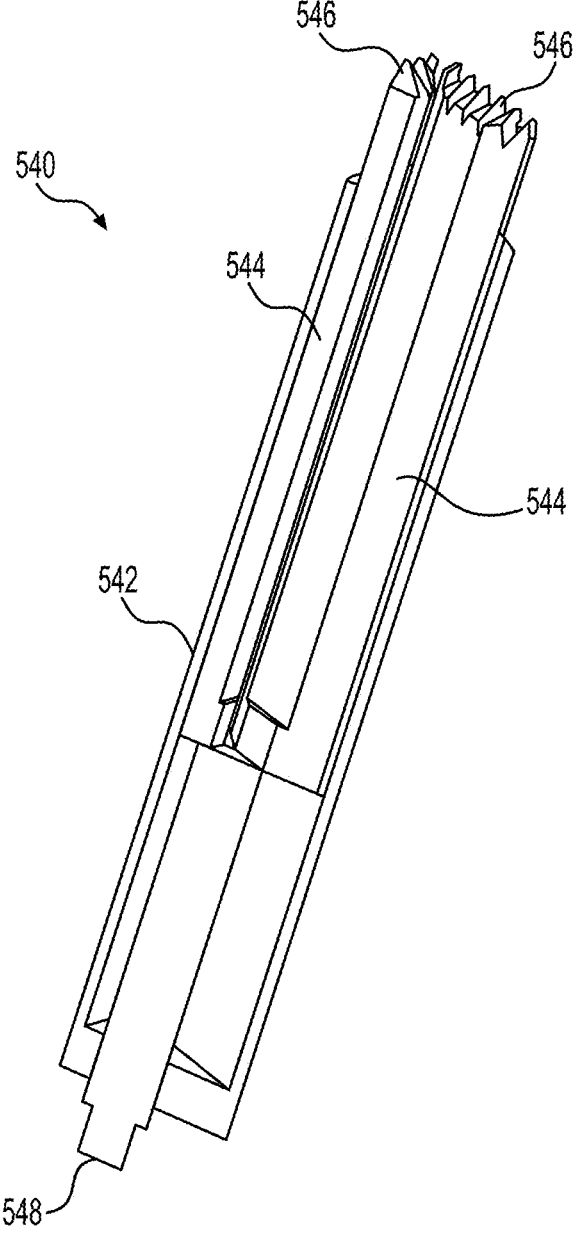

Turning now to FIGS. 24A-24C, examples of a triangular or spiral nail screw 520 are shown. The anchor 520 includes an enlarged proximal head 522, one or more spiral cutting flutes 524 and a pointed distal tip 526. The spiral cutting flutes 524 may be impacted through the sacroiliac joint for fixation. Rotation of the spiral implant 520 occurs due to the impaction force. The combination of flutes 524 and impaction may help to improve migration resistance but ease initial insertion. One or more graft holes 528 may be provided to allow for fusion across the joint. The anchor 520 may be 3D printed for manufacturing efficiency due to the complexity of its shape. A surface finish may be applied to optimize bony ingrowth. Positioning the implant 520 with the robotic and/or navigation system may also be done as a procedural approach, where multiple implants 520 may be aligned together for optimal fixation.

Turning now to FIGS. 25A-25D, examples of a triangular dowel automatic broach instrument 540 are shown. The ultrasonic bone cutting shaped bit may be helpful to create a shaped pilot hole when in use with the robotic and/or navigation systems. The arm of the robotic unit may be very sensitive to force, and the traditional impaction to implant a triangular pin, for example, may not be conducive to robotic operation. A smoother ultrasonic cutting tool, with less required impaction, may allow more fluid operation with the robotic system.

The broach 540 includes an outer sleeve 542 that houses one or more oscillating broach blades 544. The outer sleeve 542 may have a triangular shape or other suitable outer shape. The geometry and principle for the oscillatory broach 540 includes forming a triangular (or other shape) pin shaped hole across the sacroiliac joint before introduction of the pin or dowel. The blades 544 may protrude from one end of the sleeve 542 with a plurality of teeth 546 configured to cut bone. For the triangular shape, three blades 544 may extend from the distal end of the sleeve 542.

The blades 544 are coupled to an ultrasonic transducer 548 configured to oscillate blades 544. The oscillations may be produced from a device similar to an ultrasonic bone scalpel and transferred to the cutting teeth 546. The broach 540 is configured to efficiently slice crystalline bone while leaving elastic soft tissues largely unaffected. Cutting a triangular (or other geometric shape) channel before inserting an implant would reduce traditional hammering techniques and better allow the instrument to work in conjunction with the robotic and/or navigation system, as such systems may be sensitive to deflection and end effector loading. The broaching instrument 540 may allow smooth integration to create a procedural solution for an impaction style implant while trying to minimize large impaction forces.

Figure 26A:
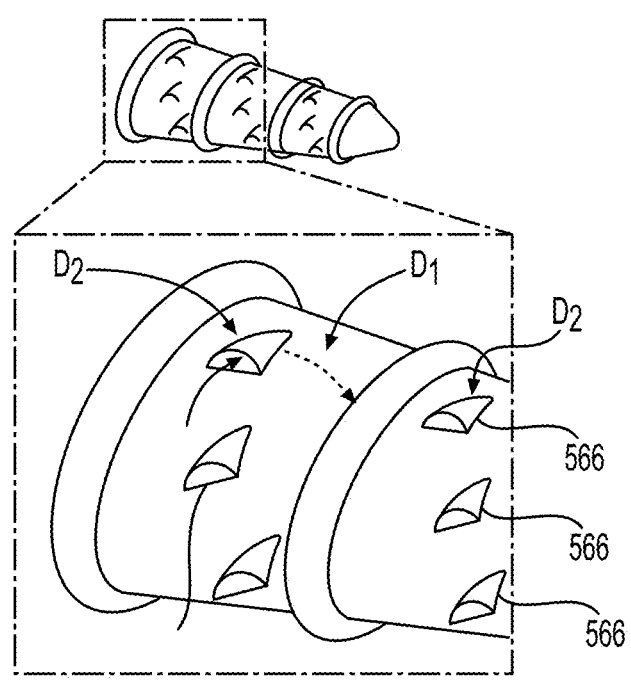
FIGS. 26A-26C show examples of auto-grating and self-packing screw shanks.
Figure 26B:
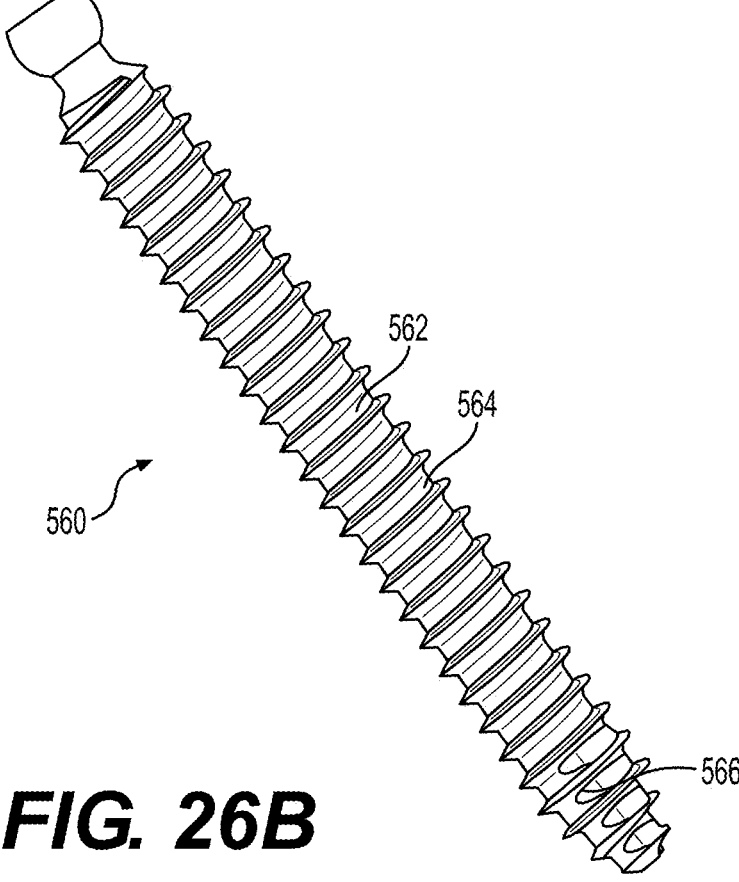
Figure 26C:
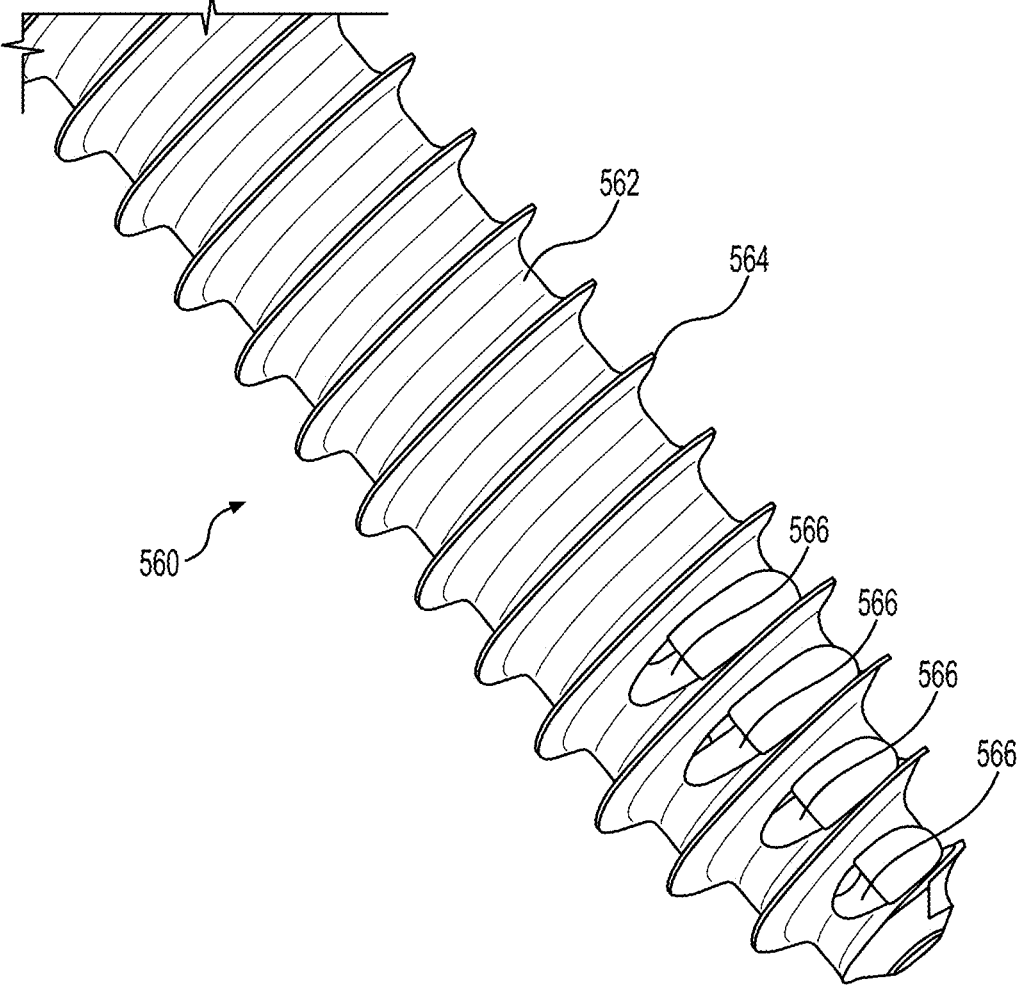

Turning now to FIGS. 26A-26C, examples of an auto-grating and self-packing screw 560 are shown. The screw 560 may have a hollow shank 562 with one or more external threads 564. The screw shank 562 has cheese grater-like serrations 566 positioned between the standard thread pitch to allow automatic gathering of bone material and internal collection. The diameter D1, D2 of a lower serration 566, at the point of tangency, may be sized to match that of the upper shank 562 and thus allow the threads 564 to provide fixation while removing material for graft that does not affect bone fixation mechanical properties. FIG. 26C shows four grating serrations 566 at the screw shank tip, but the number and location of grating serrations 566 may be applied to different sections of the shank 562 as well. The auto-grating type of shank 562 may be applied to a multitude of tulip bodies for a variety of techniques.

Turning now to FIGS. 27A-27B and FIGS. 28A-28D, embodiments of expandable thread profile screw shanks are shown. The screws 570, 580 include a shank 572 and one or more threads 574 that can transform shape to resist the motion of unthreading and to thereby help resist migration. The threads 574 may be parted in such a way as to allow a thread section to raise from the screw shank body 572 and block the counterclockwise motion required to remove the implant. Such a thread geometry change may be initiated by movement of an activating plunger, internal locking cylinder, cam, or similar mechanism such that the thread section is pushed outwards and retained in place. In other embodiments, a specific locking pin may be deployed with an axial or rotational movement of an internal member.

Figure 27A:
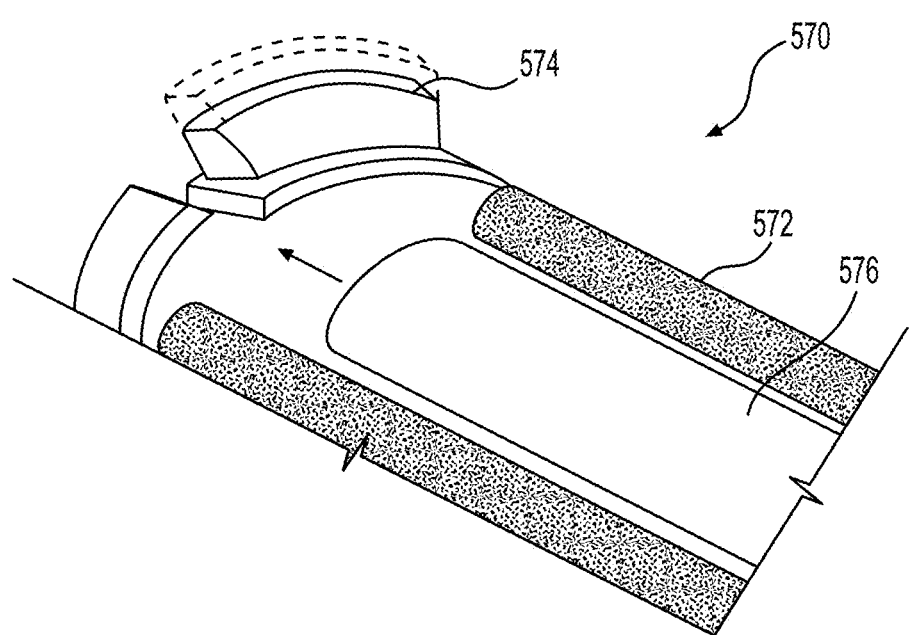
FIGS. 27A-27B show a thread expansion assembly with an internal plunger according to one embodiment.
Figure 27B:
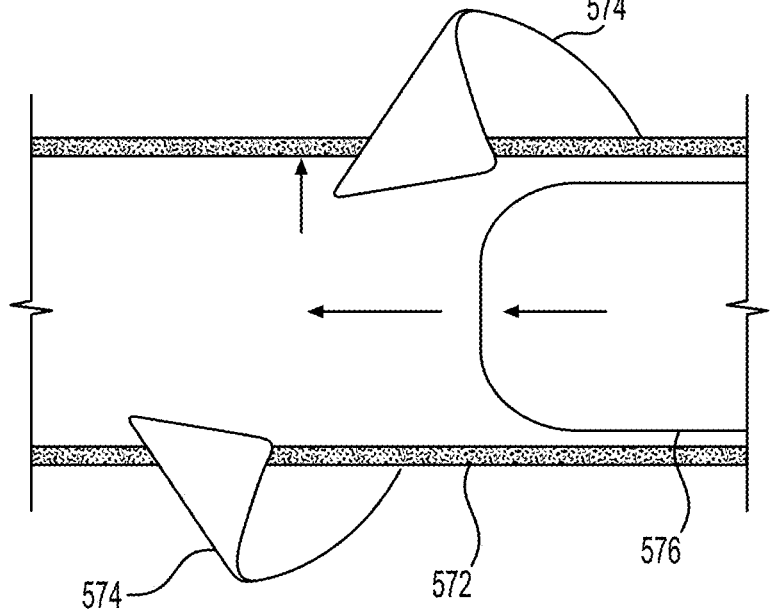

In the embodiment shown in FIGS. 27A-27B, the thread 574 flexes radially outwards as an internal cylinder 576 provides outward force. FIG. 27A shows the thread 574 prior to flexion. As an axial force is applied to the internal cylinder 576, the plunger 576 translates forward, thereby engaging with an inner portion of the thread 574 and forcing the thread 574 outward. FIG. 27B shows the activated threads 574 extending radially outward.

Figure 28A:
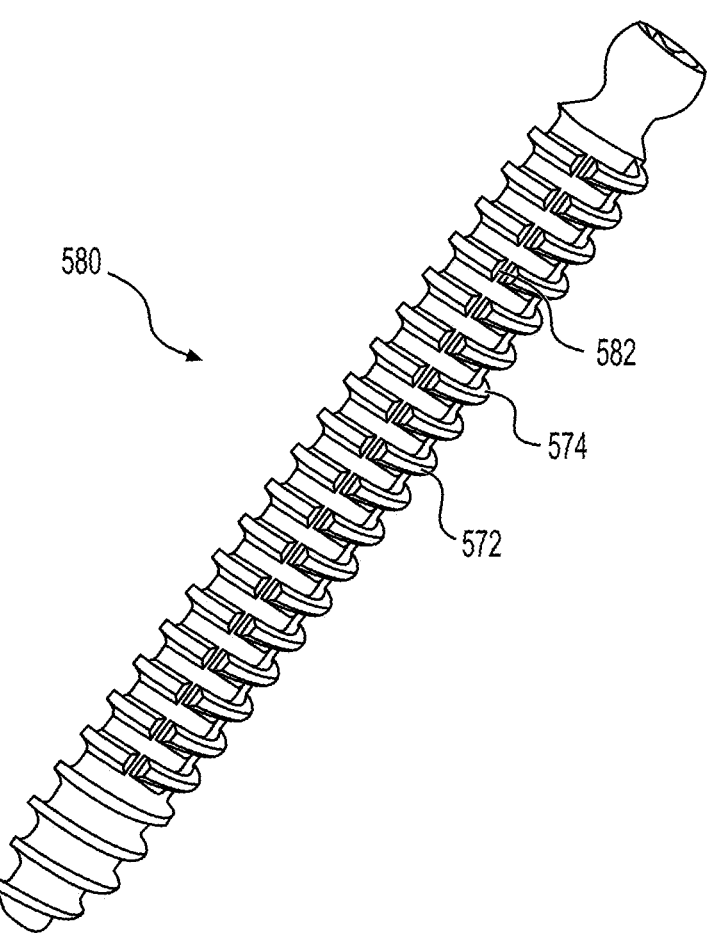
FIGS. 28A-28D show a screw with expandable threads due to an internal rotating cam according to one embodiment.
Figure 28B:
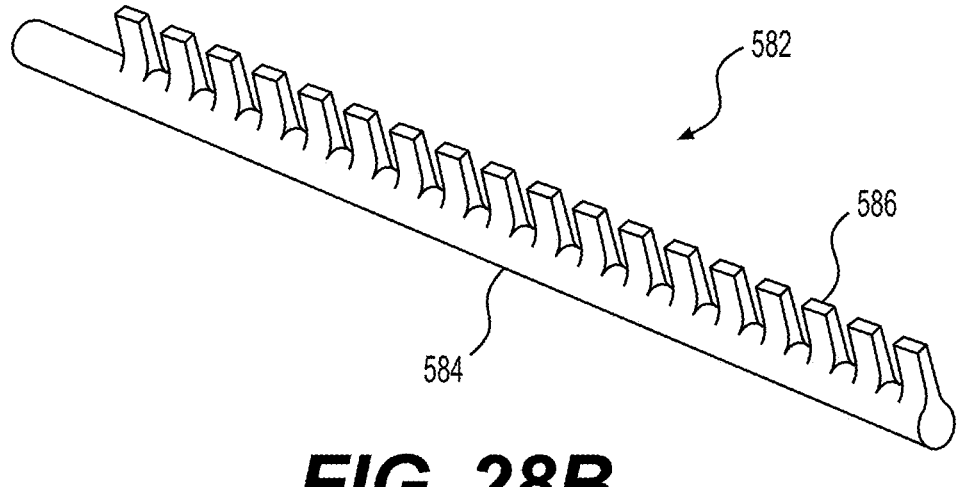
Figure 28C:
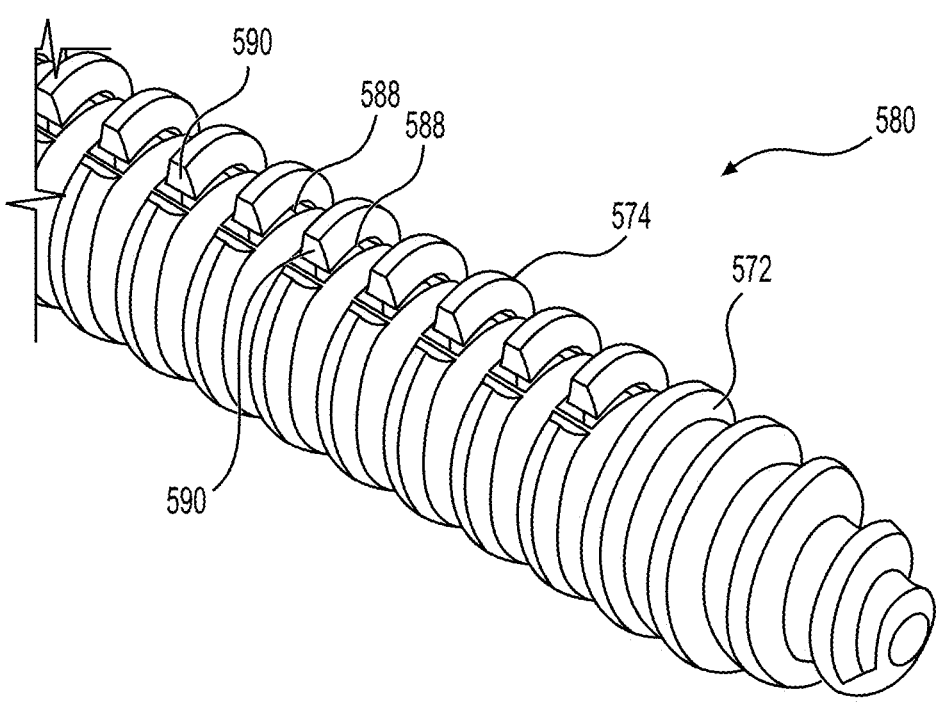
Figure 28D:
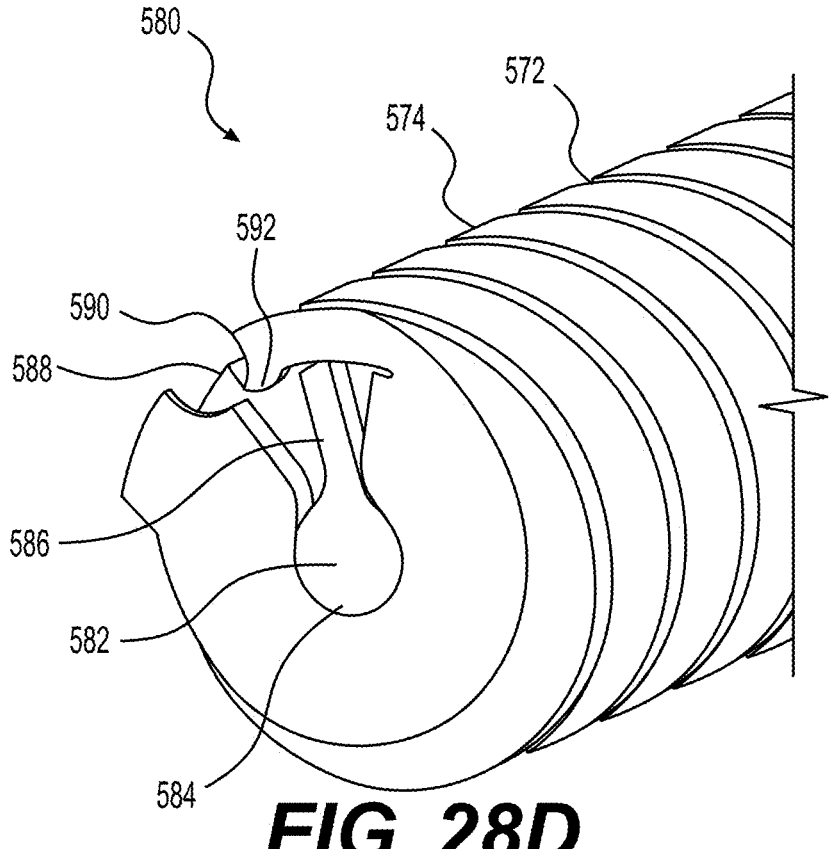

In the embodiment shown in FIGS. 28A-28D, each thread 574 is forced outward in a perpendicular motion to the axis of the screw shank 572 as an internal cylinder applies force to a conically shaped internal spline 582. As best seen in FIG. 28B, the internal spline 582 may be an internal cam rack having a cylindrical body 584 with a plurality of arms 586 extending therefrom. The internal spline 582 is receivable through the center of the shank 572 and each arm 586 is configured to engage with a respective thread portion 574. With further emphasis on FIG. 28C, each expandable thread portion 574 may be defined by one or more slits 588, thereby providing a free end 590 for each thread portion 574 configured to expand. As best seen in FIG. 28D, as a rotational force is applied to the cam 582, the arms 286 press against an inner projection 592 on the free end 590 of each thread 574, thereby flexing the threads 574 radially outward. In this way, the thread sections 574 raise from the screw shank body 572 and prevent rotational motion of the implant 580.

Figure 29:
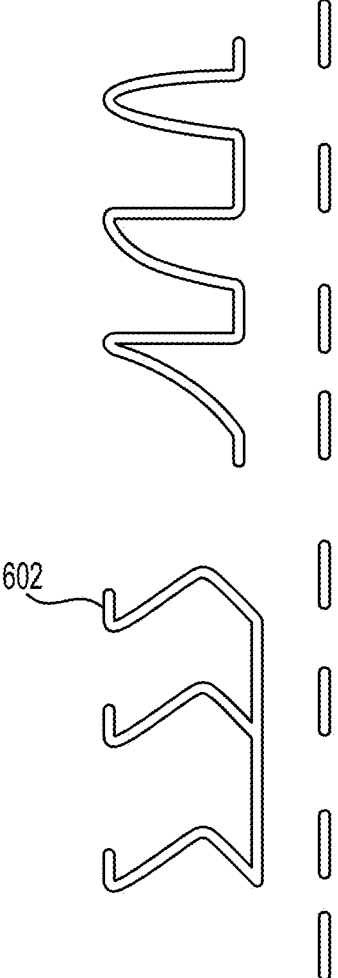
FIG. 29 shows a thread profile configured to fixate a screw across a sacroiliac joint according to one embodiment.

Turning now to FIG. 29, a bone interfacing thread configured to help fixate a screw that crosses the sacroiliac joint is shown according to one embodiment. FIG. 29 shows more traditional threads in the top portion and the new threads 602 that can help provide migration resistance in the bottom portion. The central axis is denoted by a vertical dashed line. The screw threads 602 are such that they positively engage the bone upon insertion to improve resistance to lateral forces. The thread interface may provide increased resistance to haloing, which is a concern for screws under higher loads in this anatomic location. These threads 602 may be applied to a multitude of implant types and materials.

In some embodiments, it may be possible to have interchangeable components and/or instrumentation between systems. This may help to reduce the number of sets required in the operating room and to streamline the techniques described herein. Using instrumentation across platforms further reduces the manufacturing burden by reducing the number of new instruments required.

It will be further understood that various changes in the details, materials, and arrangements of the parts which have been described and illustrated in order to explain the nature of this invention may be made by those skilled in the art without departing from the scope of the invention as expressed in the claims. One skilled in the art will appreciate that the embodiments discussed above are non-limiting. It will also be appreciated that one or more features of one embodiment may be partially or fully incorporated into one or more other embodiments described herein.

What is claimed is:

1. A sacroiliac joint fixation implant comprising:

an outer sleeve and an inner sleeve extending along a central longitudinal axis, the outer sleeve defining a central channel for receiving the inner sleeve, the inner sleeve defines an opening configured for receiving a spinal rod, and the inner sleeve includes an inner tapered section around the opening;

a clamp receivable through the inner sleeve, the clamp having a clasp configured for receiving the spinal rod; and a tightening bolt coupled to the clamp, wherein as the tightening bolt is rotated, the clamp is drawn back proximally into the tightening bolt, and the clasp is retracted into the inner tapered section, thereby locking the spinal rod to the implant, wherein the tightening bolt is partially cannulated with a blind hole and a proximal end of the clamp is received therein.

2. The implant of claim 1, wherein the outer and inner sleeves telescope with respect to one another to adjust an overall length of the implant.

3. The implant of claim 1, wherein the outer and inner sleeves have polygonal bodies.

4. The implant of claim 1, wherein a proximal end of the outer sleeve includes an enlarged lip configured to abut an ilium of a patient.

5. The implant of claim 1, wherein the clamp has an elongate body with the clasp at a distal end, the clasp includes a C-shaped body defining a circular opening configured to surround the spinal rod.

6. The implant of claim 1, wherein the tightening bolt includes an enlarged head configured to abut a proximal end of the outer sleeve.

7. The implant of claim 1, wherein a distal end of the tightening bolt is threadedly engaged with a proximal end of the clamp.

8. The implant of claim 1, where the inner tapered section is widest at a distal end of the inner sleeve and internally narrows proximally.

* * * * *